(12) United States Patent
Okazaki et al.

(10) Patent No.: US 9,881,137 B2
(45) Date of Patent: Jan. 30, 2018

(54) GOLF CLUB FITTING APPARATUS

(71) Applicants: DUNLOP SPORTS CO. LTD., Kobe-shi, Hyogo (JP); SUMITOMO RUBBER INDUSTRIES, LTD., Kobe-shi, Hyogo (JP)

(72) Inventors: Kousuke Okazaki, Kobe (JP); Masatoshi Kato, Kobe (JP); Masahiko Ueda, Kobe (JP); Naoyoshi Ueda, Kobe (JP); Shimpei Oyama, Kobe (JP)

(73) Assignees: DUNLOP SPORTS CO. LTD., Kobe-Shi, Hyogo (JP); SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 259 days.

(21) Appl. No.: 14/815,700

(22) Filed: Jul. 31, 2015

(65) Prior Publication Data
US 2016/0030803 A1    Feb. 4, 2016

(30) Foreign Application Priority Data

Aug. 1, 2014   (JP) .................................. 2014-158105
Dec. 24, 2014  (JP) .................................. 2014-261312
Jun. 17, 2015  (JP) .................................. 2015-121871

(51) Int. Cl.
| | |
|---|---|
| *A63B 69/36* | (2006.01) |
| *G06F 19/00* | (2011.01) |
| *G06F 3/01* | (2006.01) |
| *G06Q 10/06* | (2012.01) |
| *G09B 19/00* | (2006.01) |

(52) U.S. Cl.
CPC .......... *G06F 19/3481* (2013.01); *G06F 3/011* (2013.01); *G06Q 10/0639* (2013.01); *G09B 19/0038* (2013.01); *A63B 69/3632* (2013.01); *A63B 2069/3605* (2013.01)

(58) Field of Classification Search
None
See application file for complete search history.

(56) References Cited

U.S. PATENT DOCUMENTS

| | | | |
|---|---|---|---|
| 8,758,171 B2 * | 6/2014 | Hasegawa | A63B 24/0003 473/409 |
| 2011/0028248 A1 * | 2/2011 | Ueda | A63B 69/3614 473/409 |
| 2011/0230273 A1 * | 9/2011 | Niegowski | A43B 3/0005 473/199 |

(Continued)

FOREIGN PATENT DOCUMENTS

JP    2013-226375 A    11/2013

*Primary Examiner* — Lawrence Galka
(74) *Attorney, Agent, or Firm* — Birch, Stewart, Kolasch & Birch, LLP

(57) ABSTRACT

Provided is a fitting apparatus that accurately and objectively determines an optimal swingability index, which is a swingability index of a golf club suited to a golfer. The fitting apparatus is provided with an acquisition unit, a calculation unit, and a determination unit. The acquisition unit acquires a measurement value obtained by measuring a swing action of a test club by the golfer with a measurement device. The calculation unit calculates a swing index indicating a feature amount of the swing action, based on the measurement value. The determination unit determines the optimal swingability index, according to a magnitude of the swing index.

15 Claims, 35 Drawing Sheets

(56) References Cited

U.S. PATENT DOCUMENTS

2013/0165246 A1* 6/2013 Jeffery ................... A63B 69/36
                                                            473/223
2013/0260923 A1   10/2013 Okazaki et al.
2013/0344973 A1* 12/2013 Margoles ........... A63B 69/3623
                                                            473/223

* cited by examiner

GOLF CLUB FITTING APPARATUS

CROSS REFERENCE TO RELATED APPLICATIONS

This application claims priorities to Japanese Patent Applications No. 2014-158105 filed on Aug. 1, 2014, No. 2014-261312 filed on Dec. 24, 2014, and No. 2015-121871 filed on Jun. 17, 2015, which are hereby incorporated by reference in their entirety.

FIELD OF INVENTION

The present invention relates to a golf club fitting apparatus that determine a swingability index of a golf club suited to a golfer (hereinafter, optimal swingability index).

BACKGROUND

Heretofore, various fitting methods that involve getting a golfer to take practice hits with test clubs, measuring the swing action, and determining a golf club suited to the golfer based on the measurement values have been proposed. In JP 2013-226375A, in order to select a golf club suited to a golfer, the importance of taking into consideration factors such as the weight of the club and the length of the club is pointed out.

SUMMARY OF INVENTION

The weight of a golf club is one index representing the swingability of a golf club. Incidentally, the weight of a golf club suited to a golfer (hereinafter, optimal club weight) may be determined at the time of fitting, with the optimal club weight often being empirically determined by an experienced club fitter, based on the weight of the golf clubs the golfer is currently using, the results of taking test hits with various golf clubs, a visual evaluation of his or her swing tempo, and the like. However, there is a problem in that such fitting methods that depend on experience and intuition are not objective, and individual differences occur in the fitting results. Furthermore, the inventors considered it important to also focus on swingability indices other than the weight of the golf club, in order to determine a golf club suited to a golfer through fitting.

An object of the present invention is to provide a fitting apparatus that accurately determine an optimal swingability index, which is a swingability index of a golf club suited to a golfer.

A fitting apparatus according to a first aspect of the present invention is a fitting apparatus configured to determine an optimal swingability index, which is a swingability index of a golf club suited to a golfer, that includes an acquisition unit, a calculation unit, and a determination unit. The acquisition unit is configured to acquire a measurement value obtained by measuring a swing action of a test club by the golfer with a measurement device. The calculation unit is configured to calculate a swing index indicating a feature amount of the swing action, based on the measurement value. The determination unit is configured to determine the optimal swingability index, according to a magnitude of the swing index.

A fitting apparatus according to a second aspect of the present invention is the fitting apparatus according to the first aspect in which the calculation unit is configured to calculate a plurality of types of swing indices, and the determination unit is configured to determine the optimal swingability index, according to the magnitudes of the plurality of types of the swing indices.

A fitting apparatus according to a third aspect of the present invention is the fitting apparatus according to the first aspect or the second aspect, in which the swing index includes an index representing energy or torque that is exerted by the golfer during the swing action or an index that is correlated with the energy or torque that is exerted by the golfer during the swing action.

A fitting apparatus according to a fourth aspect of the present invention is the fitting apparatus according to the third aspect, in which the swing index includes at least one of arm energy of the golfer during the swing action, torque about a shoulder of the golfer during the swing action, and head speed.

A fitting apparatus according to a fifth aspect of the present invention is the fitting apparatus according to the fourth aspect, in which the calculation unit is configured to calculate the head speed achieved during the swing action, and the determination unit is configured to determine the optimal swingability index, according to the magnitude of the head speed, in addition to the magnitude of at least one of the arm energy and the torque about the shoulder.

A fitting apparatus according to a sixth aspect of the present invention is the fitting apparatus according to any of the first aspect to the fifth aspect, in which the determination unit is configured to determine the optimal swingability index to take a larger value as the swing index increases or decreases.

A fitting apparatus according to a seventh aspect of the present invention is the fitting apparatus according to any of the first aspect to the sixth aspect that further includes a storage unit which stores correspondence data defining a correspondence between the magnitude of the swing index and the magnitude of the optimal swingability index for each type of the test club, and in which the determination unit is configured to determine the optimal swingability index according to the type of the test club, by referring to the correspondence data in the storage unit.

A fitting apparatus according to an eighth aspect of the present invention is the fitting apparatus according to any of the first aspect to the seventh aspect, in which the swingability index includes at least one of a weight of the golf club, a moment of inertia of the golf club, and a moment of inertia about a shoulder of the golfer.

A fitting apparatus according to a ninth aspect of the present invention is the fitting apparatus according to any of the first aspect to the seventh aspect, in which the swingability index includes a weight of the golf club.

A fitting apparatus according to a tenth aspect of the present invention is the fitting apparatus according to the ninth aspect that further includes an optimal club specification unit configured to specify a golf club having a small swing moment of inertia and a large grip end moment of inertia from among a plurality of golf clubs that match an optimal club weight, which is a weight of the golf club suited to the golfer.

A fitting method according to an eleventh aspect of the present invention is a fitting method for determining an optimal swingability index, which is a swingability index of a golf club suited to a golfer, that includes the following steps.

(1) A step of measuring a swing action of a test club by the golfer with a measurement device.
(2) A step of calculating a swing index indicating a feature amount of the swing action, based on the measurement value measured with the measurement device.

(3) A step of determining the optimal swingability index, according to a magnitude of the swing index.

A non-transitory computer readable medium storing a fitting program according to a twelfth aspect of the present invention is for determining an optimal swingability index, which is a swingability index of a golf club suited to a golfer, the program causing a computer to executes the following steps.
(1) A step of acquiring a measurement value obtained by measuring a swing action of a test club by the golfer with a measurement device.
(2) A step of calculating a swing index indicating a feature amount of the swing action, based on the measurement value measured with the measurement device.
(3) A step of determining the optimal swingability index, according to a magnitude of the swing index.

A certain relationship can exist between an optimal swingability index and a predetermined feature amount of the swing action. For example, the inventors found that the optimal club weight, the optimal value of the moment of inertia of a golf club (hereinafter, optimal club MI) and the optimal value of the moment of inertia about the golfer's shoulder (hereinafter, optimal swing MI) are correlated with the energy or torque exerted by the golfer during the swing action. In view of this, according to the present invention, an optimal swingability index is determined according to the size of an index (swing index) that is a feature amount of the swing action and has a certain relationship with the optimal swingability index. The optimal swingability index can thereby be accuracy determined objectively. Note that the optimal club MI includes the optimal value of the moment of inertia about the grip end of the golf club (hereinafter, optimal grip end MI) and the optimal value of the moment of inertia about the center of gravity of the golf club.

In the invention according to both the third aspect and the eighth aspect in particular, at least one of the optimal club weight, the optimal club MI, and the optimal swing MI is determined according to the size of an index representing the energy or torque exerted by a golfer during the swing action of a test club by the golfer, or the size of an index correlated thereto. At least one of the optimal club weight, the optimal club MI and the optimal swing MI can thereby be accuracy determined objectively.

DETAILED DESCRIPTION OF THE PREFERRED EMBODIMENTS

Hereinafter, a golf club fitting apparatus, method and program according to a number of embodiments of the present invention will be described, with reference to the drawings.

1. First Embodiment

1-1. Schematic Configuration of Fitting System

Figure 1:
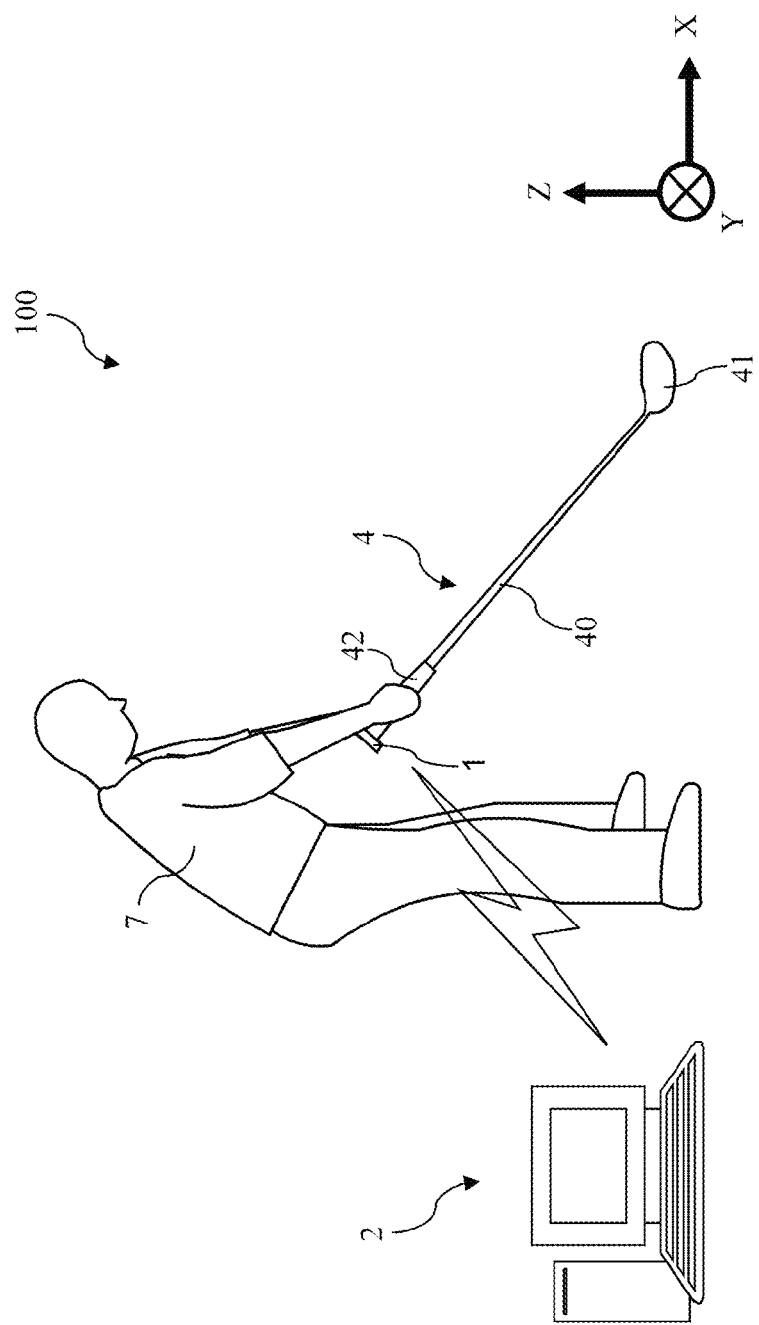
FIG. 1 is a diagram showing a fitting system provided with a fitting apparatus according to a first embodiment of the present invention.
Figure 2:
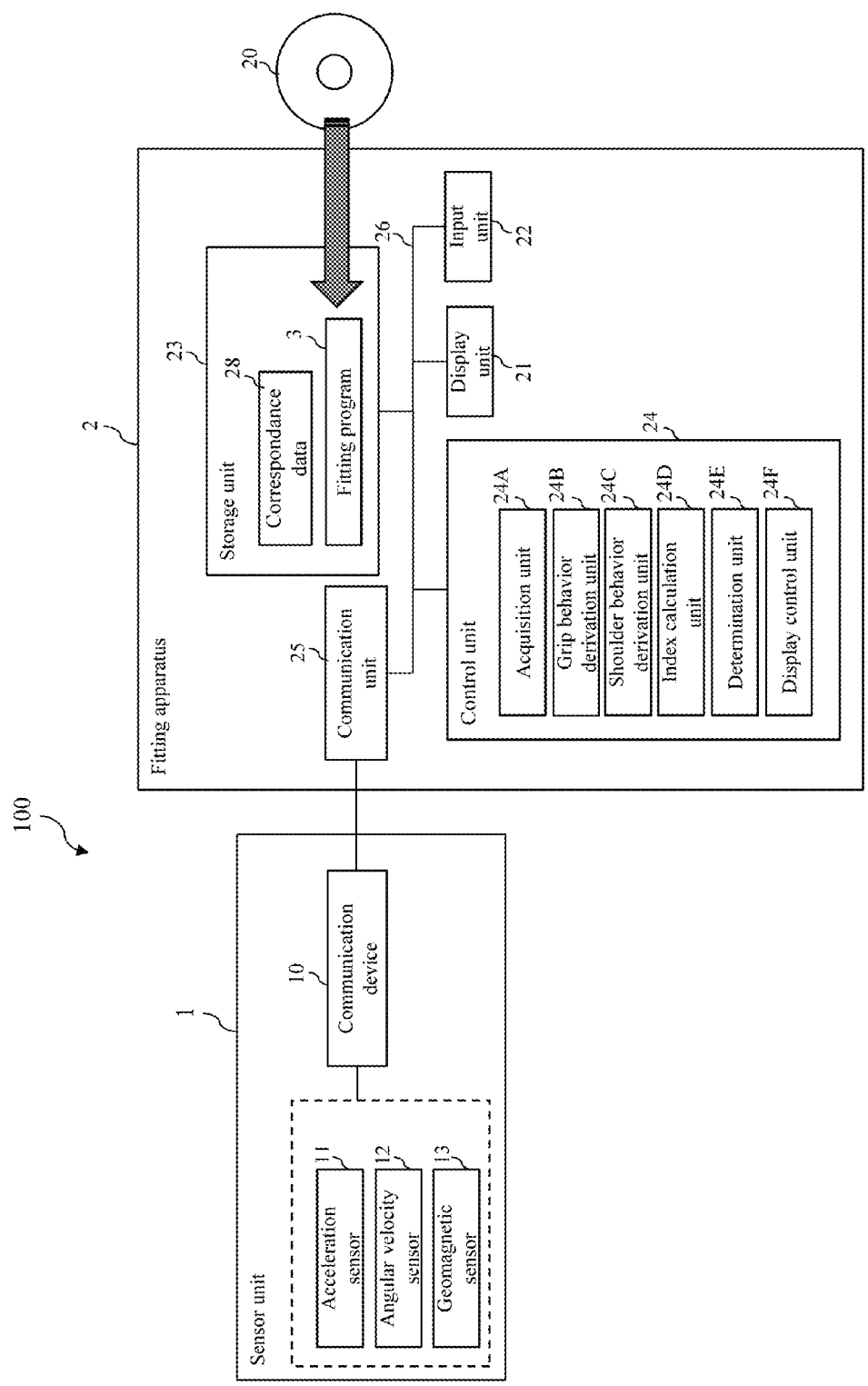
FIG. 2 is a functional block diagram of a fitting system.

FIGS. 1 and 2 show the overall configuration of a fitting system 100 that is provided with a fitting apparatus 2 according to the present embodiment. The fitting apparatus 2 analyzes the swing action of a golf club 4, based on measurement data obtained by measuring the swing action of the golf club 4 by a golfer 7. In the present embodiment, the fitting apparatus 2 is applied to assisting fitting of the golf club 4. The swing action is measured by a sensor unit 1 (measurement device) attached to a grip 42 of the golf club 4, and the fitting apparatus 2 together with the sensor unit 1 constitutes the fitting system 100.

Hereinafter, the configuration of the sensor unit 1 and the fitting apparatus 2 will be described, followed by description of the flow of swing action analysis processing.

1-1-1. Configuration of Sensor Unit

Figure 3:
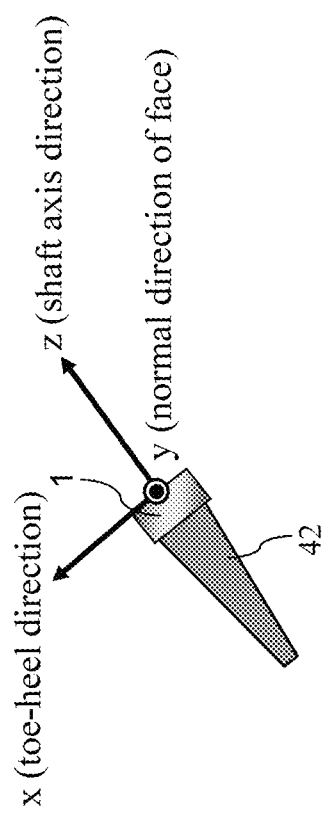
FIG. 3 is a diagram illustrating an xyz local coordinate system that is based on the grip of a golf club.

The sensor unit 1 is, as is shown in FIGS. 1 and 3, attached to an end portion of the grip 42 of the golf club 4 on the opposite side to a head 41, and measures the behavior of the grip 42. Note that the golf club 4 is a common golf club, and is constituted by a shaft 40, the head 41 provided at one end of the shaft 40, and the grip 42 provided at the other end of the shaft 40. The sensor unit 1 is configured to be compact and lightweight so as to not impede the swing action. As shown in FIG. 2, an acceleration sensor 11, an angular velocity sensor (gyro sensor) 12 and a geomagnetic sensor 13 are mounted in the sensor unit 1 according to the present embodiment. A communication device 10 for transmitting measurement data that is measured by these sensors 11 to 13 to the external fitting apparatus 2 is also mounted in the sensor unit 1. Note that, in the present embodiment, the communication device 10 is a wireless communication device so as to not impede the swing action, but may be configured to be connected to the fitting apparatus 2 via a cable in a wired manner.

The acceleration sensor 11, the angular velocity sensor 12, and the geomagnetic sensor 13 respectively measure grip acceleration, grip angular velocity and grip geomagnetism in an xyz local coordinate system that is based on the grip 42. More specifically, the acceleration sensor 11 measures grip accelerations $a_x$, $a_y$ and $a_z$ in the x-axis, y-axis and z-axis directions. The angular velocity sensor 12 measures grip angular velocities $\omega_x$, $\omega_y$ and $\omega_z$ about the x-axis, the y-axis, and the z-axis. The geomagnetic sensor 13 measures grip geomagnetisms $m_x$, $m_y$ and $m_z$ in the x-axis, y-axis and z-axis directions. These measurement data are acquired as time-series data at a predetermined sampling period $\Delta t$. Note that the xyz local coordinate system is a three-axis orthogonal coordinate system defined as shown in FIG. 3. That is, the z-axis coincides with the direction in which the shaft 40 extends, and the direction from the head 41 toward the grip 42 is the z-axis positive direction. The x-axis is oriented so as to be aligned as closely as possible with the toe-heel direction of the head 41, and the y-axis is oriented so as to be aligned as closely as possible with the normal direction of the face of the head 41.

In the present embodiment, the measurement data measured by the acceleration sensor 11, the angular velocity sensor 12, and the geomagnetic sensor 13 is transmitted to the fitting apparatus 2 via the communication device 10 in real time. However, a configuration may, for example, be adopted in which the measurement data is stored in a storage device within the sensor unit 1, and, after the end of the swing action, the measurement data is retrieved from the storage device and delivered to the fitting apparatus 2.

1-1-2. Configuration of Fitting Apparatus

The configuration of the fitting apparatus 2 will be described with reference to FIG. 2. The fitting apparatus 2 is manufactured by installing a fitting program 3 according to the present embodiment that is stored in a computer readable recording medium 20 such as a CD-ROM or a USB memory on a general-purpose personal computer from the recording medium 20. The fitting program 3 is software for analyzing a swing action based on measurement data sent from the sensor unit 1, and outputting information that assists the selection of golf clubs suited to the golfer 7. The fitting program 3 causes the fitting apparatus 2 to execute operations which will be discussed later.

The fitting apparatus 2 is provided with a display unit 21, an input unit 22, a storage unit 23, a control unit 24, and a communication unit 25. These units 21 to 25 are connected via a bus line 26, and can communicate with each other. In the present embodiment, the display unit 21 is constituted by a liquid crystal display or the like, and displays information which will be discussed later to a user. Note that a user as referred to here is a general term for persons that require fitting results such as the golfer 7 or his or her instructor. Also, the input unit 22 can be constituted by a mouse, a keyboard, a touch panel or the like, and accept operations to the fitting apparatus 2 from the user.

The storage unit 23 is constituted by a non-volatile storage device such as a hard disk. Measurement data sent from the sensor unit 1 is saved to the storage unit 23, in addition to the fitting program 3 being stored therein. Also, correspondence data 28 is stored in the storage unit 23. Correspondence data 28, as will be discussed in detail later, is data defined for each of various models of the golf club 4, and indicates conditions for determining the optical club weight. The communication unit 25 is a communication interface that enables communication between the fitting apparatus 2 and an external apparatus, and receives data from the sensor unit 1.

The control unit 24 can be constituted by a CPU, a ROM, a RAM, and the like. The control unit 24 operates in a virtual manner as an acquisition unit 24A, a grip behavior derivation unit 24B, a shoulder behavior derivation unit 24C, an index calculation unit 24D, a determination unit 24E and a display control unit 24F, by reading out and executing the fitting program 3 stored in the storage unit 23. The operations of each of the units 24A to 24F will be discussed in detail later.

1-2. Swing Action Analysis Processing

Next, swing action analysis processing that is performed by the fitting system 100 and is for fitting the golf club 4 will be described. The analysis processing according to the present embodiment is constituted by the following seven processes.

(1) A measurement process of measuring measurement data of grip accelerations $a_x$, $a_y$ and $a_z$, grip angular velocities $\omega_x$, $\omega_y$ and $\omega_z$, and grip geomagnetisms $m_x$, $m_y$ and $m_z$ in the xyz local coordinate system.

(2) A first transformation process of transforming the measurement data of the xyz local coordinate system obtained with the measurement process into grip accelerations $a_X$, $a_Y$ and $a_Z$ and grip angular velocities $\omega_X$, $\omega_Y$ and $\omega_Z$ in an XYZ global coordinate system (in the first transformation process, grip velocities $v_X$, $v_Y$ and $v_Z$ in the XYZ global coordinate system are also derived).

(3) A second transformation process of transforming the behavior of the grip 42 in the XYZ global coordinate system (grip angular velocities $\omega_X$, $\omega_Y$, $\omega_Z$ and grip velocities $v_X$, $v_Y$ and $v_Z$) into the behavior of the grip 42 in swing plane P (discussed later).

(4) A shoulder behavior derivation process of deriving the behavior of a pseudo shoulder of the golfer 7 in swing plane P, based on the behavior of the grip 42 in swing plane P.

(5) An index calculation process of calculating swing indices (in the present embodiment, three indices relating to average shoulder torque $T_{AVE}$, arm energy $E_{AVE}$ and head speed $V_h$ that are exerted by the golfer 7) to be used as indices for determining an optimal swingability index (in the present embodiment, optimal club weight), based on the behavior of the grip 42 and the behavior of the pseudo shoulder.

(6) An optimal total weight determination process of determining the optimal club weight, based on swing indices.

(7) An optimal shaft determination process of calculating the weight (hereinafter, optimal shaft weight) and bending stiffness (hereinafter, optimal stiffness) of the shaft 40 suited to the golfer 7.

Hereinafter, these processes will be described in the above order.

Note that the XYZ global coordinate system is a three-axis orthogonal coordinate system defined as shown in FIG. 1. That is, the Z-axis extends vertically upward from below, the X-axis extends from the back of the golfer 7 toward his or her abdomen, and the Y-axis extends in a direction from the ball hitting point toward the target point in parallel to a horizontal plane.

1-2-1. Measurement Process

In the measurement process, the golfer 7 swings the golf club 4 having the sensor unit 1 attached. The golf club 4 swung in the measurement process is one of two test clubs. As will be discussed in detail later, in the case where, however, the test club initially selected is judged to not suit the golfer 7, the golfer 7 then also swings the other golf club. These test clubs are different types of golf clubs, and, in the present embodiment, one is golf club having pro specifications (hereinafter, pro model club), and the other is a golf club suited to an average player (hereinafter, average model club). Also, in the present embodiment, the pro model club is heavier than the average model club. Which of the test clubs is swung in the measurement process is decided based on factors such as the golfer preference and experience.

Next, the measurement data of grip accelerations $a_x$, $a_y$ and $a_z$, grip angular velocities $\omega_x$, $\omega_y$ and $\omega_z$, and grip geomagnetisms $m_x$, $m_y$, and $m_z$ during the swing action of a golf club 4 such as the above are measured by the sensor unit 1. This measurement data is transmitted to the fitting apparatus 2 via the communication device 10 of the sensor unit 1. On the other hand, in the fitting apparatus 2, the acquisition unit 24A receives the measurement data via the communication unit 25, and stores the received measurement data in the storage unit 23. In the present embodiment, time-series measurement data at least from address to impact is measured.

Figure 4D:
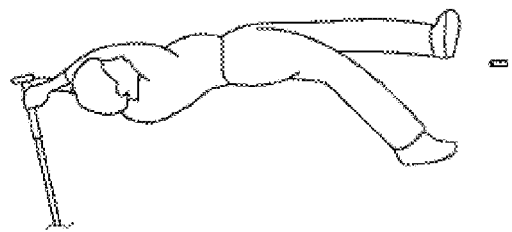
FIG. 4D is a diagram showing a finish state.
Figure 4C:
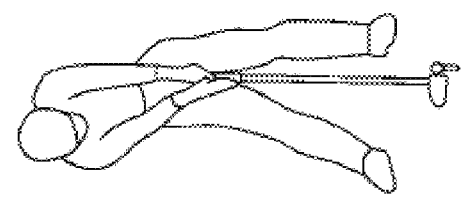
FIG. 4C is a diagram showing an impact state.
Figure 4B:
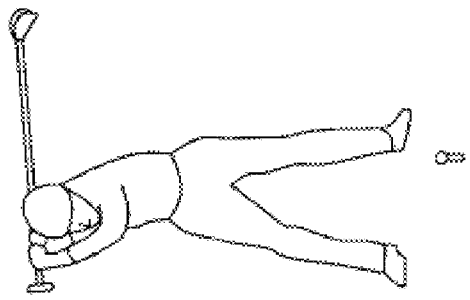
FIG. 4B is a diagram showing a top state.
Figure 4A:
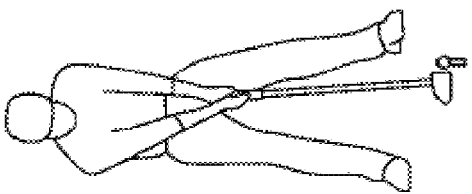
FIG. 4A is a diagram showing an address state.

Note that generally the swing action of a golf club proceeds in order of address, top, impact, and finish. The address refers to an initial state where the head 41 of the golf club 4 is disposed near the ball, as shown in FIG. 4A, and the top refers to a state where the golf club 4 is taken away from the address and the head 41 is swung up to its highest position, as shown in FIG. 4B. The impact refers to a state at the moment where the golf club 4 is swung down from the top and the head 41 impacts the ball, as shown in FIG. 4C, and the finish refers to a state where the golf club 4 is swung through to the front after the impact, as shown in FIG. 4D.

Also, in the measurement process, multiple practice hits are preferably taken with the golf club 4, with five or more practice hits preferably being taken. In this case, the average value of the measurement data can be calculated and used in subsequent operations. Also, in order to remove abnormal values caused by miss hits, measurement errors or the like, it is preferable to calculate standard deviation $\sigma$ of the measurement data to obtain measurement data in which the measurement data of all the practice hits preferably falls within an average value $\pm 1.65\sigma$, and more preferably falls within an average value $\pm 1.28\sigma$. In the case where standard deviation $\sigma$ of the measurement data is calculated by the control unit 24 in order to perform this check, and the value of $\sigma$ does not meet the above conditions, a message seeking additional measurement or remeasurement may then be displayed on the display unit 21. Note that a configuration may be adopted in which, rather than the average value of the measurement data itself, the average value of processing values (e.g., average shoulder torque $T_{AVE}$, arm energy $E_{AVE}$, and head speed $V_h$ discussed later) is calculated based on the measurement data. A check on the reliability of data based on standard deviation $\sigma$ can also be performed in the case of calculating the average value of processing values.

1-2-2. First Transformation Process

Figure 5:
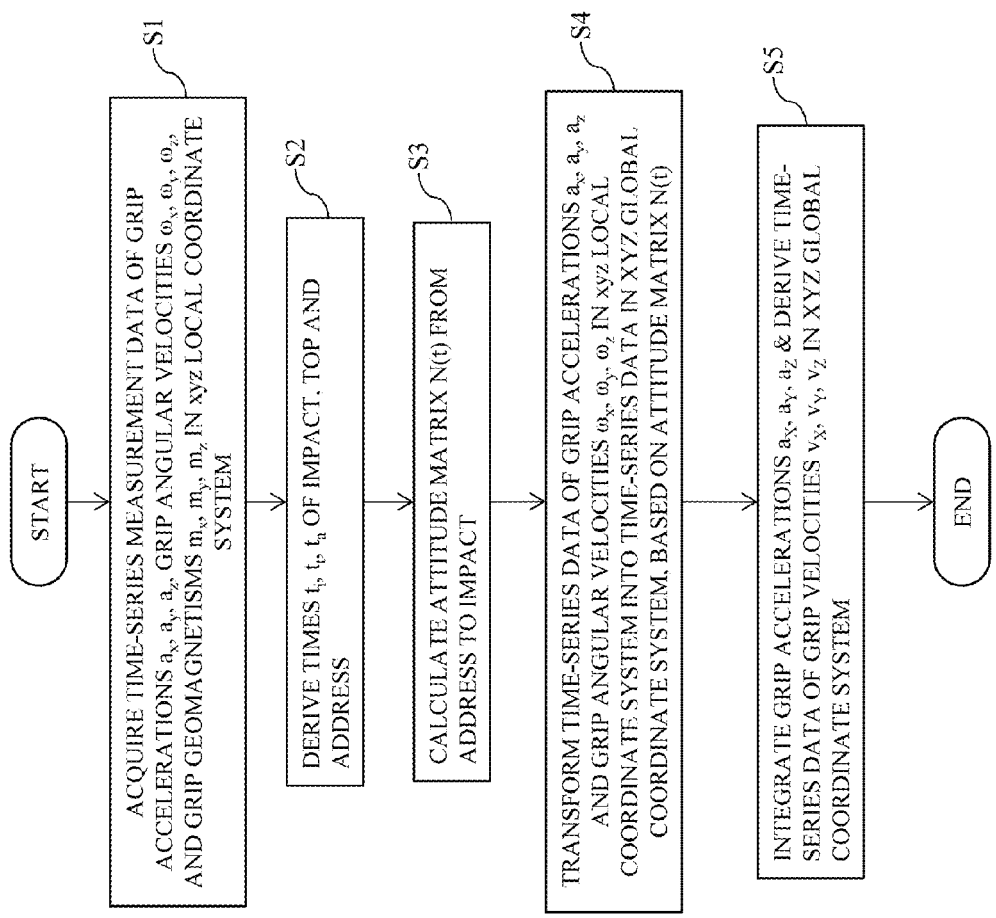
FIG. 5 is a flowchart showing the flow of a first transformation process.

Hereinafter, the first transformation process of transforming the measurement data of the xyz local coordinate system into values of the XYZ global coordinate system will be described, with reference to FIG. 5. Specifically, first, the acquisition unit 24A reads out the time-series measurement data of grip accelerations $a_x$, $a_y$ and $a_z$, grip angular velocities $\omega_x$, $\omega_y$ and $\omega_z$, and grip geomagnetisms $m_x$, $m_y$ and $m_z$ in the xyz local coordinate system that are stored in the storage unit 23 (step S1).

Next, based on the time-series measurement data of the xyz local coordinate system read at step S1, the grip behavior derivation unit 24B derives times $t_i$, $t_t$ and $t_a$ of the impact, top and address (step S2). In the present embodiment, impact time $t_i$ is derived first, top time $t_t$ is derived based on impact time and address time $t_a$ is derived based on top time $t_t$.

Specifically, the time at which an increment per sampling period $\Delta t$ of grip angular velocity $\omega_x$ first exceeds a threshold of 300 deg/s is set as a provisional time of impact. The time at which the increment per sampling period $\Delta t$ of grip angular velocity $\omega_x$ exceeded 200 deg/s during a period until this provisional time of impact from a predetermined amount of time before the provisional time of impact is detected and set as impact time $t_i$.

Figure 6:
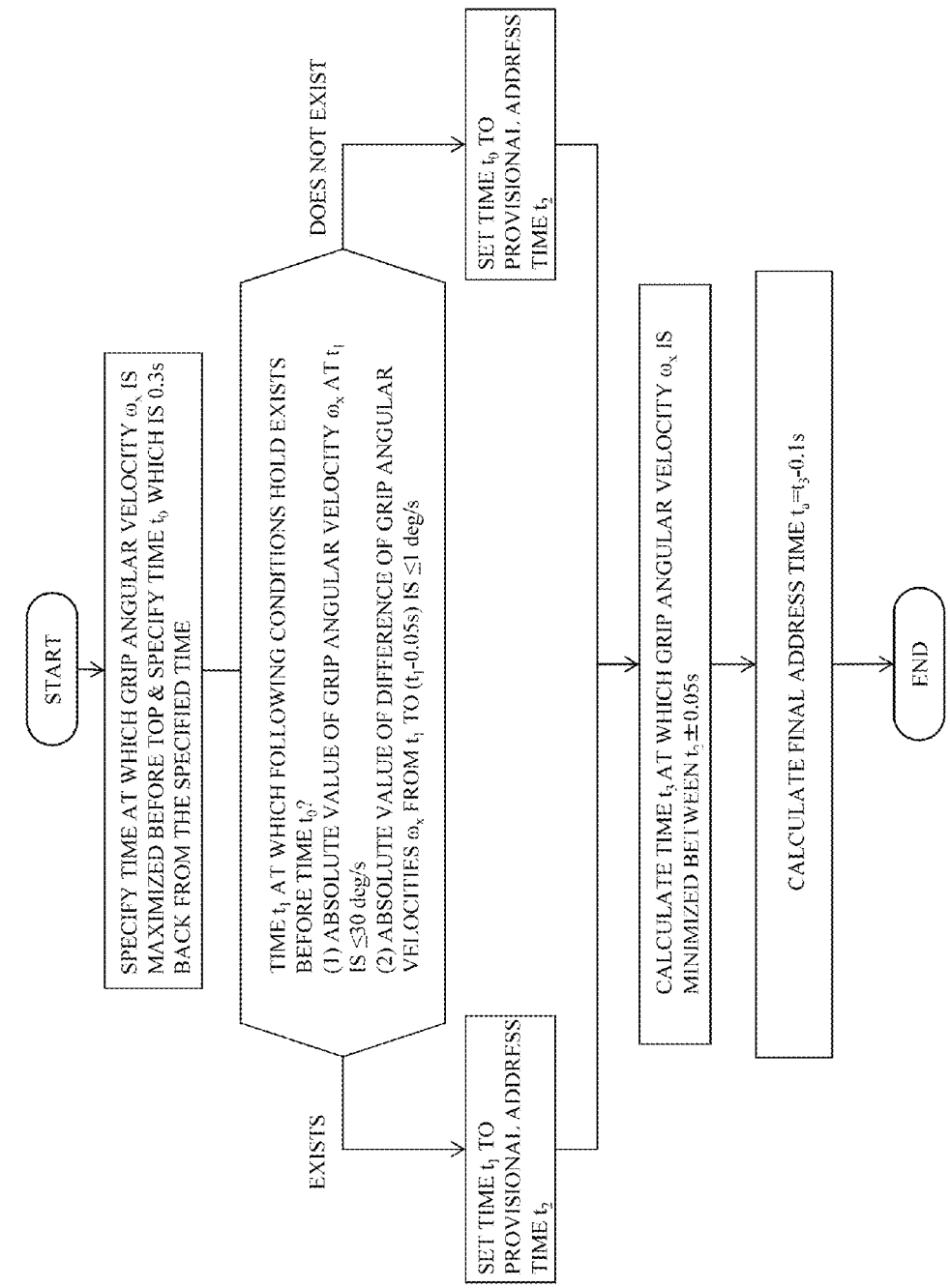
FIG. 6 is a flowchart showing the flow of processing for deriving the time of address.

Next, a time before impact time $t_i$ at which grip angular velocity $\omega_y$ changes from negative to positive is specified as top time $t_t$. Also, address time $t_a$ is calculated in accordance with the flowchart of FIG. 6.

In the following step S3, the grip behavior derivation unit 24B calculates attitude matrix N(t) at time t from address to impact. Here, assume that the attitude matrix is represented by the following equation. Attitude matrix N(t) is for transforming the XYZ global coordinate system at time t into the xyz local coordinate system.

$$N(t) = \begin{pmatrix} a & b & c \\ d & e & f \\ g & h & i \end{pmatrix}^T \qquad \text{Equation 1}$$

The nine components of attitude matrix N(t) are as follows:

Component a: the cosine of the angle formed by the X-axis of the global coordinate system and the x-axis of the local coordinate system Component b: the cosine of the angle formed by the Y-axis of the global coordinate system and the x-axis of the local coordinate system Component c: the cosine of the angle formed by the Z-axis of the global coordinate system and the x-axis of the local coordinate system Component d: the cosine of the angle formed by the X-axis of the global coordinate system and the y-axis of the local coordinate system Component e: the cosine of the angle formed by the Y-axis of the global coordinate system and the y-axis of the local coordinate system Component f: the cosine of the angle formed by the Z-axis of the global coordinate system and the y-axis of the local coordinate system Component g: the cosine of the angle formed by the X-axis of the global coordinate system and the z-axis of the local coordinate system Component h: the cosine of the angle formed by the Y-axis of the global coordinate system and the z-axis of the local coordinate system Component i: the cosine of the angle formed by the Z-axis of the global coordinate system and the z-axis of the local coordinate system Here, a vector (a, b, c) represents the unit vector of the x-axis direction, a vector (d, e, f) represents the unit vector of the y-axis direction, and a vector (g, h, i) represents the unit vector of the z-axis direction.

Also, attitude matrix N(t) can be represented by the following equation in accordance with the thinking of the Z-Y-Z system of Euler angles. Note that $\varphi$, $\theta$ and $\psi$ are the angles of rotation about the Z-axis, the Y-axis, and the Z-axis.

$$N(t) = \begin{bmatrix} \cos\phi\cos\theta\cos\varphi - \sin\phi\sin\varphi & -\cos\phi\cos\theta\sin\varphi - \sin\phi\cos\varphi & \cos\phi\sin\theta \\ \sin\phi\cos\theta\cos\varphi + \cos\phi\sin\varphi & -\sin\phi\cos\theta\sin\varphi + \cos\phi\cos\varphi & \sin\phi\sin\theta \\ -\sin\theta\cos\varphi & \sin\theta\sin\varphi & \cos\theta \end{bmatrix}$$

Equation 2

In calculating attitude matrix N(t) from address to impact, first attitude matrix $N(t_a)$ at address time $t_a$ is calculated. Specifically, $\varphi$ and $\theta$ at the time of address are calculated, in accordance with the following equations. Note that the following equations utilize the fact that, at the time of address, the golf club 4 is stationary and only gravity in the vertical direction is detected by the acceleration sensor 11. Grip accelerations $a_x$, $a_y$ and $a_z$ in the following equations are values at the time of address.

$$\phi = \tan^{-1}\left(\frac{a_y}{a_x}\right)$$

Equation 3

$$\theta = \tan^{-1}\left(\frac{\sqrt{a_x^2 + a_y^2}}{a_z}\right)$$

Equation 4

Next, $\psi$ at the time of address is calculated in accordance with the following equation.

$$\varphi = \tan^{-1}\left(\frac{-m_{yi}}{m_{xi}}\right)$$

Equation 5

Note that the values of $m_{xi}$ and $m_{yi}$ in the above equation are calculated in accordance with the following equation. Also, grip geomagnetisms $m_x$, $m_y$ and $m_z$ in the following equation are values at the time of address.

$$\begin{bmatrix} m_{xi} \\ m_{yi} \\ m_{zi} \end{bmatrix} = \begin{bmatrix} \cos\theta\cos\phi & -\cos\theta\sin\phi & \sin\theta \\ \sin\phi & \cos\phi & 0 \\ -\sin\theta\cos\phi & \sin\theta\sin\phi & \cos\theta \end{bmatrix} \begin{bmatrix} m_x \\ m_y \\ m_z \end{bmatrix}$$

Equation 6

As described above, $\varphi$, $\theta$ and $\psi$ at the time of address are calculated based on grip accelerations $a_x$, $a_y$ and $a_z$, and grip geomagnetisms $m_x$, $m_y$ and $m_z$ in the xyz local coordinate system. Attitude matrix $N(t_a)$ at the time of address is calculated by substituting the values of $\varphi$, $\theta$ and $\psi$ into equation 2.

Next, attitude matrix N(t) from address to impact is calculated by updating attitude matrix $N(t_a)$ at the time of address momentarily at intervals of sampling period $\Delta t$. In specific terms, first, attitude matrix N(t) is represented by the following equation, using the four variables $q_1$, $q_2$, $q_3$ and $q_4$ ($q_4$ being the scalar part) of a quaternion.

$$N(t) = \begin{pmatrix} q_1^2 - q_2^2 - q_3^2 + q_4^2 & 2(q_3q_4 + q_1q_2) & 2(q_1q_3 - q_2q_4) \\ 2(q_1q_2 - q_3q_4) & -q_1^2 + q_2^2 - q_3^2 + q_4^2 & 2(q_1q_4 + q_2q_3) \\ 2(q_2q_4 + q_1q_3) & 2(q_2q_3 - q_1q_4) & -q_1^2 - q_2^2 + q_3^2 + q_4^2 \end{pmatrix}$$

Equation 7

Accordingly, the four variables q1, q2, q3 and q4 of the quaternion can be calculated from equation 1 and equation 7, in accordance with the following equation.

$$q_4 = \pm\frac{1}{2}\sqrt{1 + a + e + i}$$

$$q_1 = (h - f)/4q_4$$

$$q_2 = (c - g)/4q_4$$

$$q_3 = (d - b)/4q_4$$

Equation 8

Here, the values of a to i defining attitude matrix $N(t_a)$ at the time of address are known. Therefore, first, the four variables q1, q2, q3 and q4 of the quaternion at the time of address are calculated, in accordance with the above equation.

Quaternion q' after a short amount of time has elapsed from time t is then represented by the following equation using quaternion q at time t.

$$q' = qdq$$

$$dq = \int \frac{d}{dt}q\,dt$$

Equation 9

Also, a first order differential equation representing the time variation of the four variables q1, q2, q3 and q4 of the quaternion is represented by the following equation.

$$\frac{d}{dt}\begin{pmatrix} q_1 \\ q_2 \\ q_3 \\ q_4 \end{pmatrix} = \begin{pmatrix} 0 & \omega_z & -\omega_y & \omega_x \\ -\omega_z & 0 & \omega_x & \omega_y \\ \omega_y & -\omega_x & 0 & \omega_z \\ -\omega_x & -\omega_y & -\omega_z & 0 \end{pmatrix}\begin{pmatrix} q_1 \\ q_2 \\ q_3 \\ q_4 \end{pmatrix} \quad \text{Equation 10}$$

The quaternion at time t can be sequentially updated to a quaternion at the following time t+Δt by using equations 9 and 10. Here, the quaternions from address to impact are calculated. Attitude matrix N(t) from address to impact is calculated by sequentially substituting the four variables q1, q2, q3 and q4 of the quaternions from address to impact into equation 7.

Next, at step S4, the grip behavior derivation unit 24B transforms the time-series data of grip accelerations $a_x$, $a_y$ and $a_z$ and grip angular velocities $\omega_x$, $\omega_y$ and $\omega_z$ in the xyz local coordinate system from address to impact into time-series data in the XYZ global coordinate system, based on attitude matrix N(t) from address to impact. Grip accelerations $a_X$, $a_Y$ and $a_Z$ and grip angular velocities $\omega_X$, $\omega_Y$, and $\omega_Z$ after transformation are calculated in accordance with the following equation.

$$(a_X a_Y a_Z)^T = [N(t)]^T (a_x a_y a_z)^T$$

$$(\omega_X \omega_Y \omega_Z)^T = [N(t)]^T (\omega_x \omega_y \omega_z)^T \quad \text{Equation 11}$$

In the following step S5, the grip behavior derivation unit 24B derives grip velocities $v_X$, $v_Y$ and $v_Z$ in the XYZ global coordinate system from address to impact, by integrating the time-series data of grip accelerations $a_X$, $a_Y$ and $a_Z$. At this time, offsetting is preferably performed so that grip velocities $v_X$, $v_Y$ and $v_Z$ from address to impact will be 0 m/s at the top. For example, the offsetting at an arbitrary time t is performed by subtracting (grip velocities $v_X$, $v_Y$ and $v_Z$ at top time $t_t$)×t/($t_t$−$t_a$) from grip velocities $v_X$, $v_Y$ and $v_Z$ at time t.

1-2-3. Second Transformation Process

Figure 7:
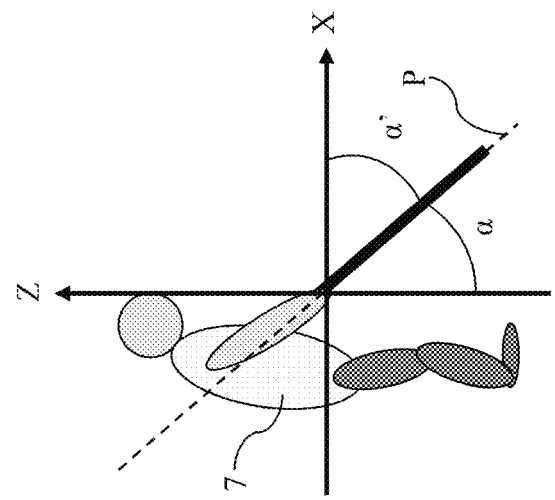
FIG. 7 is a diagram illustrating a swing plane.
Figure 7:
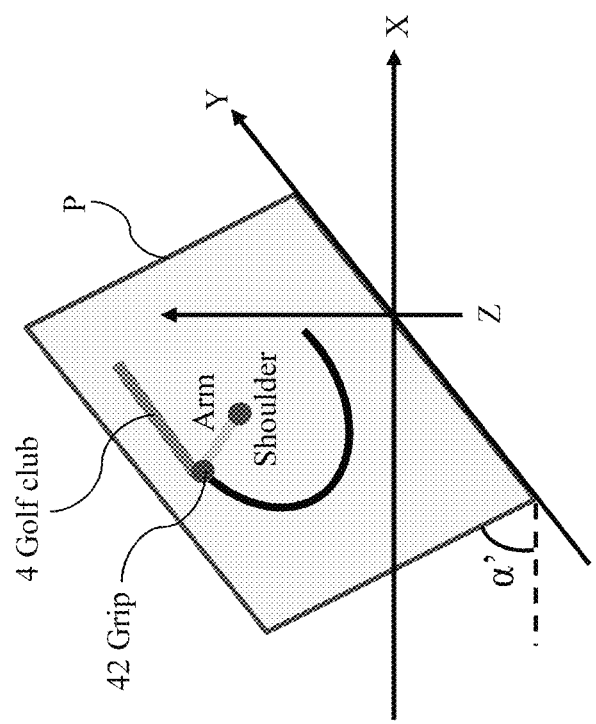

Hereinafter, the second transformation process of transforming the behavior of the grip 42 in the XYZ global coordinate system calculated in the first transformation process into the behavior of the grip 42 in swing plane P will be described. In the present embodiment, swing plane P is defined as a plane that includes the origin of the XYZ global coordinate system and is parallel to the Y-axis and the shaft 40 of the golf club 4 at the time of impact (see FIG. 7). In the second transformation process, the grip behavior derivation unit 24B calculates grip velocities $v_{pX}$, $v_{pY}$ and $v_{pZ}$ and grip angular velocities $\omega_{pX}$, $\omega_{pY}$, and $\omega_{pZ}$ obtained by projecting grip velocities $v_X$, $v_Y$ and $v_Z$ and grip angular velocities $\omega_X$, $\omega_Y$ and $\omega_Z$ in the XYZ global coordinate system onto swing plane P.

Specifically, time-series data of the slope of the shaft 40 as viewed from the X-axis positive direction (the golfer 7 as viewed from the front) is calculated, based on the z-axis vector (g, h, i) that is included in attitude matrix N(t) and represents the direction in which the shaft 40 extends. The time at which the shaft 40 becomes parallel to the Z-axis as viewed from the X-axis positive direction is then specified based on this time-series data, and the specified time is set as impact time $t_i$. Note that impact time $t_i$ referred to here does not necessarily coincide with the aforementioned impact time $t_i$. Next, the slope of the shaft 40 as viewed from the Y-axis negative direction is calculated, based on the z-axis vector (g, h, i) that is included in attitude matrix $N(t_i)$ at this impact time $t_i$. That is, angle α' that is formed by the shaft 40 and the X-axis as viewed from Y-axis negative direction at the time of impact is calculated, and the calculated angle α' is set as the swing plane angle.

When swing plane angle α' has been derived, a projective transformation matrix A for projecting an arbitrary point in the XYZ global coordinate system onto swing plane P using the derived swing plane angle α' can be calculated as follows. Note that α=90°−α'.

$$A = \begin{bmatrix} \cos\alpha & 0 & \sin\alpha \\ 0 & 1 & 0 \\ -\sin\alpha & 0 & \cos\alpha \end{bmatrix} \quad \text{Equation 12}$$

Here, the time-series data of grip velocities $v_{pX}$, $v_{pY}$ and $v_{pZ}$ and grip angular velocities $\omega_{pX}$, $\omega_{pY}$ and $\omega_{pZ}$ after projective transformation from address to impact are calculated, in accordance with the following equation, based on the above projective transformation matrix A.

$$\begin{bmatrix} v_{pX} \\ v_{pY} \\ v_{pZ} \end{bmatrix} = \begin{bmatrix} \cos\alpha & 0 & \sin\alpha \\ 0 & 1 & 0 \\ -\sin\alpha & 0 & \cos\alpha \end{bmatrix} \quad \text{Equation 13}$$

$$\begin{bmatrix} v_X \\ v_Y \\ v_Z \end{bmatrix} = \begin{bmatrix} \cos\alpha \cdot v_X + \sin\alpha \cdot v_Z \\ v_Y \\ -\sin\alpha \cdot v_X + \cos\alpha \cdot v_Z \end{bmatrix}$$

$$\begin{bmatrix} \omega_{pX} \\ \omega_{pY} \\ \omega_{pZ} \end{bmatrix} = \begin{bmatrix} \cos\alpha & 0 & \sin\alpha \\ 0 & 1 & 0 \\ -\sin\alpha & 0 & \cos\alpha \end{bmatrix}$$

$$\begin{bmatrix} \omega_X \\ \omega_Y \\ \omega_Z \end{bmatrix} = \begin{bmatrix} \cos\alpha \cdot \omega_X + \sin\alpha \cdot \omega_Z \\ \omega_Y \\ -\sin\alpha \cdot \omega_X + \cos\alpha \cdot \omega_Z \end{bmatrix}$$

Note that the grip velocities ($v_{pY}$, $v_{pZ}$) that are obtained by the above operations represent the grip velocities (vectors) in swing plane P, and grip angular velocity $\omega_{pX}$ represents the angular velocity about the axis perpendicular to swing plane P. Here, the grip velocity (scalar) in swing plane P from address to impact is calculated in accordance with the following equation.

$$V_{GE} = \sqrt{(v_{pY})^2 + (v_{pZ})^2} \quad \text{Equation 14}$$

Also, here, the slope of the shaft 40 at the top in swing plane P, which is required in subsequent calculations, is also calculated. Specifically, first, the z-axis vector (g, h, i) that is included in attitude matrix $N(t_t)$ at the top is projected onto swing plane P in accordance with the following equation, using the projective transformation matrix A. Note that the vector after projection is given as (g', h', i').

$$\begin{bmatrix} g' \\ h' \\ i' \end{bmatrix} = \begin{bmatrix} \cos\alpha & 0 & \sin\alpha \\ 0 & 1 & 0 \\ -\sin\alpha & 0 & \cos\alpha \end{bmatrix} \begin{bmatrix} g \\ h \\ i \end{bmatrix} = \begin{bmatrix} \cos\alpha \cdot g + \sin\alpha \cdot i \\ h \\ -\sin\alpha \cdot g + \cos\alpha \cdot i \end{bmatrix} \quad \text{Equation 15}$$

The vector (h', i') that is specified by the above equation is a vector representing the slope of the shaft 40 at the top in swing plane P. Accordingly, the slope β of the shaft 40 at the top in swing plane P is calculated by substituting the above calculation results into the following equation.

$$\beta = \tan^{-1}\frac{i'}{h'} = \tan^{-1}\frac{-\sin\alpha \cdot g + \cos\alpha \cdot i}{h} \quad \text{Equation 16}$$

1-2-4. Shoulder Behavior Derivation Process

Figure 8:
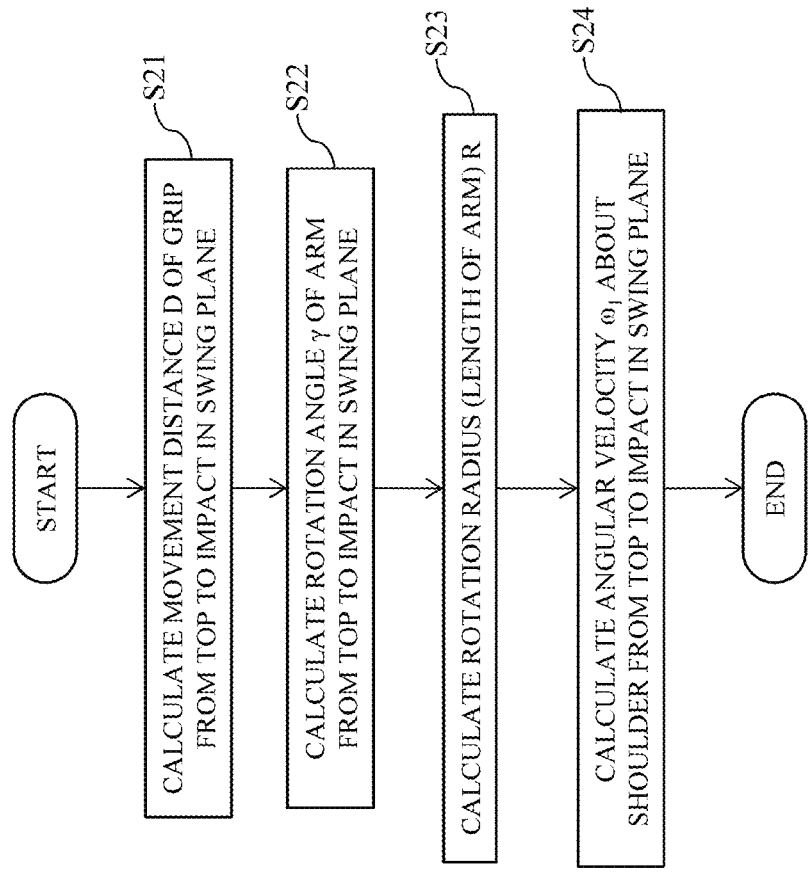
FIG. 8 is a flowchart showing the flow of a shoulder behavior derivation process.

Hereinafter, the shoulder behavior derivation process of deriving the behavior of a pseudo shoulder in swing plane P based on the behavior of the grip (grip velocity $V_{GE}$ and grip angular velocity $\omega_{pX}$) in swing plane P will be described, with reference to FIG. 8. In the present embodiment, the behavior of the golf club 4 is analyzed based on a double pendulum model that takes the shoulder of the golfer 7 and the grip 42 (or the wrist of the golfer holding the grip 42) as nodes, and takes the arm of the golfer 7 and the golf club 4 as links. Note that the behavior of the shoulder is derived as the behavior of the pseudo shoulder, based on the measured behavior of the grip, rather than by directly measuring the behavior of the shoulder. Hereinafter, unless stated otherwise, any reference to merely the "shoulder" is assumed to mean the pseudo shoulder. The same applies to a pseudo "arm", which are defined as extending linearly between the pseudo shoulder and the grip 42 (wrist).

Figure 9:
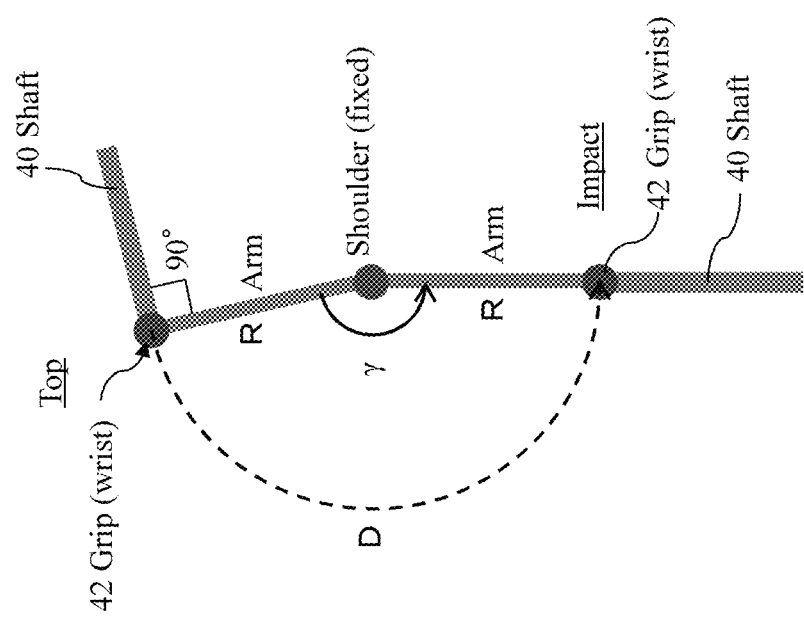
FIG. 9 is a diagram conceptually illustrating a double pendulum model.

In specifying the behavior of the shoulder from the behavior of the grip, the double pendulum model according to the present embodiment is premised on the following (1) to (5). FIG. 9 is a diagram conceptually illustrating the following preconditions.

(1) In swing plane P, the grip 42 (wrist) circulates about the shoulder.
(2) In swing plane P, a distance (radius) R between the shoulder and the grip 42 is constant.
(3) The shoulder (rotates but) does not move during the swing action.
(4) In swing plane P, the angle formed by the arm at the top and the golf club 4 is 90 degrees.
(5) The arm at the time of impact faces down in the z-axis direction as viewed from for X-axis positive direction.

Under the above premises, the shoulder behavior derivation unit 24C calculates movement distance D of the grip 42 from top to impact in swing plane P (step S21). Movement distance D is derived by integrating grip velocity $V_{GE}$ from top to impact.

Next, the shoulder behavior derivation unit 24C calculates rotation angle γ of the arm from top to impact in swing plane P (step S22). Rotation angle γ is calculated based on the slope β of the shaft 40 at the top calculated in the second transformation process. Next, the shoulder behavior derivation unit 24C calculates radius R=D/γ (step S23).

The shoulder behavior derivation unit 24C then calculates the angular velocity (angular velocity of the arm) $\omega_1$ about the shoulder from top to impact in swing plane P as the behavior of the shoulder, in accordance with the following equation (step S24). That is, angular velocity $\omega_1$ of the arm will be a value that reflects the measured grip velocity $V_{GE}$.

$$\omega_1 = V_{GE}/R$$

1-2-5. Index Calculation Process

Figure 10:
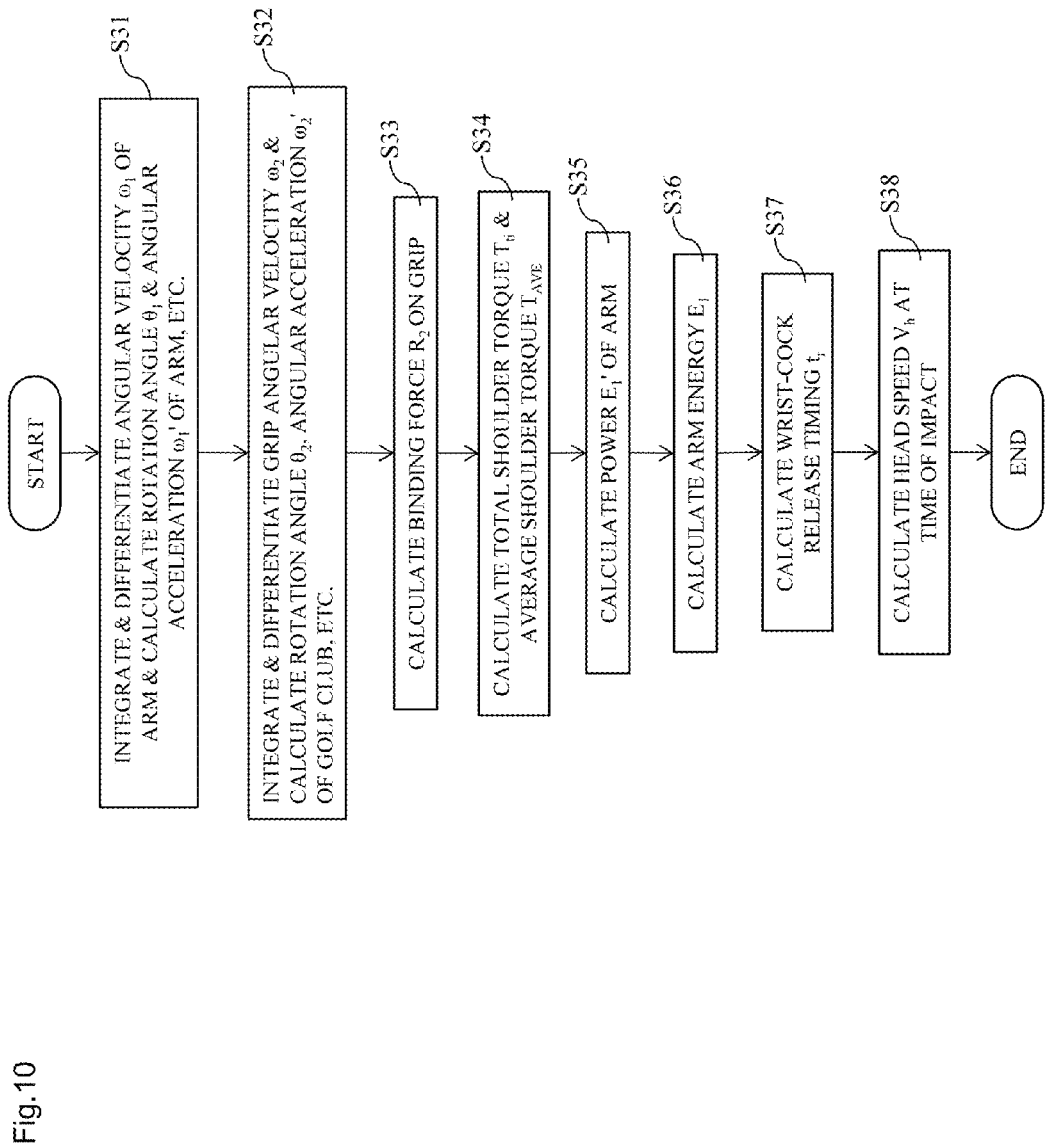
FIG. 10 is a flowchart showing the flow of an index calculation process.

Hereinafter, the index calculation process of calculating swing indices for determining the optimal club weight based on the behavior of the grip 42 and the behavior of the shoulder will be described, with reference to FIG. 10. In the present embodiment, average shoulder torque $T_{AVE}$, arm energy $E_{AVE}$ and head speed $V_h$ which will be discussed later are calculated as swing indices.

Figure 11:
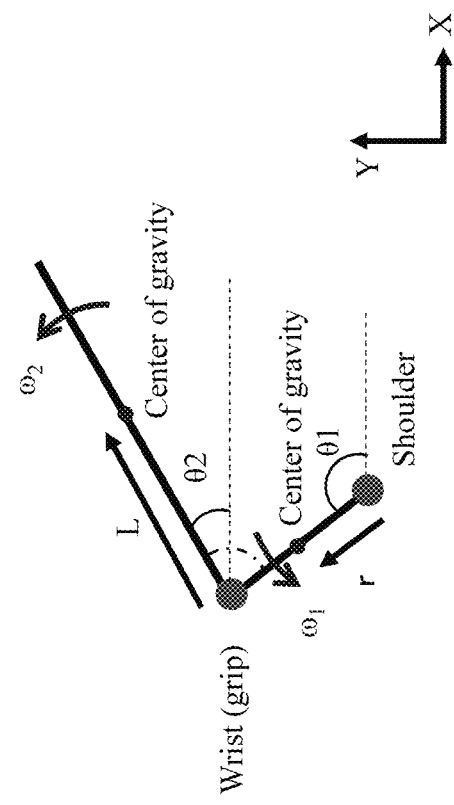
FIG. 11 is another diagram conceptually illustrating a double pendulum model.

Specifically, first, at step S31, the shoulder behavior derivation unit 24C integrates angular velocity $\omega_1$ of the arm from top to impact, and calculates rotation angles $\theta_1$ of the arm from top to impact. At this time, trapezoidal integration is preferably used. Note that rotation angle $\theta_1$ is defined as shown in FIG. 11, and the plane in FIG. 11 is equal to swing plane P. Hereinafter, analysis proceeds based on the new XY coordinate system in swing plane P shown in FIG. 11. The X-axis of the new XY coordinate system in swing plane P is equal to the Y-axis of the abovementioned XYZ global coordinate system, and the Y-axis of the new XY coordinate system is an axis that results from the Z-axis of the XYZ coordinate system being projected in swing plane P.

Also, the shoulder behavior derivation unit 24C differentiates angular velocity $\omega_1$ of the arm from top to impact, and calculates the angular acceleration $\omega_1'$ from top to impact. Next, the shoulder behavior derivation unit 24C calculates the position $(X_1, Y_1)$, the velocity $(V_{X1}, V_{Y1})$ and the acceleration $(A_{X1}, A_{Y1})$ of the center of gravity of the arm from top to impact. These values are calculated by substituting the above mentioned calculation results into the following equation.

$$X_1 = r\cos\theta_1$$

$$Y_1 = r\sin\theta_1$$

$$V_{X1} = -r\omega_1\sin\theta_1$$

$$V_{Y1} = r\omega_1\cos\theta_1$$

$$A_{X1} = -r\omega_1'\sin\theta_1 - r\omega_1^2\cos\theta_1$$

$$A_{Y1} = -r\omega_1'\cos\theta_1 - r\omega_1^2\sin\theta_1 \quad \text{Equation 17}$$

Note that r is the distance from the shoulder to the center of gravity of the arm. In the present embodiment, the center of gravity of the arm is assumed to be in the center of the arm. Accordingly, R=2r.

Next, at step S32, the grip behavior derivation unit 24B also performs a similar operation to step S31 with respect to the area around the grip 42. That is, angular velocity $\omega_2$ of the golf club 4 about the grip 42 from top to impact (=grip angular velocity $\omega_{pX}$ from top to impact) is integrated, and a rotation angle $\theta_2$ of the golf club 4 (shaft 40) about the grip 42 from top to impact is calculated. Trapezoidal integration is also preferably used at this time, and the rotation angle $\theta_2$ is defined as shown in FIG. 11.

Next, the grip behavior derivation unit 24B differentiates angular velocity $\omega_2$ of the golf club 4 from top to impact, and calculates angular acceleration $\omega_2'$ from top to impact. Next, the grip behavior derivation unit 24B calculates the position $(X_2, Y_2)$, the speed $(V_{X2}, V_{Y2})$ and the acceleration $(A_{X2}, A_{Y2})$ of the center of gravity of the golf club 4 from top to impact. These values are calculated by substituting the abovementioned calculation results into the following equation.

$$X_2 = 2X_1 + L\cos\theta_2$$

$$Y_2 = 2Y_1 + L\sin\theta_2$$

$$V_{X2} = 2V_{X1} - L\omega_2\sin\theta_2$$

$$V_{Y2} = 2V_{Y1} - L\omega_2\cos\theta_2$$

$$A_{X2}=2A_{X1}-L\omega_2' \sin\theta_2 - L\omega_2^2 \cos\theta_2$$

$$A_{Y2}=2A_{Y1}-L\omega_2' \cos\theta_2 - L\omega_2^2 \sin\theta_2 \quad \text{Equation 18}$$

Note that L is the distance from the grip 42 to the center of gravity of the golf club 4. The value of L is a specification of the golf club 4, and is assumed to be determined in advance.

Next, in step S33, the index calculation unit 24D calculates binding force $R_2$ on the grip 42 from top to impact= $(R_{X2}, R_{Y2})$, by substituting the abovementioned calculation results into the following equation. The following equation is based on balancing translational forces. Note that $m_2$ is the mass of the golf club, and g is the gravitational acceleration. Also, $m_2$ is a specification of the golf club 4, and is assumed to be determined in advance.

$$R_{X2}=-m_2 A_{X2}$$

$$R_{Y2}=-m_2 A_{Y2}-m_2 g \sin\alpha \quad \text{Equation 19}$$

In the following step S34, the index calculation unit 24D calculates torque $T_1$ about the shoulder and torque $T_2$ about the grip 42 from top to impact, by substituting the abovementioned calculation results into the following equations.

$$T_1 = I_1\omega_1' + 2r\sin\theta_1 \cdot R_{X2} - 2r\cos\theta_1 \cdot R_{Y2} +$$
$$m_1 r\cos\theta_1 \cdot A_{Y1} - m_1 r\sin\theta_1 \cdot A_{X1} + m_1 r\cos\theta_1 \cdot g\sin\alpha + T_2 \quad \text{Equation 20}$$

$$T_2 = I_2\omega_2' + m_2 L \cos\theta_2 \cdot A_{Y2} - m_2 L \sin\theta_2 \cdot A_{X2} + m_2 L \cos\theta_2 \cdot g \sin\alpha \quad \text{Equation 21}$$

Note that $I_1$ is the moment of inertia about the center of gravity of the arm, and $I_2$ is the moment of inertia about the center of gravity of the golf club 4. In the present embodiment, moment of inertia $I_1$ about the center of gravity of the arm is calculated as $I_1=m_1 r^2/3$, assuming the center of gravity of the arm is in the center of the arm. $m_1$ is the mass of the arm, and, in the present embodiment, the mass $m_1$ of the arm is assumed to be determined in advance as appropriate. For example, before starting analysis, the weight of the golfer 7 is input, and the mass of the arm is automatically calculated by an operation such as multiplying the input weight by a predetermined coefficient. Also, $I_2$ is a specification of the golf club 4, and is assumed to be determined in advance.

In the present embodiment, the index calculation unit 24D calculates value $T_{ti}$ obtained by integrating torque $T_1$ about the shoulder for the segment from top to impact. $T_{ti}$ is the total amount of torque exerted about the shoulder of the golfer 7 from top to impact (hereinafter, total shoulder torque), and in this sense is an index representing the torque about the shoulder during the swing action. Also, the index calculation unit 24D calculates $T_{AVE}=T_{ti}/t_i-t_c$, which is the average torque about the shoulder during the swing action obtained by dividing torque $T_{ti}$ by the time from top to impact (hereinafter, average shoulder torque). Average shoulder torque $T_{AVE}$ also serves as an index representing the torque about the shoulder during the swing action, and is one of the swing indices. Note that in calculating total shoulder torque $T_{ti}$, a configuration may be adopted in which only positive torque $T_1$ is integrated or in which the average value of torque $T_1$ is integrated.

In the following step S35, the index calculation unit 24D calculates arm power $E_1'$ from top to impact based on the abovementioned calculation results. Specifically, E1' is represented in accordance with the following equation, where $v_s$ is the velocity vector of the shoulder and $v_g$ is the velocity vector of the grip 42. Note that $R_1$ is the binding force on the shoulder. Also, $v_s$ and $v_g$ can respectively be calculated by differentiating position vector $d_s$ of the shoulder and position vector $d_g$ of the grip 42=$d_s+(2X_1, 2Y_1)$.

$$E_1'=-R_1 v_s^T + R_2 v_g^T + T_1\omega_1 - T_2\omega_1 \quad \text{Equation 22}$$

Also, in the present embodiment, $v_s=(0, 0)$ since the shoulder does not move, and arm power $E_1'$ is calculated in accordance with the following equation. The index calculation unit 24D calculates arm power $E_1'$ from top to impact by substituting the abovementioned calculation results into the following equation.

$$E_1' R_2 v_g^T + T_1\omega_1 - T_2\omega_1 \quad \text{Equation 23}$$

Figure 12:
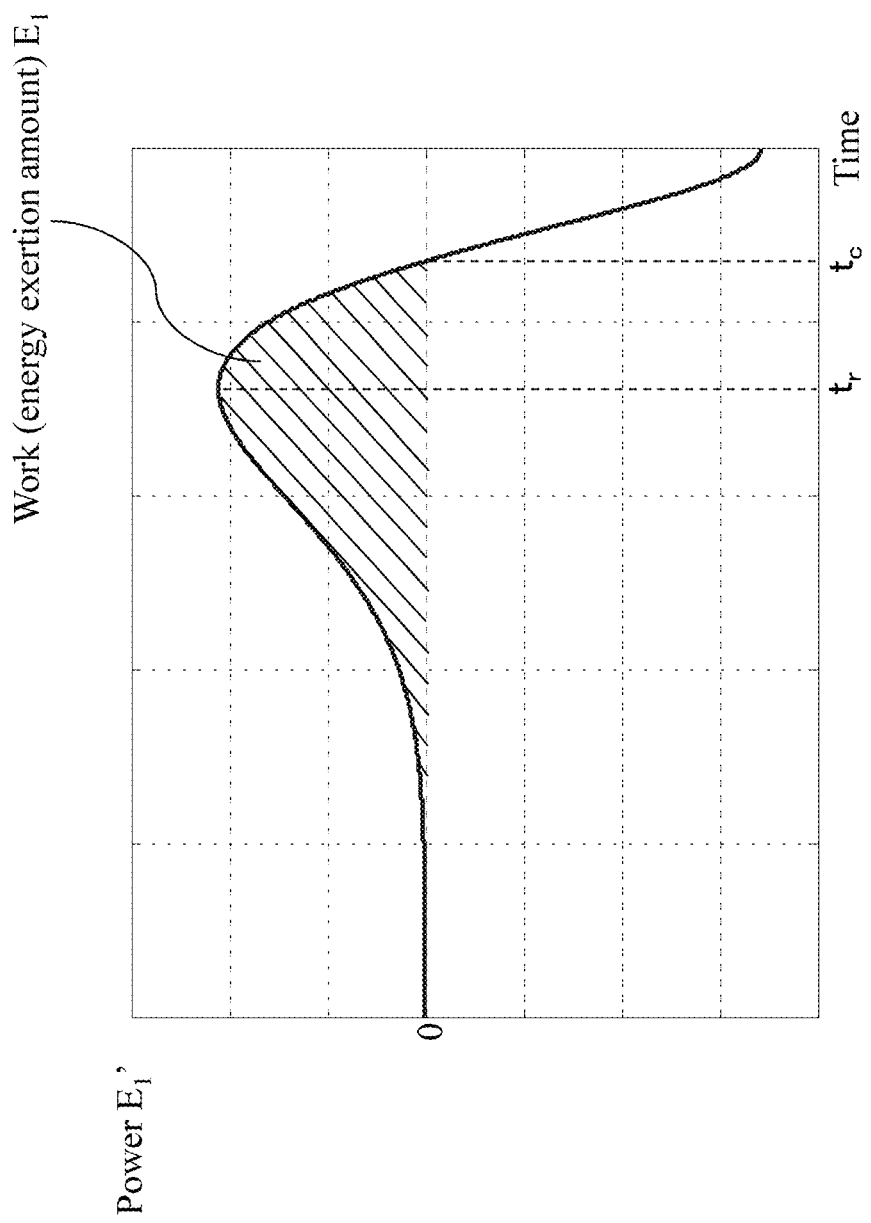
FIG. 12 is a diagram illustrating arm energy which is one swing index.

In the following step S36, the index calculation unit 24D specifies time $t_c$ at which power $E_1'$ of the arm changes from positive to negative after the top, and calculates work $E_1$ of the arm from time $t_t$ to time $t_c$. Work $E_1$ of the arm is calculated by integrating power $E_1'$ of the arm for the segment from time $t_t$ to time $t_c$ (see FIG. 12). Note that work $E_1$ can be taken as an index representing the work (energy) that is exerted by the arm between times $t_t$ and $t_c$, and thus, in this sense, can be called arm energy during the swing action.

In the following step S37, the index calculation unit 24D calculates wrist-cock release timing $t_r$ that occurs during the swing action. Note that the inventors found, through testing, that head speed $V_h$ at the time of the impact, which serves as a swing index, is correlated with wrist-cock release timing $t_r$ during the swing action and arm energy $E_1$ or average power $E_{AVE}=E_1/t_c-t_r$. Average power $E_{AVE}$ is the arm energy exerted or consumed on average per unit time during the swing action. In view of this, here, wrist-cock release timing $t_r$ is calculated in order to calculate head speed $V_h$ at the time of impact. In the present embodiment, with regard to the wrist-cock release timing $t_r$, the time at which arm power $E_1'$ is maximized in the segment from time $t_t$ to time $t_c$ is specified as wrist-cock release timing $t_r$ (see FIG. 12).

In the following step S38, the index calculation unit 24D calculates head speed $V_h$ at the time of impact, based on wrist-cock release timing $t_r$ and arm energy $E_{AVE}$. Specifically, head speed $V_h$ at the time of impact is calculated according to the following equation. Note that $k_1$, $k_2$ and $k_3$ are constants obtained from the results of a large number tests carried out in advance by multiple regression analysis, and are held in advance in the storage unit 23. This ends the index calculation process.

$$V_h = k_1 \cdot E_{AVE} + k_2 \cdot t_r + k_3$$

1-2-6. Optimal Total Weight Determination Process

Figure 13:
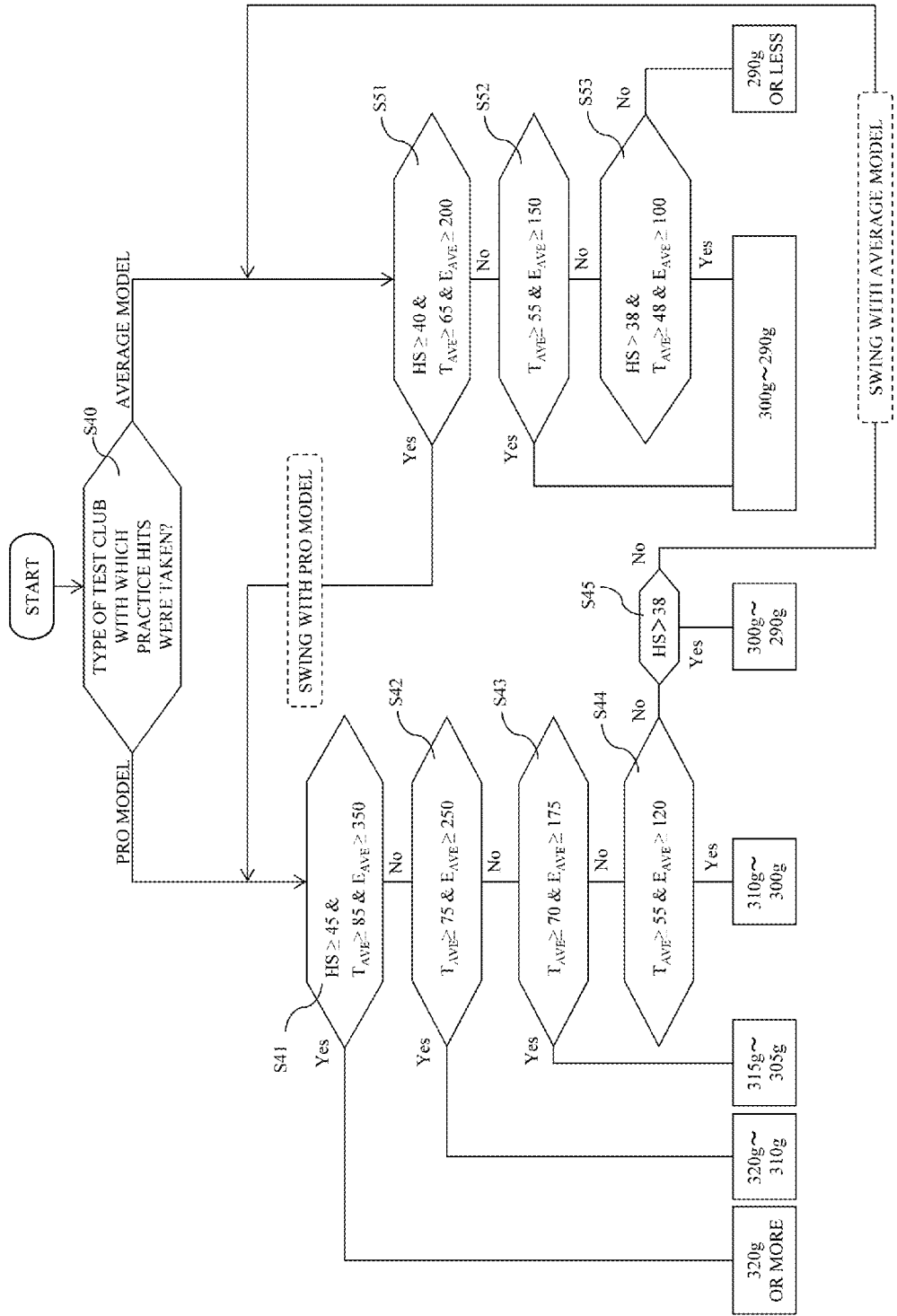
FIG. 13 is a flowchart showing the flow of an optimal total weight determination process.

Hereinafter, the flow of an optimal total weight determination process of determining the optimal club weight will be described, with reference to FIG. 13.

First, in step S40, the determination unit 24E determines the type of test club with which practice hits were taken in the measurement process. If the practice hits were taken with the pro model club, the processing advances to step S41, and if practice hits were taken with the average model club, the processing advances to step S51. Which test club was used to take practice hits with is assumed to be determined based on the information input by the user via the input unit 22.

Figure 14:
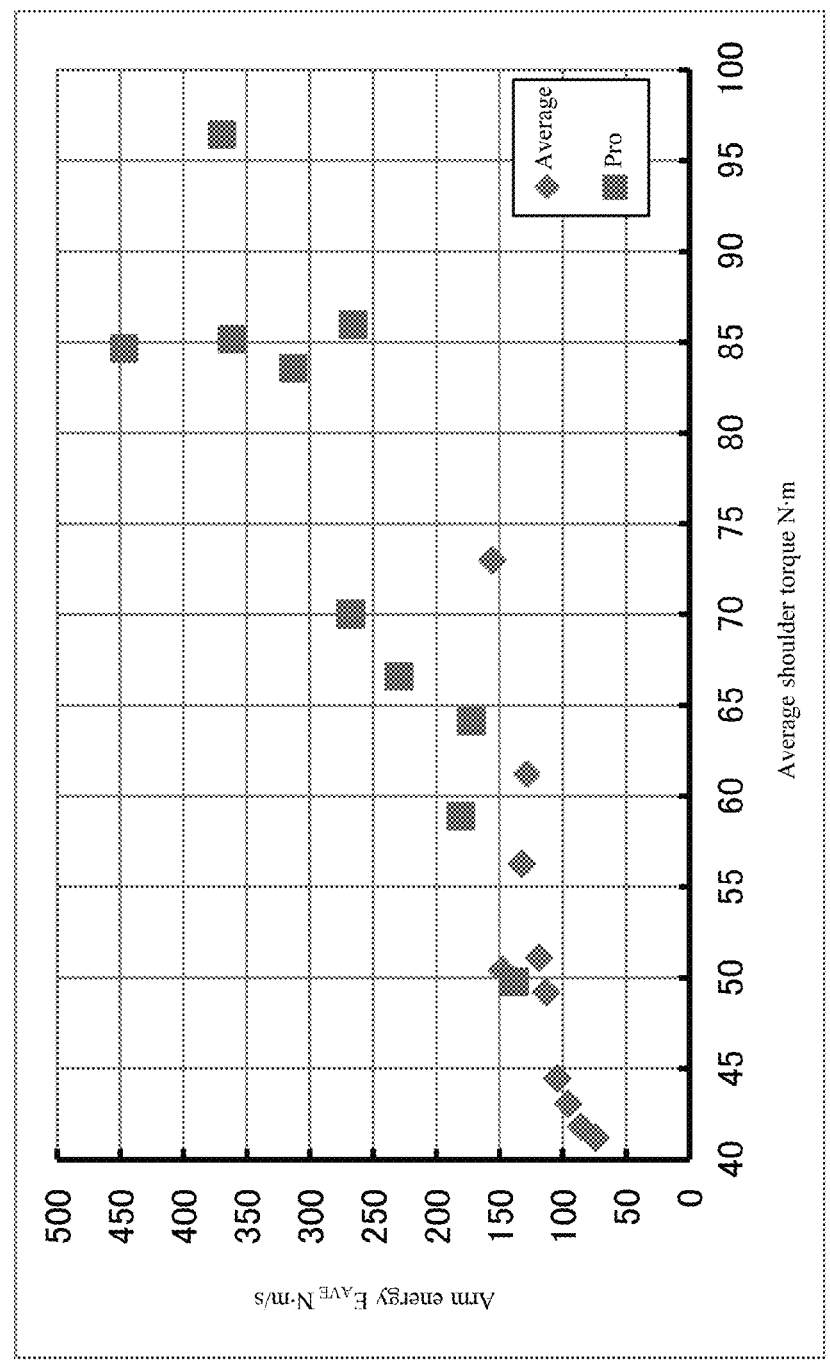
FIG. 14 is a diagram plotting arm energy values and average shoulder torque values during the swing action of ten pro model users and ten average model users.
Figure 15:
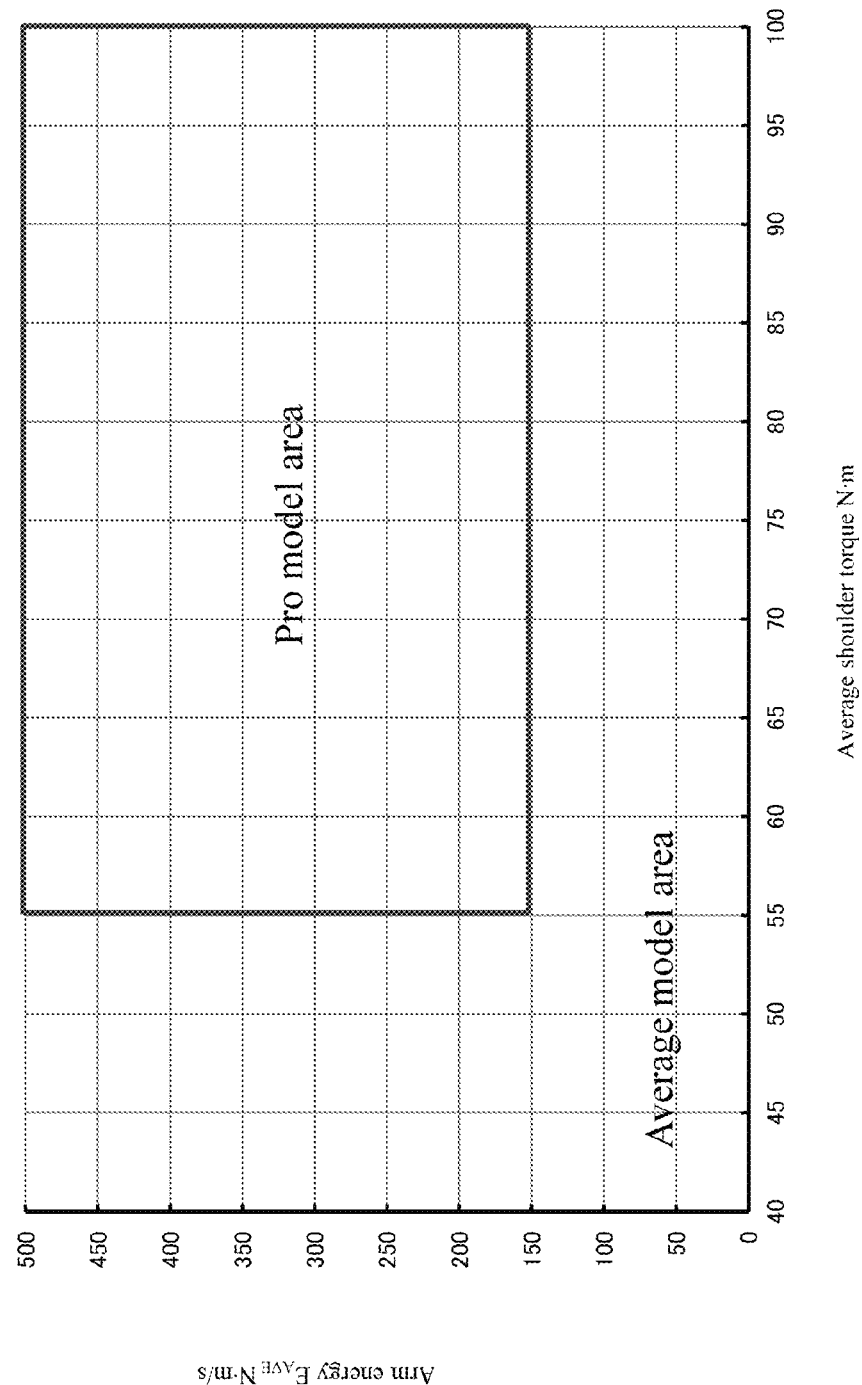
FIG. 15 is a diagram showing a pro model area and an average model area.

Note that the type of test club is determined in step S40 because the area over which the swing indices are distributed differs according to the type of test club. In specific terms, the inventors obtained the results shown in FIG. 14 after getting ten golfers who normally use a pro model club (hereinafter, pro model users) to take practice hits with the pro model club and ten golfers who normally use an average model club (hereinafter, average model users) to take practice hits with the average model club and then calculating swing indices. Note that the swing indices calculated in this testing were average shoulder torque $T_{AVE}$ and arm energy $E_{AVE}$, and the specific values were calculated in accordance with a process similar to the process described above. The inventors then discovered from the result shown in FIG. 14 that the space showing the swing indices was divided into a pro model area and an average model area as shown in FIG. 15. Note that the pro model area is an area in which the swing indices during the swing action of the pro model users are distributed, and the average model area is an area in which the swing indices during the swing action of the average model users are distributed. In the example in FIG. 14, the pro model area is an area in which average shoulder torque $T_{AVE} \geq 55$ N·m and arm energy $E_{AVE} \geq 150$ N·m/s, and the average model area is an area in which average shoulder torque $T_{AVE} < 55$ N·m or arm energy $E_{AVE} < 150$ N·m/s. However, these figures can change depending on swing conditions such as the type of test club. This testing was performed using a SRIXON (registered trademark) Z-525 driver made by Dunlop Sports Co. Ltd. (Miyazaki KENA Blue 6 S-Flex shaft, club weight of 315 g, and swing weight of D2) as the pro model club, and a XXIO (registered trademark) 7 driver made by Dunlop Sports Co. Ltd. (MP-700 R-Flex shaft, club weight of 285 g, and swing weight of D1) as the average model club.

Next, step S41 and steps S42 to S45 following thereon will be described. Steps S41 to S45 are steps for determining the range of optimal club weights (hereinafter, optimal weight zone), according to the magnitudes of average shoulder torque $T_{AVE}$, arm energy $E_{AVE}$, and head speed $V_h$. Here, the optimal weight zone is gradually set to larger values as the values of $T_{AVE}$, $E_{AVE}$ and $V_h$ increase.

Specifically, in step S41, the determination unit 24E determines whether head speed $V_h$ is 45 m/s or more, average shoulder torque $T_{AVE}$ is 85 N·m or more, and arm energy $E_{AVE}$ is 350 N·m/s or more (hereinafter, pro condition 1). If pro condition 1 is satisfied, the determination unit 24E then determines the optimal weight zone to be 320 g or more. On the other hand, when pro condition 1 is not satisfied at step S41, the processing advances to step S42. At step S42, the determination unit 24E determines whether average shoulder torque $T_{AVE}$ is 75 N·m or more and arm energy $E_{AVE}$ is 250 N·m/s or more (hereinafter, pro condition 2). If pro condition 2 is satisfied, the determination unit 24E then determines the optimal weight zone to be 310 g to 320 g. On the other hand, if pro condition 2 is not satisfied at step S42, the processing advances to step S43. At step S43, the determination unit 24E determines whether average shoulder torque $T_{AVE}$ is 70 N·m or more and arm energy $E_{AVE}$ is 175 N·m/s or more (hereinafter, pro condition 3). If pro condition 3 is satisfied, the determination unit 24E then determines the optimal weight zone to be 305 g to 315 g. On the other hand, if pro condition 3 is not satisfied at step S43, the processing advances to step S44. In step S44, the determination unit 24E determines whether average shoulder torque $T_{AVE}$ is 55 N·m or more and arm energy $E_{AVE}$ is 120 N·m/s or more (hereinafter, pro condition 4). If pro condition 4 is satisfied, the determination unit 24E then determines the optimal weight zone to be 300 g to 310 g. On the other hand, if pro condition 4 is not satisfied at step S44, the processing advances to step S45. In step S45, the determination unit 24E determines whether head speed $V_h$ is greater than 38 m/s (hereinafter, pro condition 5). If pro condition 5 is satisfied, the determination unit 24E then determines the optimal weight zone to be 290 g to 300 g. On the other hand, if pro condition 5 is not satisfied at step S45, the determination unit 24E determines the average model club to be more suitable than the pro model club. In response, the display control unit 24F displays a message indicating to redo the fitting from the measurement process using the average model club on the display unit 21, and the processing advances to step S51.

On the other hand, step S51 and steps S52 and S53 following thereon are steps for determining the optimal weight zone, according to the magnitudes of average shoulder torque $T_{AVE}$, arm energy $E_{AVE}$, and head speed $V_h$. Here, the optimal weight zone is gradually set to larger values as the values of $T_{AVE}$, $E_{AVE}$ and $V_h$ increase.

Specifically, the determination unit 24E, in step S51, determines whether head speed $V_h$ is 40 m/s or more, average shoulder torque $T_{AVE}$ is 65 N·m or more, and arm energy $E_{AVE}$ is 200 N·m/s or more (hereinafter, average condition 1). If average condition 1 is satisfied, the determination unit 24E then determines the pro model club to be more suited than the average model club. In response, the display control unit 24F displays a message indicating to redo the fitting from the measurement process using the pro model club on the display unit 21, and the processing advances to step S41. On the other hand, if average condition 1 is not satisfied at step S51, the processing advances to step S52. In step S52, the determination unit 24E determines whether average shoulder torque $T_{AVE}$ is 55 N·m or more and arm energy $E_{AVE}$ is 150 N·m/s or more (hereinafter, average condition 2). If average condition 2 is satisfied, the determination unit 24E then determines the optimal weight zone to be 290 g to 300 g. On the other hand, if average condition 2 is not satisfied at step S52, the processing advances to step S53. In step S53, the determination unit 24E determines whether head speed $V_h$ is greater than 38 m/s, average shoulder torque $T_{AVE}$ is 48 N·m or more, and arm energy $E_{AVE}$ is 100 N·m/s or more (hereinafter, average condition 3). If average condition 3 is satisfied, the determination unit 24E then determines the optimal weight zone to be 290 g to 300 g. On the other hand, if average condition 3 is not satisfied at step S53, the determination unit 24E determines the optimal weight zone to be 290 g or less.

Figure 17:
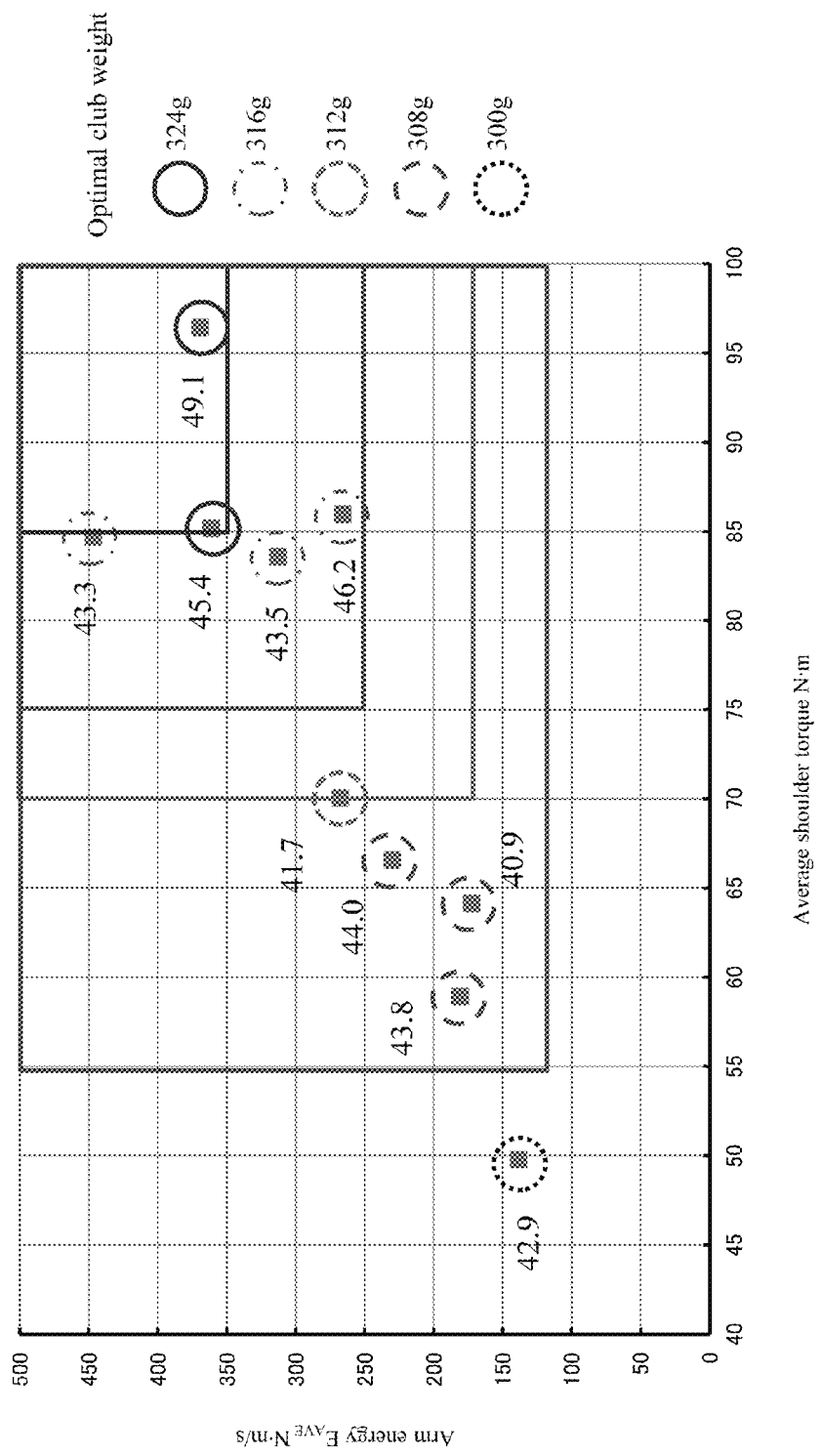
FIG. 17 is a diagram showing head speed and optimal club weight during the swing action of pro model users derived empirically.
Figure 18:
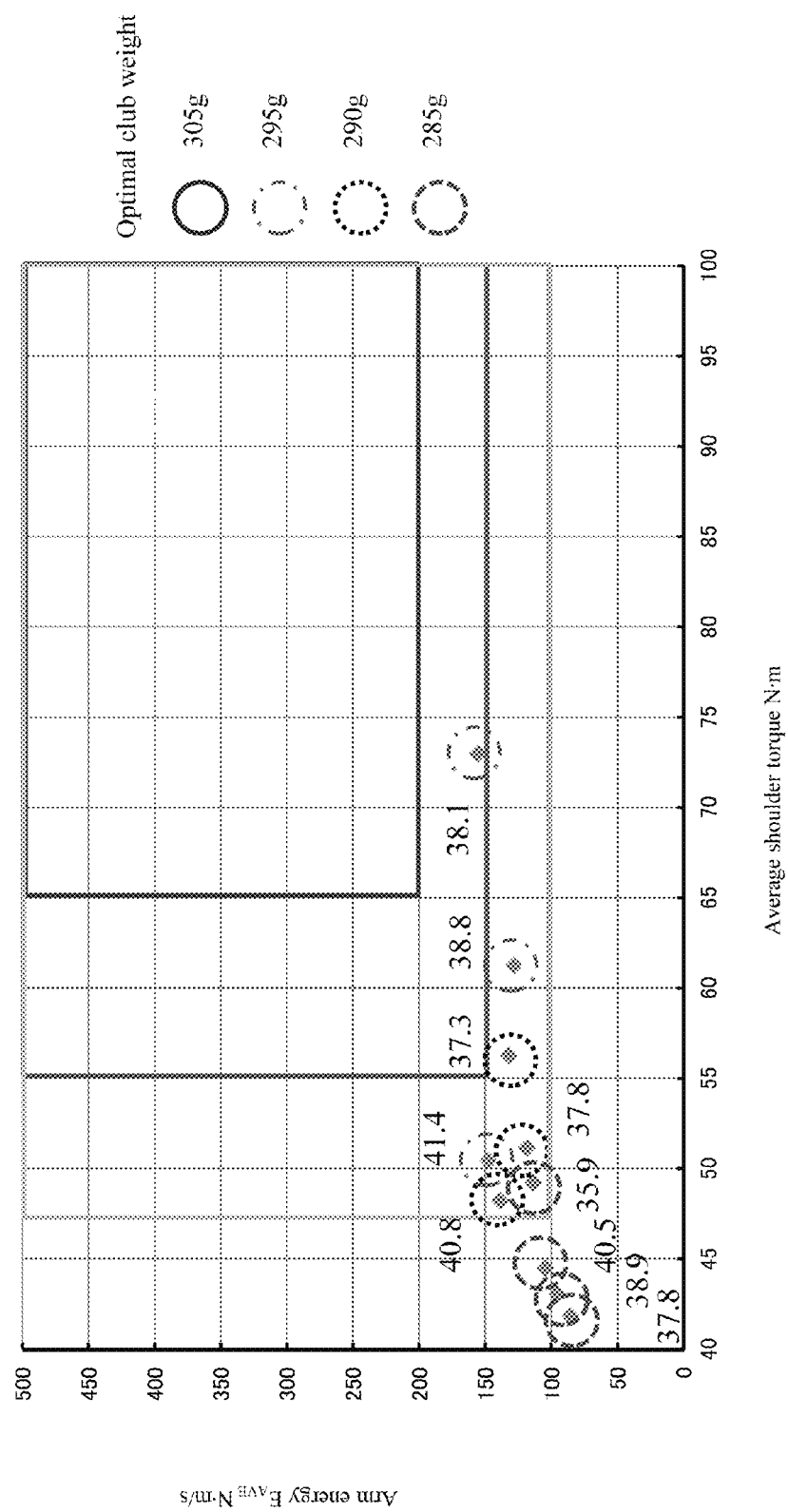
FIG. 18 is a diagram showing head speed and optimal club weight during the swing action of average model users derived empirically.

The above steps S41 to S45 and steps S51 to S53 are based on the following findings. That is, in the testing described with reference to FIGS. 14 and 15, the optimal club weight at which the carry distance is maximized and head speed $V_h$ were also calculated. Head speed $V_h$ was calculated in accordance with processes similar to the processes described above. On the other hand, the optimal club weight was determined by getting the golfers to swing golf clubs of various weights, specifying the weight of the golf club that provides the maximum carry distance, and taking the specified weight as the optimal club weight. More specifically, this involved getting the pro model users to swing five types of golf clubs having weights of 324 g, 316 g, 312 g, 308 g and 300 g, and the average model users to swing golf clubs having weights of 295 g, 290 g and 285 g. FIGS. 17 and 18 show the values of head speed $V_h$ and optimal club weight obtained from this testing.

Figure 16:
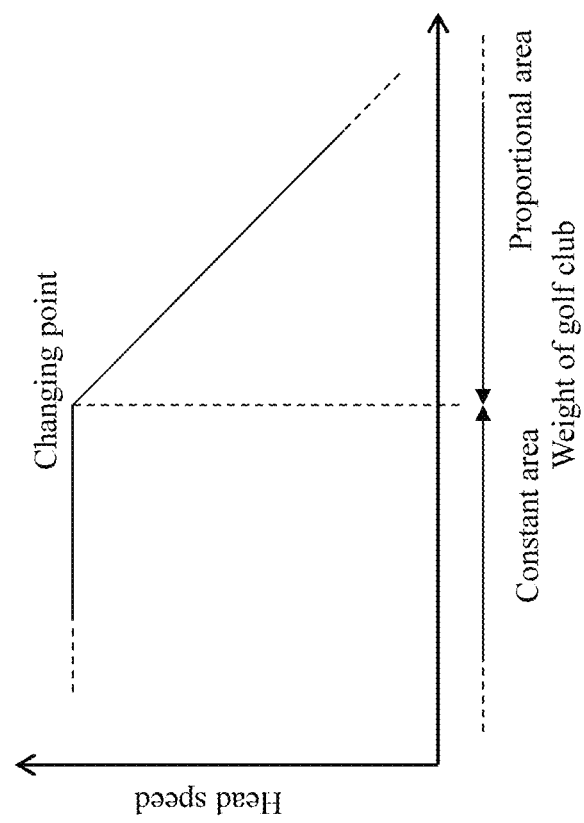
FIG. 16 is a diagram showing the relationship between the weight and head speed of a golf club.

Note that the optimal club weight can also be calculated as a simulated optimal club weight, in accordance with the following algorithm. That is, the inventors found that there is a relationship such as generally shown in FIG. 16, between head speed $V_h$ and the weight of the golf club 4. To be specific, the golfer becomes unable to fully swing the golf club as the golf club that is swung becomes heavier, and thus head speed $V_h$ decreases. Having said that, head speed $V_h$ plateaus after the weight of the golf club drops below a certain level (FIG. 16). This is because the golf club cannot be swung at greater than the power used for a full swing. In other words, head speed $V_h$ stops increasing when the golfer's limits are reached, even if the golf club is made lighter and swingability is improved. Accordingly, head speed $V_h$ is divided, at a certain point (changing point in FIG. 16), into a proportional area in which head speed $V_h$ is proportional to the weight of the golf club 4 and a constant area in which head speed $V_h$ is generally constant regardless of the weight of the golf club 4. Also, since increased head speed $V_h$ and weight of the golf club 4 are both favorable in order to increase the carry distance, it can be said that the weight of the golf club 4 corresponding to the changing point is the optimal club weight at which the carry distance is maximized. Accordingly, it is possible to get the golfers who participate in the testing to swing golf clubs 4 of various weights, and plotting the relationship between head speed $V_h$ and the weight of the golf clubs 4 in a head speed $V_h$-golf club weight plane, calculating a regression line in the proportional area and a regression line in the constant area, deriving the changing point which is the intersection thereof, and taking the golf club weight corresponding to the changing point as the optimal golf club weight.

Figure 19:
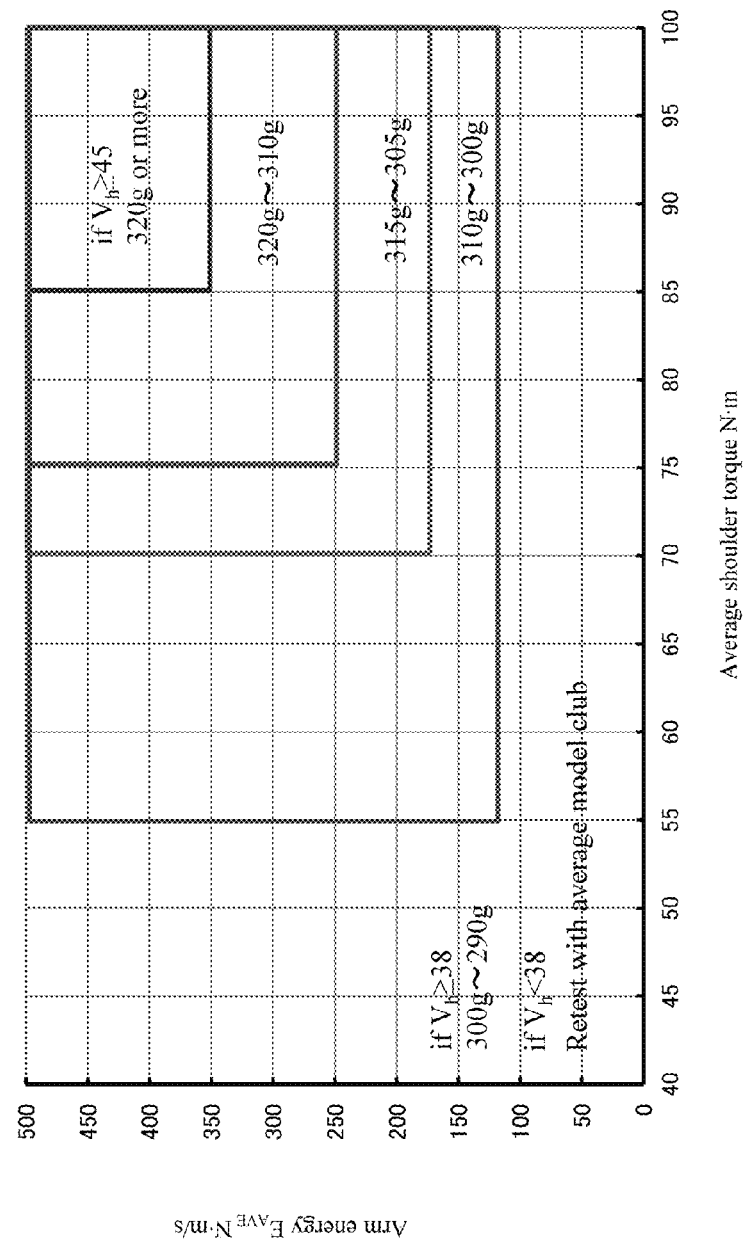
FIG. 19 is a diagram showing division areas for allocating optimal club weight to a pro model user.
Figure 20:
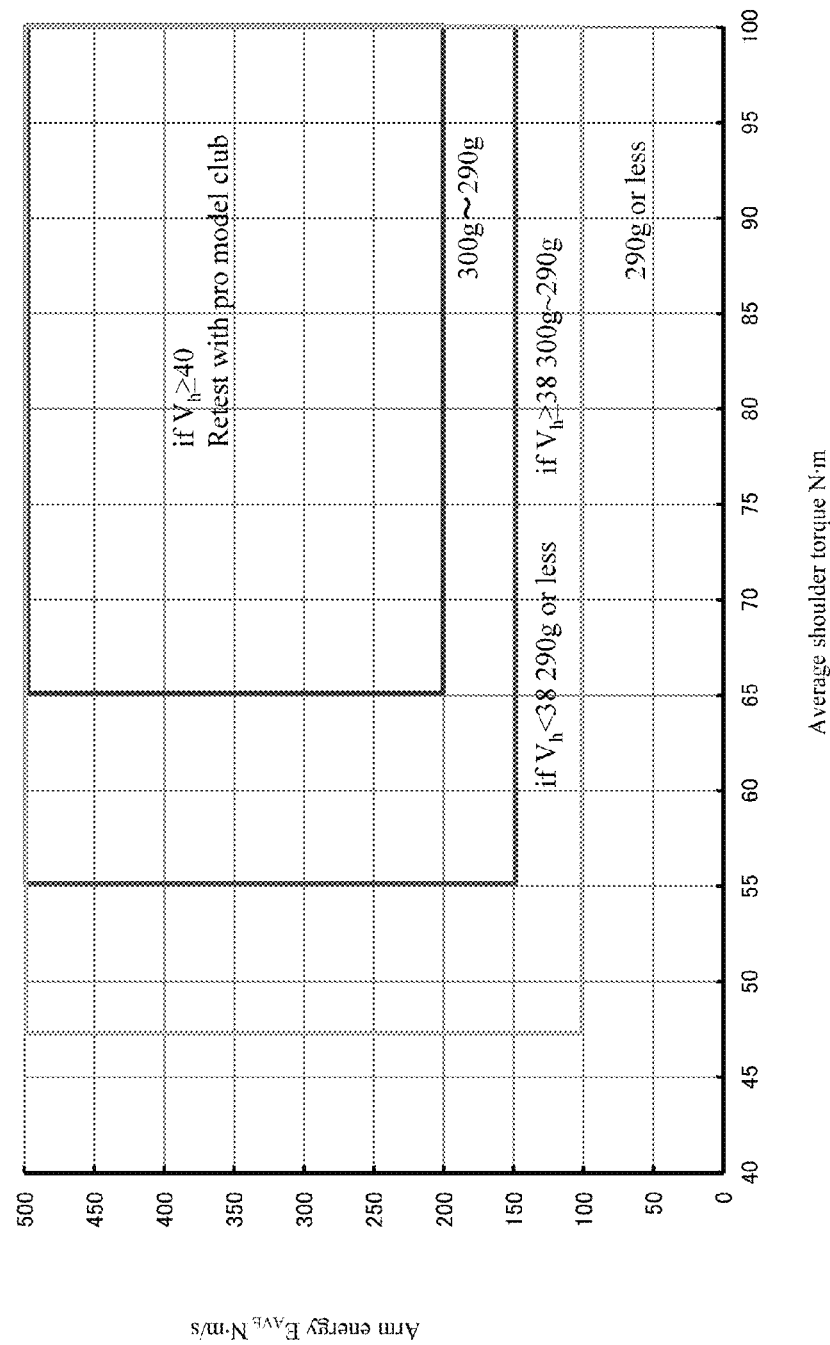
FIG. 20 is a diagram showing division areas for allocating optimal club weight to an average model user.

It is evident from the above testing that the optimal club weight increases as arm energy $E_{AVE}$ and average shoulder torque $T_{AVE}$ increase, as shown in FIGS. 17 and 18. As a result, the inventors found that the area indicating the optimal weight zone can be defined by dividing the average shoulder torque $T_{AVE}$-arm energy $E_{AVE}$-head speed $V_h$ space as shown in FIG. 19 for the average model users and as shown in FIG. 20 for the pro model users. For simplicity, however, FIGS. 19 and 20 omit an axis showing head speed $V_h$ and show an average shoulder torque $T_{AVE}$-arm energy $E_{AVE}$ plane. That is, the abovementioned steps S41 to S45 and steps S51 to S53 are steps for determining the optimal weight zone, according to which area the points indicating average shoulder torque $T_{AVE}$, arm energy $E_{AVE}$ and head speed $V_h$ are plotted in $T_{AVE}$-$E_{AVE}$-$V_h$ space. Note that the thresholds of $T_{AVE}$, $E_{AVE}$ and $V_h$ that are used in the determination processing of steps S41 to S45 and steps S51 to S53, or in other words, values indicating the boundaries of the divided areas shown in FIGS. 19 and 20, are arranged by model of the test clubs, and stored in the storage unit 23 as the correspondence data 28. That is, the correspondence data 28 is data defining the correspondence between the magnitudes of $T_{AVE}$, $E_{AVE}$ and $V_h$ and the optimal weight zone. In steps S41 to S45 and steps S51 to S53, the determination processing is performed with reference to the correspondence data 28 in the storage unit 23. Note that, in FIG. 2, the correspondence data 28 is shown as separate data to the fitting program 3 but may be incorporated in the program 3.

Incidentally, in the pro model area, a configuration is adopted such that if $T_{AVE} \geq 85$ N·m and $E_{AVE} \geq 350$ N·m/s, the optimal weight zone is allocated to one of 320 g or more and 310 g to 320 g, depending on whether head speed $V_h$ is 45 m/s or more. This is because, as indicated by the test results shown in FIG. 17, the optimal club weight in proximity to the boundary line of the area in which $T_{AVE} \geq 85$ N·m and $E_{AVE} \geq 350$ N·m/s is 316 g in the case where $V_h \leq 45$ m/s and 324 g in the case where $V_h \geq 45$ m/s.

1-2-7. Optimal Shaft Determination Process

Hereinafter, the optimal shaft determination process of calculating the optimal shaft weight and the optimal stiffness suited to the golfer 7 will be described.

First, the determination unit 24E determines the range of optimal shaft weight (hereinafter, optimal shaft weight zone) based on the optimal weight zone. Specifically, the optimal shaft weight zones are determined in advance for the respective optimal weight zones for each model of golf club 4, as shown in the following tables 1 and 2, and the optimal shaft weight zone is determined based on this.

TABLE 1

| Pro model club | |
| --- | --- |
| Optimal weight zone (club) | Optimal shaft weight zone |
| 320 g or more | 75 g or more |
| 310 g~320 g | 65 g~75 g |
| 305 g~315 g | 60 g~71 g |
| 300 g~310 g | 50 g~62 g |
| 300 g or less | 55 g or less |

TABLE 2

| Average model club | |
| --- | --- |
| Optimal weight zone (club) | Optimal shaft weight zone |
| 290 g~300 g | 45 g~55 g |
| 290 g or less | 50 g or less |

Next, the determination unit 24E determines the range of optimal stiffness of the shaft 40 (hereinafter, optimal stiffness zone). Since the method of determining the optimal stiffness zone is well known (see JP 2013-208366A if required), a detailed description will be omitted here.

Once the optimal weight zone, the optimal shaft weight zone and the optimal stiffness zone have been determined by the above steps, the determination unit 24E specifies golf clubs belonging to the optimal weight zone, the optimal shaft weight zone and the optimal stiffness zone from among various golf clubs with respect to which the overall weight of the golf club 4 and the weight and stiffness of the shaft 40 are known. The display control unit 24F displays the optimal weight zone, the optimal shaft weight zone and the optimal stiffness zone on the display unit 21 together with information indicating the types of golf clubs that were specified. The user is thereby able to find out the optimal weight zone, the optimal shaft weight zone, and the optimal stiffness zone together with being able to find out the types of golf clubs suited to the golfer 7.

2. Second Embodiment

Figure 21:
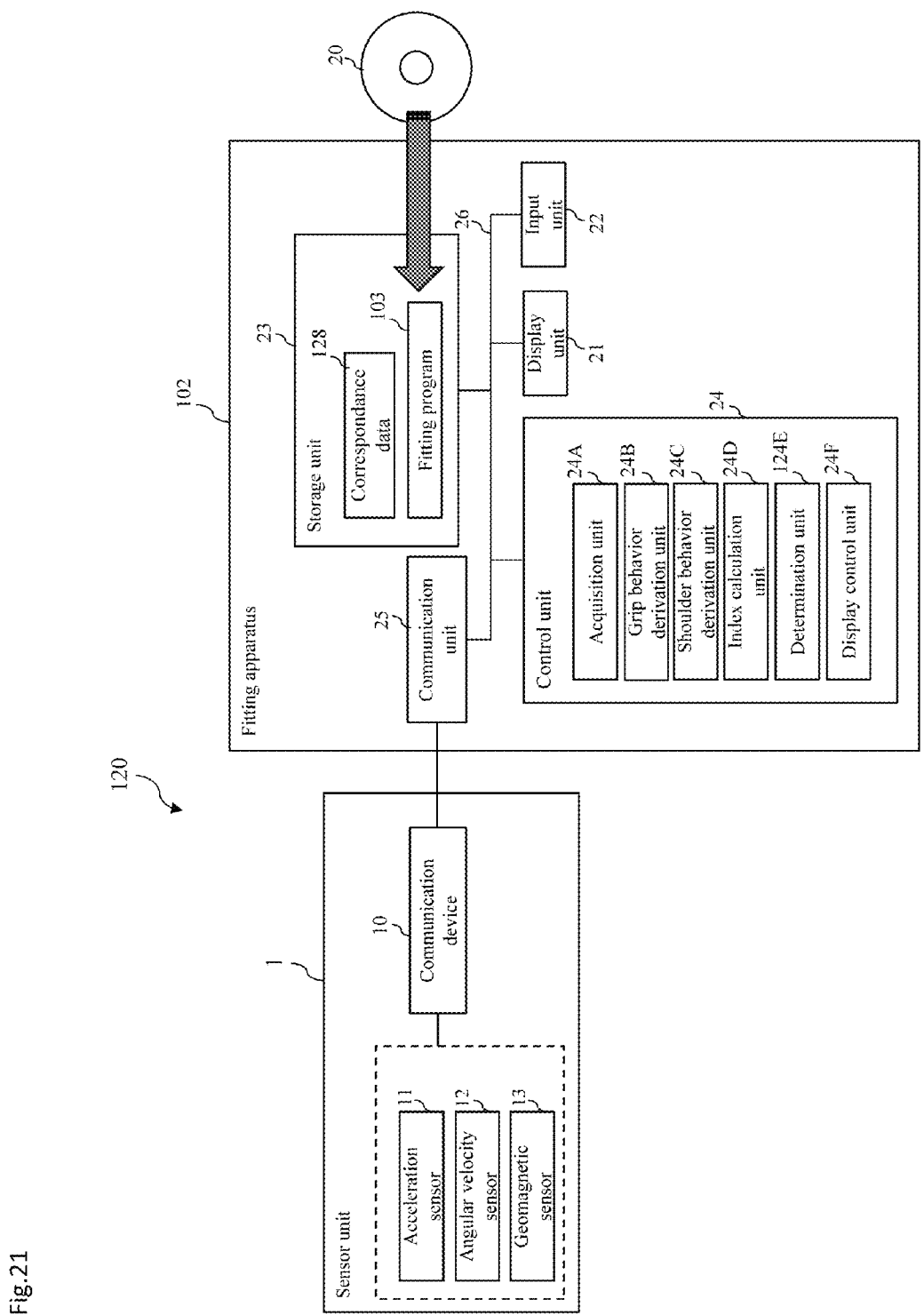
FIG. 21 is a functional block diagram of a fitting system according to a second embodiment of the present invention.

FIG. 21 shows the overall configuration of a fitting system 120 according to the second embodiment. The fitting system 120 has many points in common with the fitting system 100 according to the first embodiment. Accordingly, hereinafter, for ease of understanding, the description will focus on the differences between the embodiments, with the same reference numerals being given to constituent elements that are the same, and description thereof being omitted. The fitting system 120 is also a system that analyzes the swing action of a golf club 4 based on measurement data obtained by measuring the swing action of the golf club 4 by a golfer 7, and is applied to assisting fitting of the golf club 4. The swing action is also measured by a sensor unit 1 attached to the grip 42 of the golf club 4, similarly to the first embodiment.

The second embodiment mainly differs from the first embodiment in that an optimal swing MI determination process is executed instead of the optimal total weight determination process. More specifically, in the first embodiment, the optimal club weight is determined as the optimal swingability index, whereas in the second embodiment, the swing moment of inertia of the golf club 4 suited to the golfer (hereinafter, optimal swing MI) is determined instead. In the second embodiment, the optimal shaft determination process is also omitted.

Note that swing moment of inertia is the moment of inertia about the shoulder during the swing, and can be defined in accordance with the following equation, for example.

$$I_S = I_2 + m_2(R+L)^2 + I_1 + m_1(R/2)^2$$

where $I_S$ is the swing moment of inertia.

Note that for each golfer 7, the weight of the arm is the same, even if the golf club 4 changes. Accordingly, in the present embodiment, for simplicity, the swing moment of inertia is calculated in accordance with the following equation, omitting the rotational moment of inertia of the arm.

$$I_S = I_2 + m_2(R+L)^2$$

Furthermore, in the present embodiment, the swing moment of inertia is calculated for an arm length R of 60 cm (fixed). However, the value of the arm length R that is calculated at step S23 can also be substituted for R in the above equations. Incidentally, $m_2$, $I_2$ and L, which are parameters for determining $I_S$, are specifications of the golf club 4. Accordingly, the swing moment of inertia in the present embodiment is also a specification of the golf club 4.

As shown in FIG. 21, the fitting system 120 is provided with a fitting apparatus 102 instead of the fitting apparatus 2. The fitting apparatus 102 has the same hardware configuration as the fitting apparatus 2, although with the fitting apparatus 102, a fitting program 103 is installed instead of the fitting program 3. Thus, the control unit 24 is also able to operate as a determination unit 124E, in addition to operating in a virtual manner as the acquisition unit 24A, the grip behavior derivation unit 24B, the shoulder behavior derivation unit 24C, the index calculation unit 24D, and the display control unit 24F, by reading out and executing the fitting program 103 stored in the storage unit 23. The determination unit 124E is a virtual unit that executes the optimal swing MI determination process, which is a difference with the first embodiment. Also, correspondence data 128 is stored in the storage unit 23 of the fitting apparatus 102 instead of the correspondence data 28, so as to enable the optimal swing MI determination process to be executed. The correspondence data 128 is data indicating the conditions for determining the optimal swing MI.

In the second embodiment, the first conversion process, the second conversion process, the shoulder behavior derivation process and the index calculation process are executed sequentially, similarly to the first embodiment, and then the optimal swing MI determination process is executed. Hereinafter, the measurement process and the optimal swing MI determination process, which are differences with the first embodiment will be described.

2-1. Measurement Process

The measurement process is also executed in the second embodiment, similarly to the first embodiment. In the second embodiment, however, the golfer 7 takes practice swings with one test club having the sensor unit 1 attached, instead of two test clubs consisting of a pro model club and an average model club. In other respects, the measurement process according to the first embodiment and the second embodiment are the same. The second embodiment can, however, also be configured to take practice hits with two test clubs, thus enabling the fitting accuracy to be improved, similarly to the first embodiment.

2-2. Optimal Swing MI Determination Process

Hereinafter, the flow of the optimal swing MI determination process will be described, with reference to FIG. 22. In the optimal swing MI determination process, the range of the optimal swing MI (hereinafter, optimal swing MI zone) is determined, according to the magnitudes of average shoulder torque $T_{AVE}$, arm energy $E_{AVE}$, and head speed $V_h$. Here, the optimal swing MI zone is gradually set to larger values as the values of $T_{AVE}$, $E_{AVE}$ and $V_h$ increase.

Specifically, at step S60, the determination unit 124E determines whether average shoulder torque $T_{AVE}$ is 77 N·m or more and arm energy $E_{AVE}$ is 180 N·m/s or more (hereinafter, condition 1). If condition 1 is satisfied, the determination unit 124E determines whether head speed $V_h$ is 45 m/s or more (hereinafter, condition 2) (step S61). If condition 2 is satisfied, the determination unit 124E then determines the optimal swing MI zone to be 5600 kg·cm², and otherwise determines the optimal swing MI zone to be 5590 to 5630 kg·cm². On the other hand, if condition 1 is not satisfied at step S60, the processing advances to step S62. In step S62, the determination unit 124E determines whether average shoulder torque $T_{AVE}$ is 60 N·m or more and arm energy $E_{AVE}$ is 170 N·m/s or more (hereinafter, condition 3). If condition 3 is satisfied, the determination unit 124E determines whether head speed $V_h$ is 45 m/s or more (hereinafter, condition 4) (step S63). If condition 4 is satisfied, the determination unit 124E then determines the optimal swing MI zone to be 5590 to 5630 kg·cm², and otherwise determines the optimal swing MI zone to be 5510 to 5590 kg·cm². On the other hand, if condition 3 is not satisfied at step S62, the processing advances to step S64. In step S64, the determination unit 124E determines whether average shoulder torque $T_{AVE}$ is 50 N·m or more and arm energy $E_{AVE}$ is 130 N·m/s or more (hereinafter, condition 5). If condition 5 is satisfied, the determination unit 124E then determines the optimal swing MI zone to be 5460 to 5510 kg·cm², and otherwise determines the optimal swing MI zone to be 5480 kg·cm² or less.

Figure 23:
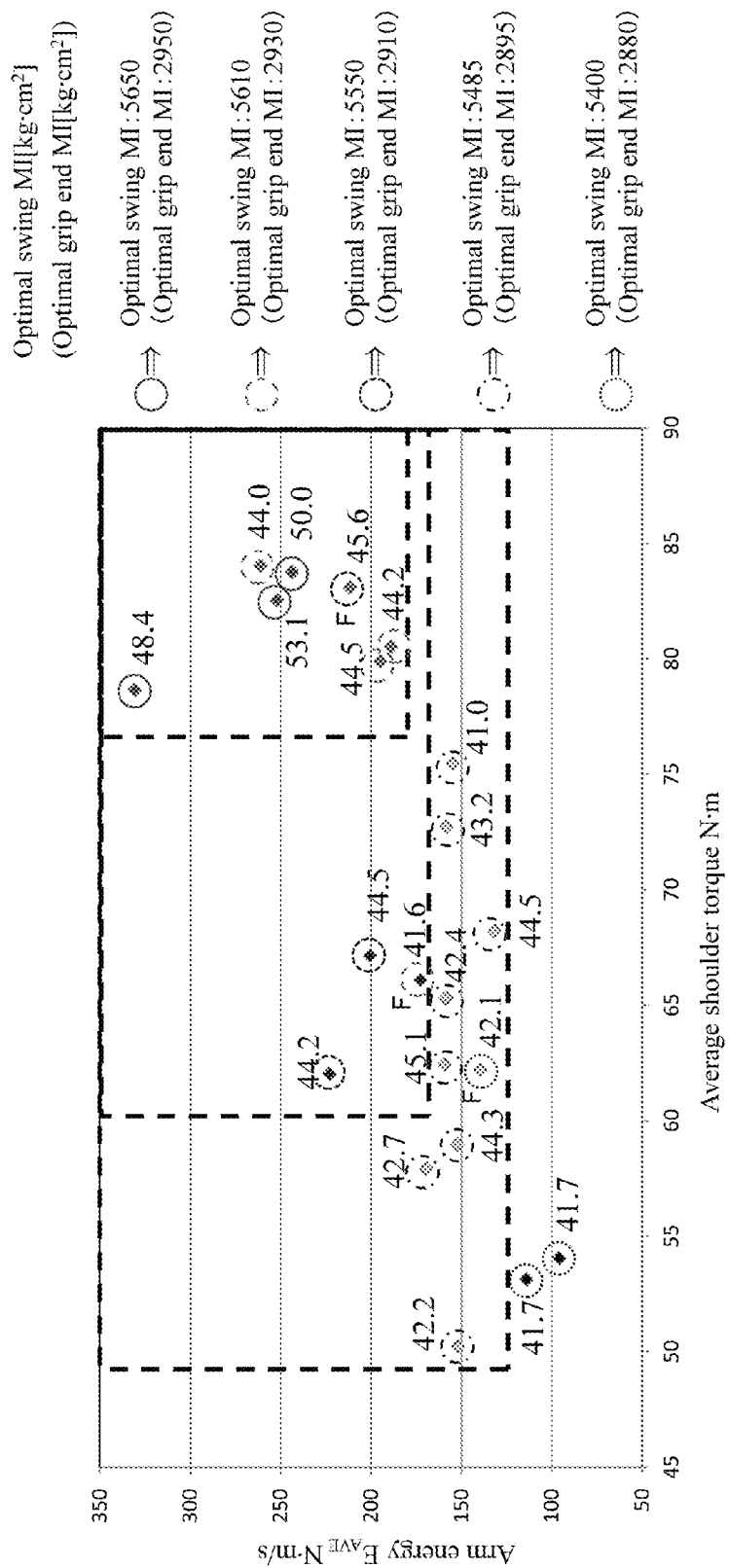
FIG. 23 is a diagram showing head speed, optimal swing MI and optimal grip end MI during the swing action of a plurality of golfers derived empirically.

The above steps S60 to S64 are based on the following findings. That is, testing similar to FIG. 14 was also performed here. More specifically, the inventors obtained the results shown in FIG. 23 after getting 21 golfers to take practice hits with the test club according to the present embodiment and then calculating swing indices. Note that the swing indices calculated in this testing were average shoulder torque $T_{AVE}$ and arm energy $E_{AVE}$, and the specific values were calculated in accordance with a process similar to the process described above. This testing was performed using a SRIXON (registered trademark) Z-525 driver made by Dunlop Sports Co. Ltd. (Miyazaki Kosuma Blue 6 S-Flex shaft, club weight of 314 g, and swing weight of D3) as the test club. Also, in this testing, the optimal swing MI at which the carry distance is maximized and head speed $V_h$ were also calculated. Head speed $V_h$ was calculated in accordance with processes similar to the processes described above. On the other hand, the optimal swing MI was determined by getting the golfers to swing golf clubs having various swing moments of inertia, specifying the swing moment of inertia of the golf club that provides the greatest carry distance, and taking the specified swing moment of inertia as the optimal swing MI. More specifically, the golfers were made to swing five types of golf clubs having swing moments of inertia of 5650 kg·cm², 5610 kg·cm², 5550 kg·cm², 5485 kg·cm², and 5400 kg·cm². FIG. 23 shows the values of head speed $V_h$ and optimal swing MI obtained by this testing.

Figure 24:
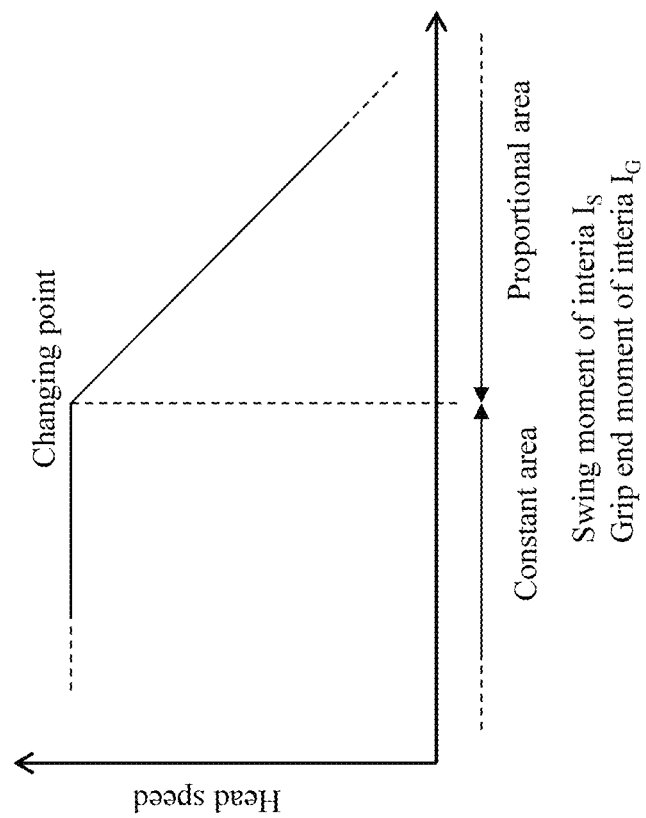
FIG. 24 is a diagram showing the relationship of swing moment of inertia and grip end moment of inertia with head speed.

Note that the optimal swing MI can also be calculated as a simulated optimal swing MI, in accordance with the following algorithm. That is, the inventors found that there is a relationship such as generally shown in FIG. 24 between a swing index such as head speed $V_h$ and not only weight $m_2$ of the golf club 4 but also a swingability index such as swing moment of inertia $I_S$ of the golf club 4. To be specific, the golf club 4 becomes more difficult to swing and head speed $V_h$ decreases as swing moment of inertia $I_S$ of the golf club 4 that is swung increases. Having said that, head speed $V_h$ plateaus after $I_S$ drops below certain level (see FIG. 24). This is because the golf club cannot be swung at greater than the power used for a full swing. In other words, head speed $V_h$ stops increasing when the golfer's limits are reached, even if swing moment of inertia $I_S$ is reduced to below a certain level and swingability is improved. Accordingly, head speed $V_h$ is divided, at a certain point (changing point in FIG. 24), into a proportional area in which head speed $V_h$ is proportional to swing moment of inertia $I_S$ and a constant area in which head speed $V_h$ is generally constant regardless of swing moment of inertia $I_S$. Also, since increased head speed $V_h$ is favorable in order to increase the carry distance, it can be said that the swing moment of inertia of the golf club 4 corresponding to the above changing point is the optimal swing MI at which the carry distance is maximized. Accordingly, it is possible to get the golfers who participate in the testing to swing golf clubs 4 of various swing moments of inertia $I_S$, and plotting the relationship between head speed $V_h$ and swing moment of inertia $I_S$ in a head speed $V_h$-swing moment of inertia $I_S$ plane, calculating a regression line in the proportional area and a regression line in the constant area, deriving the changing point which is the intersection thereof, and taking swing moment of inertia $I_S$ corresponding to the changing point as the optimal swing MI. Note that a similar relationship is established between grip end moment of inertia $I_G$ and head speed $V_h$ which will be described in a third embodiment, and optimal grip end MI which will be discussed later can also be similarly calculated based on the relationship in FIG. 24.

Figure 25:
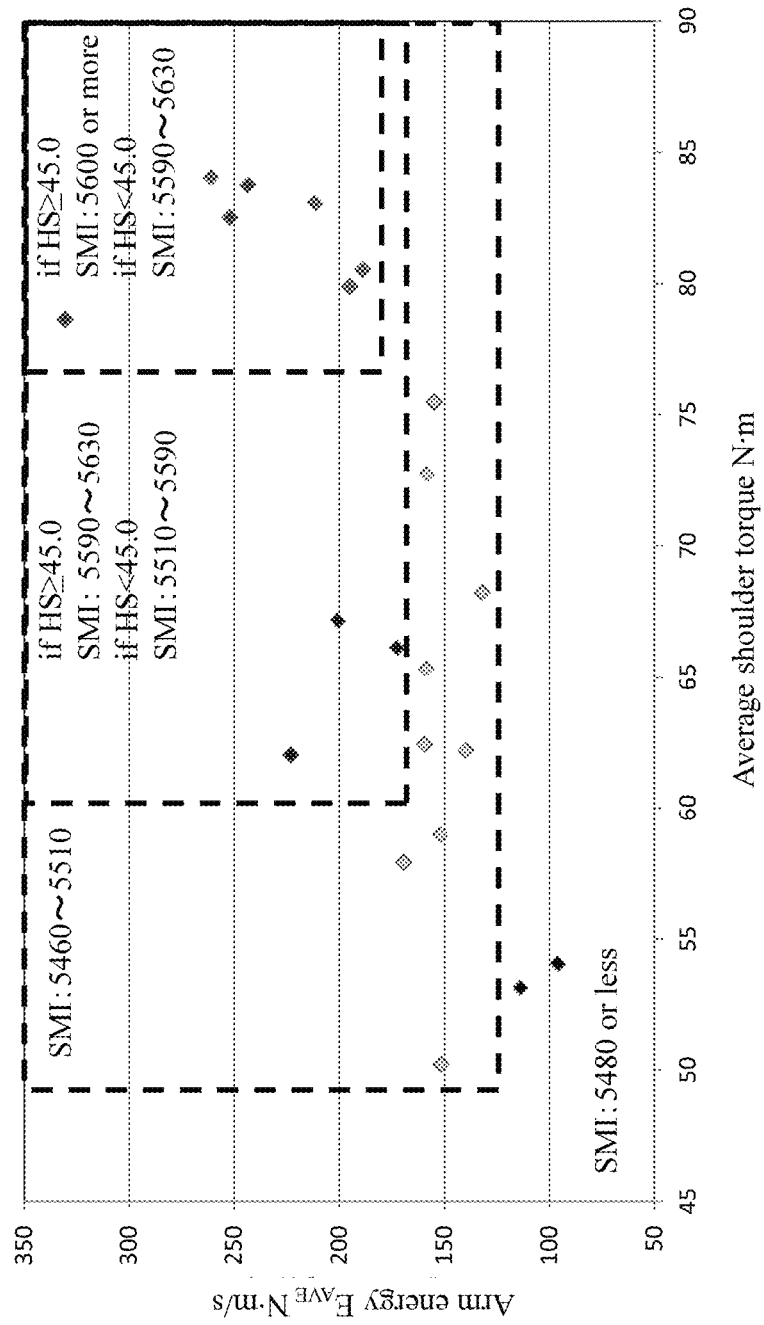
FIG. 25 is a diagram showing division areas for allocating the optimal swing MI.

It is evident from the testing that the optimal swing MI increases as both arm energy $E_{AVE}$ and average shoulder torque $T_{AVE}$ increase, as shown in FIG. 23. As a result, the inventors found that the area indicating the optimal swing MI zone can be defined by dividing the average shoulder torque $T_{AVE}$-arm energy $E_{AVE}$-head speed $V_h$ space as shown in FIG. 25. For simplicity, however, FIG. 25 omits an axis representing head speed $V_h$ and shows the average shoulder torque $T_{AVE}$-arm energy $E_{AVE}$ plane. That is, the abovementioned steps S60 to S64 are steps for determining the optimal swing MI zone according to which area the points indicating average shoulder torque $T_{AVE}$, arm energy $E_{AVE}$, and head speed $V_h$ are plotted in $T_{AVE}$-$E_{AVE}$-$V_h$ space. Note that the thresholds of $T_{AVE}$, $E_{AVE}$ and $V_h$ that are used in the determination processing of steps S60 to S64, or in other words, the values indicating the boundary between the divided areas shown in FIG. 25, are stored in the storage unit 23 as the correspondence data 128. That is, the correspondence data 128 is data for determining the correspondence between the magnitudes of $T_{AVE}$, $E_{AVE}$ and $V_h$, and the optimal swing MI zone. In steps S60 to S64, the above determination is performed with reference to correspondence data 128 in the storage unit 23. Note that, in FIG. 21, the correspondence data 128 is shown as separate data from a fitting program 103 but may be incorporated into the program 103.

Incidentally, a configuration is adopted such that in the case where $T_{AVE} \geq 77$ N·m and $E_{AVE} \geq 180$ N·m/s (condition C1) or where $T_{AVE} \geq 60$ N·m and $E_{AVE} \geq 170$ N·m/s and condition C1 is not satisfied, the optimal swing MI zone is allocated to one of 5600 kg·cm² or more, 5590 to 5630 kg·cm², and 5510 to 5590 kg·cm², depending on whether head speed $V_h$ is 45 m/s or more. This is because, as indicated by the test results shown in FIG. 23, in these areas, the optimal swing MI takes a different value depending on whether $V_h \geq 45$ m/s.

Once the optimal swing MI zone has been determined by the above steps, the determination unit 124E specifies golf clubs that belongs to the optimal swing MI zone from among various golf clubs with respect to which the swing MI is known. Note that, in the storage unit 23, information specifying a large number of golf clubs (manufacturer, model number, etc.) is stored in advance in association with the swing moments of inertia of the golf clubs or information indicating specifications including values required to calculate the swing moments of inertia. The display control unit 24F displays the optimal swing MI zone on the display unit 21 together with the information indicating the types of golf clubs that were specified. The user is thereby able to find out the optimal swing MI zone together with being able to find out the types of golf clubs suited to the golfer 7.

3. Third Embodiment

Figure 26:
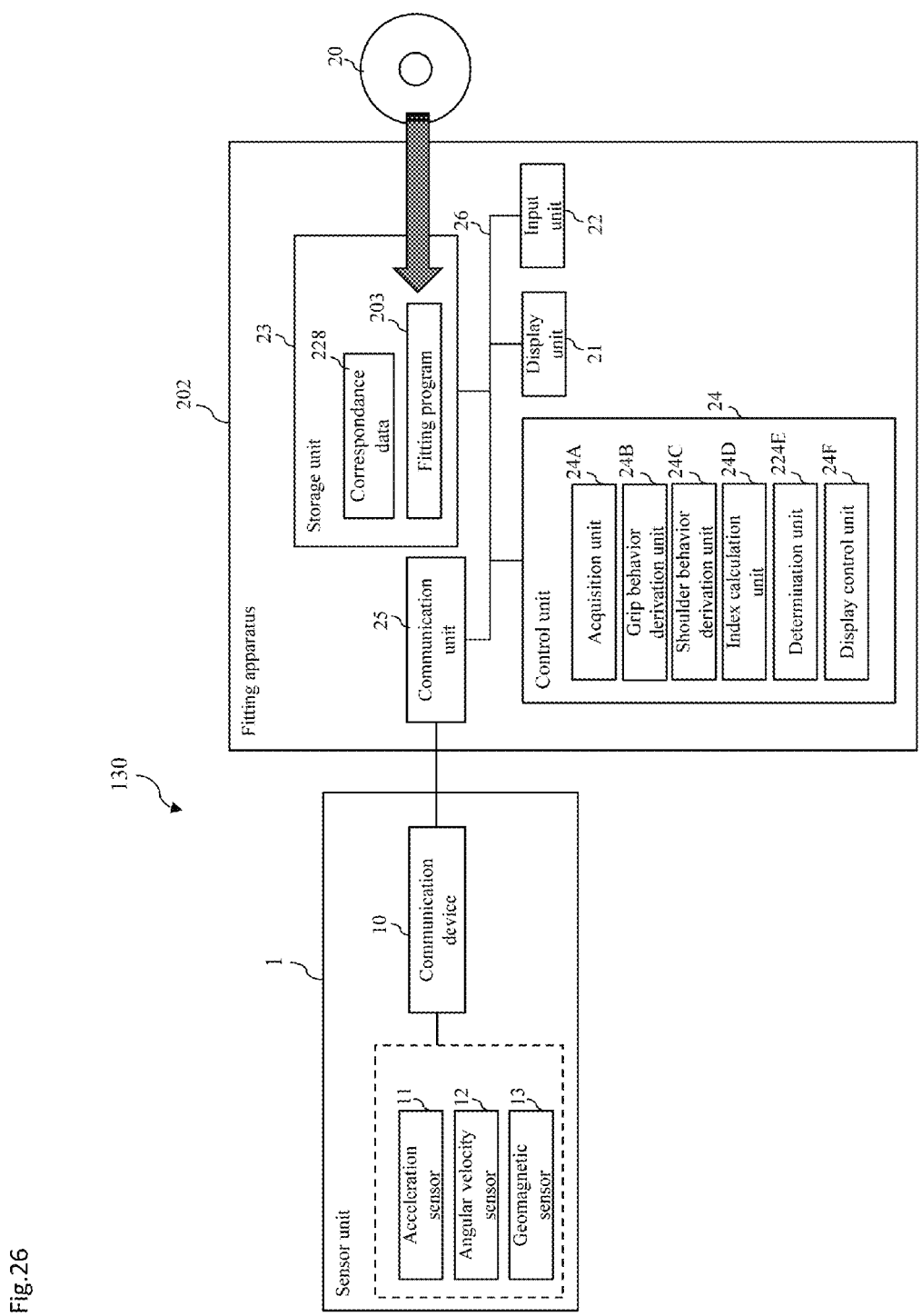
FIG. 26 is a functional block diagram of a fitting system according to a third embodiment of the present invention.

FIG. 26 shows the overall configuration of a fitting system 130 according to a third embodiment. The fitting system 130 has many points in common with the fitting systems 100 and 120 according to the first and second embodiments, particularly the fitting system 120. Accordingly, hereinafter, for simplicity, the description will focus on the differences between the third embodiment and the second embodiment, with the same reference numerals being given to constituent elements that are the same as the above first and second embodiments, and description thereof being omitted. The fitting system 130 is a system that analyzes the swing action of a golf club 4, based on measurement data obtained by measuring the swing action of the golf club 4 by the golfer 7, and is used in applications for assisting the fitting of the golf club 4. The swing action is also measured by the sensor unit 1 attached to the grip 42 of the golf club 4, similarly to the first and second embodiments.

The third embodiment mainly differs from the second embodiment in that an optimal grip end MI determination process is executed instead of the optimal swing MI determination process. More specifically, in the second embodiment, the optimal swing MI is determined as the optimal swingability index, whereas in the third embodiment, the grip end moment of inertia of the golf club 4 suited to a golfer (hereinafter, optimal grip end MI) is determined instead. The optimal shaft determination process is also skipped in the third embodiment.

Note that grip end moment of inertia is the moment of inertia about the grip end, and is, in the present embodiment, calculated in accordance with the following equations.

$$I_G = I_2 + m_2 L^2$$

where $I_G$ is the grip end moment of inertia. Incidentally, $m_2$, $I_2$ and $L$, which are parameters for determining $I_G$, are specifications of the golf club 4. Accordingly, the grip end moment of inertia of the present embodiment is also a specification of the golf club 4.

As shown in FIG. 26, the fitting system 130 is provided with a fitting apparatus 202 instead of the fitting apparatus 102. The fitting apparatus 202 has a similar hardware configuration as the fitting apparatus 102, although with the fitting apparatus 202, a fitting program 203 is installed instead of the fitting program 103. Thus, the control unit 24 is also able to operate as a determination unit 224E, in addition to operating in a virtual manner as the acquisition unit 24A, the grip behavior derivation unit 24B, the shoulder behavior derivation unit 24C, the index calculation unit 24D, and the display control unit 24F. The determination unit 224E is a virtual unit that executes the optimal grip end MI determination process, which is a difference with the second embodiment. Also, correspondence data 228 is stored in the storage unit 23 of the fitting apparatus 202 instead of the correspondence data 128, so as to enable the optimal grip end MI determination process to be performed. The correspondence data 228 is data showing conditions for determining the optimal grip end MI.

In the third embodiment, the measurement process, the first conversion process, the second conversion process, the shoulder behavior derivation process and the index calculation process are executed sequentially, similarly to the second embodiment, and then the optimal grip end MI determination process is executed. Hereinafter, the optimal grip end MI determination process which is a difference with the second embodiment, will be described.

3-1. Optimal Grip End MI Determination process

Figure 22:
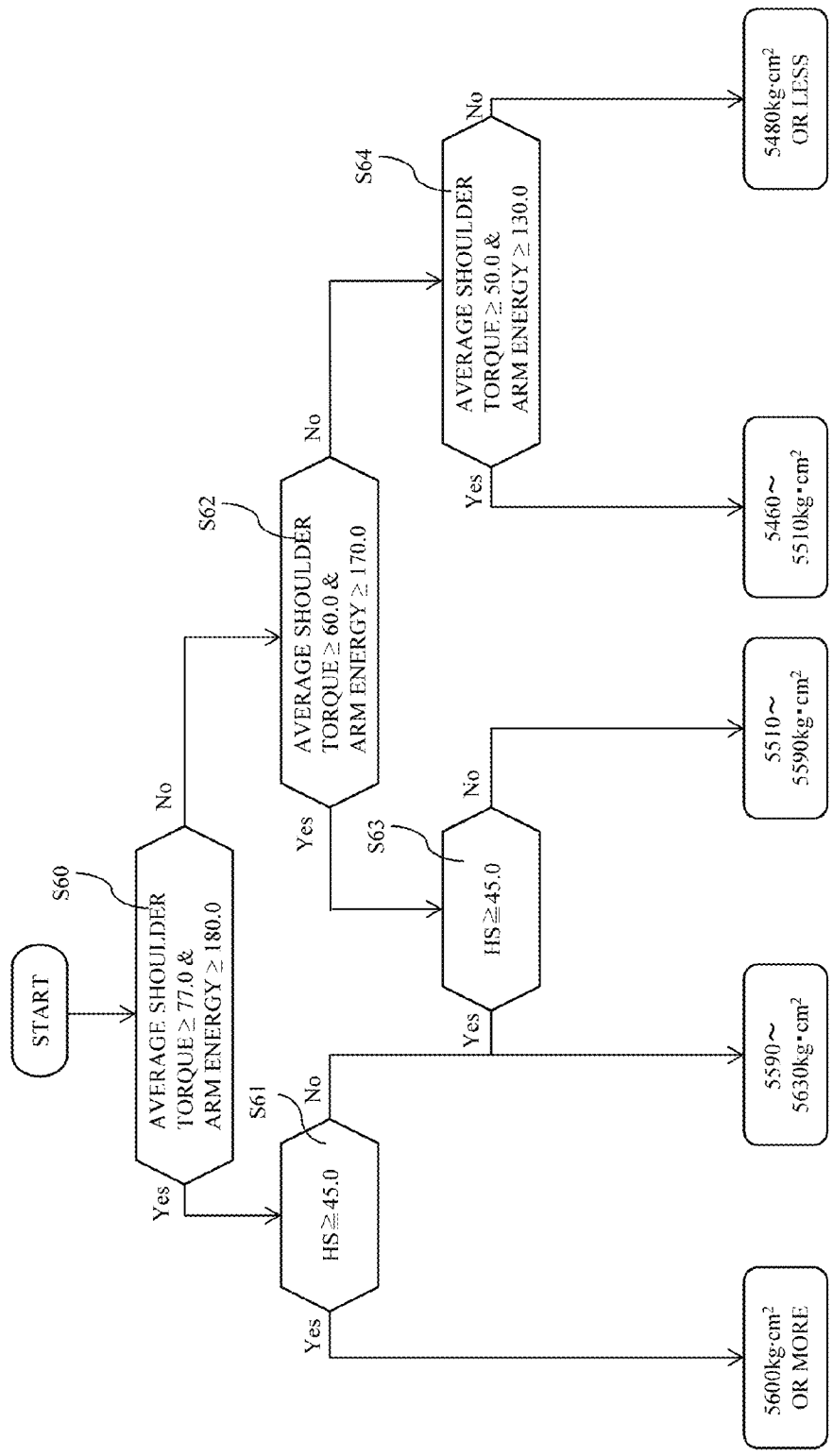
FIG. 22 is a flowchart showing the flow of an optimal swing MI determination process.
Figure 27:
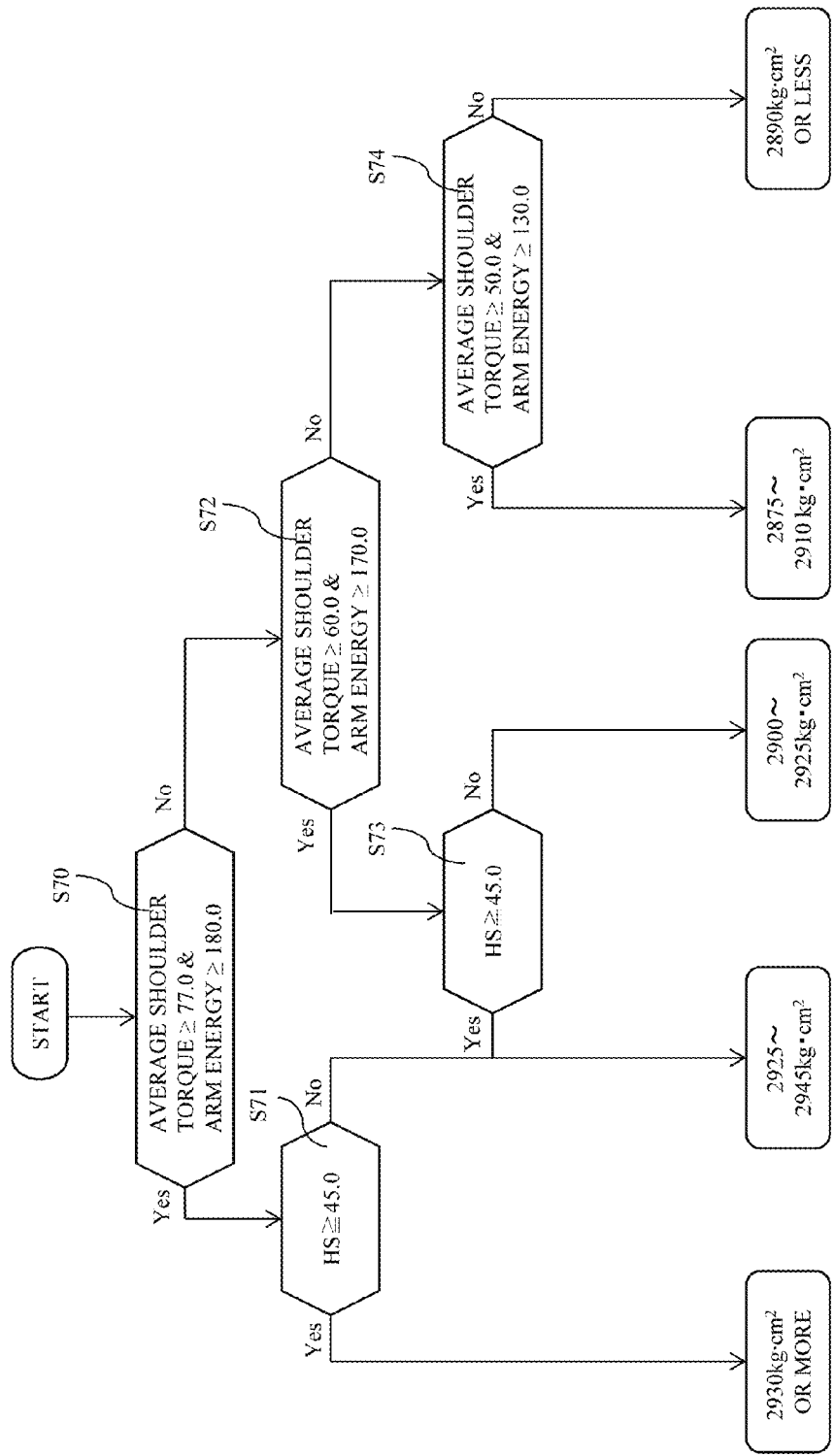
FIG. 27 is a flowchart showing the flow of an optimal grip end MI determination process.

It is evident, on comparing FIGS. 22 and 27, that the optimal grip end MI determination process is the same as the optimal swing MI determination process, apart from the optimal swingability index that is ultimately allocated being different. Accordingly, a detailed description will be omitted, although in the optimal grip end MI determination process, as shown in FIG. 27, the range of the optimal grip end MI (hereinafter, optimal grip end MI zone) is determined according to the magnitudes of average shoulder torque $T_{AVE}$, arm energy $E_{AVE}$ and head speed $V_h$. Also, an optimal grip end MI zone is gradually set to larger values as the values of $T_{AVE}$, $E_{AVE}$ and $V_h$ increase.

Figure 28:
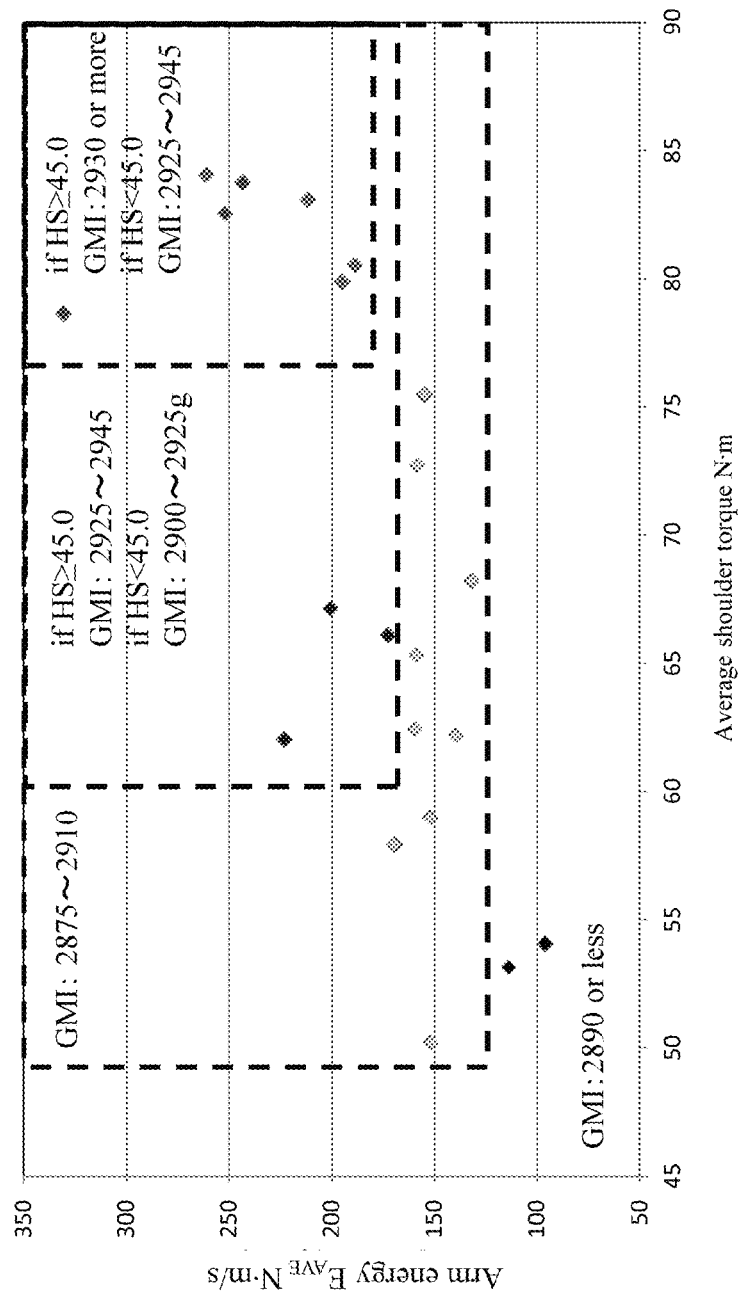
FIG. 28 is a diagram showing division areas for allocating the optimal grip end MI.

It is evident from a comparison of the definitional equations of the grip end moment of inertia and the swing moment of inertia that both are mutually convertible if the arm length R is known. Returning here to FIG. 23, value obtained by converting the optimal swing MI into the optimal grip end MI are also shown in the legend on the right side in FIG. 23. It is evident from the above that the optimal grip end MI also increases as both arm energy $E_{AVE}$ and average shoulder torque $T_{AVE}$ increase. Accordingly, the average shoulder torque $T_{AVE}$-arm energy $E_{AVE}$-head speed $V_h$ space can be divided into areas indicating an optimal grip end MI zone, as shown in FIG. 28. However, for simplicity, FIG. 28 omits an axis indicating head speed $V_h$ and shows the average shoulder torque $T_{AVE}$-arm energy $E_{AVE}$ plane. That is, steps S70 to S74 of the optimal grip end MI determination process are steps for determining the optimal grip end MI zone according to which area the points indicating average shoulder torque $T_{AVE}$, arm energy $E_{AVE}$ and head speed $V_h$ are plotted in $T_{AVE}$-$E_{AVE}$-$V_h$ space, similarly to the second embodiment. Note that the thresholds of $T_{AVE}$, $E_{AVE}$ and $V_h$ that are used in the determination processing at steps S70 to S74 of the present embodiment, or in other words, values indicating the boundaries of the divided areas shown in FIG. 28 are stored in the storage unit 23 as the correspondence data 228. That is, the correspondence data 228 is data defining the correspondence between the magnitudes of $T_{AVE}$, $E_{AVE}$ and $V_h$ and the optimal grip end MI zone. In steps S70 to S74 of the present embodiment, the optimal grip end MI zone is determined, with reference to the correspondence data 228 in the storage unit 23. Note that, in FIG. 26, the correspondence data 228 is shown as separate data from the fitting program 203 but may be incorporated in the program 203.

Once the optimal grip end MI zone has been determined by the above steps, the determination unit 224E specifies golf clubs belonging to the optimal grip end MI zone from among various golf clubs with respect to which the grip end moment of inertia is known. Note that, in the storage unit 23, information (manufacturer, model number, etc.) specifying a large number of golf clubs is stored in advance in association with the grip end moments of inertia of the golf club or information indicating specifications including values required to calculate the grip end moment of inertia. The display control unit 24F displays the optimal grip end MI zone on the display unit 21 together with information indicating the types of golf clubs that were specified. The user is thereby able to find out the optimal grip end MI zone, together with being able to find out the types of golf clubs suited to the golfer 7.

Incidentally, the results of testing that involved getting 21 golfers to actually take practice hits with the test clubs are plotted in FIG. 23, as described above. Out of the swing data for the 21 golfers, the optimal swing MI and the optimal grip end MI for 18 golfers, excluding the 3 golfers that are marked by F, ended up belonging to the optimal swing MI zone and the optimal grip end MI zone that were determined in the abovementioned optimal swing MI determination process and optimal grip end MI determination process. That is, it was confirmed that fitting was performed with a validity of 86%.

4. Fourth Embodiment

Figure 29:
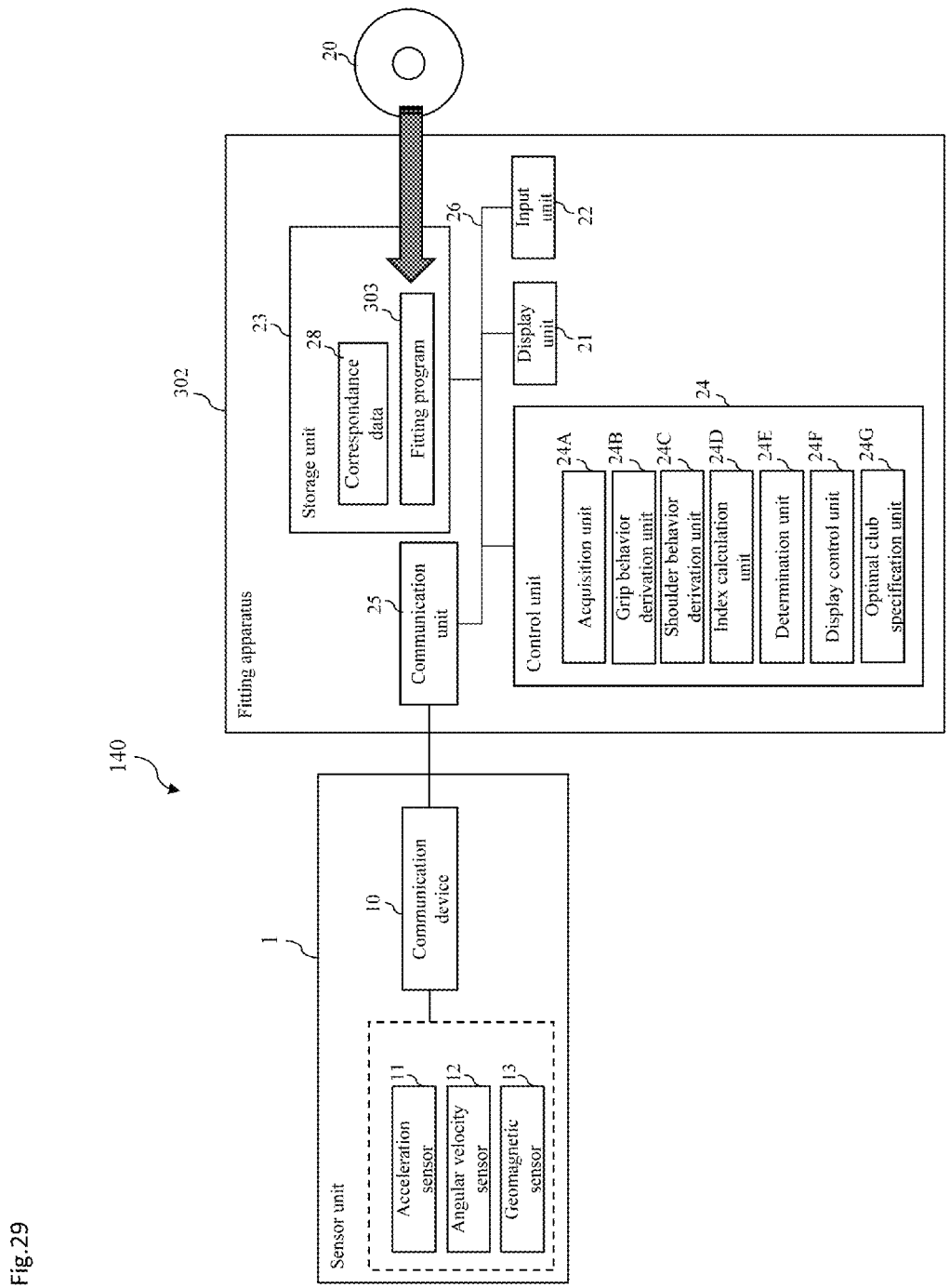
FIG. 29 is a functional block diagram of a fitting system according to a fourth embodiment of the present invention.

FIG. 29 shows the overall configuration of a fitting system 140 according to a fourth embodiment. The fitting system 140 has many points in common with the fitting systems 100, 120 and 130 according to the first to third embodiments, particularly, the fitting system 100. Accordingly, hereinafter, for simplicity, the description will focus on the differences between the fourth embodiment and the first embodiment, with the same reference numerals being given to constituent elements that are the same as the above first to third embodiments, and description thereof being omitted.

The fourth embodiment mainly differs from the first embodiment in that an optimal club specification process is executed. The optimal club specification process is a process for specifying a golf club that can particularly enhance head speed from among a plurality of golf clubs that match the optimal club weight specified in the optimal total weight determination process and match the optimal shaft weight and optimal stiffness calculated in the optimal shaft determination process.

As shown in FIG. 29, the fitting system 140 is provided with a fitting apparatus 302, instead of the fitting apparatus 2. The fitting apparatus 302 has the same hardware configuration as the fitting apparatus 2, although with the fitting apparatus 302, a fitting program 303 is installed instead of the fitting program 3. Thus, the control unit 24 is also able to operate as an optimal club specification unit 24G, in addition to operating in a virtual manner as the acquisition unit 24A, the grip behavior derivation unit 24B, the shoulder behavior derivation unit 24C, the index calculation unit 24D, the determination unit 24E, and the display control unit 24F, by reading and executing the fitting program 103 in the storage unit 23. The optimal club specification unit 24G is a virtual unit that executes the optimal total weight determination process which is a difference with the first embodiment.

In the fourth embodiment, processing from the measurement process to the optimal shaft determination process is executed sequentially, similarly to the first embodiment, and then the optimal club specification process is executed. Hereinafter, the optimal club specification process which is a difference with the first embodiment will be described.

4-1. Optimal Club Specification Process

At an optimal shaft determination process, as described above, golf clubs (hereinafter, candidate clubs) belonging to the optimal weight zone, the optimal shaft weight zone and the optimal stiffness zone are specified from among various golf clubs (hereinafter, target clubs) with respect to which the overall weight of the golf club 4 and the weight and stiffness of the shaft 40 are known. The optimal club specification process is a process for specifying a golf club (hereinafter, optimal club) that can enhance head speed in particular, from among the candidate clubs specified in the above processes. The optimal club is specified based on the values of grip end moment of inertia $I_G$ and swing moment of inertia $I_S$ in the case where the golfer 7 who is being fitted has used each of the candidate clubs.

Figure 30:
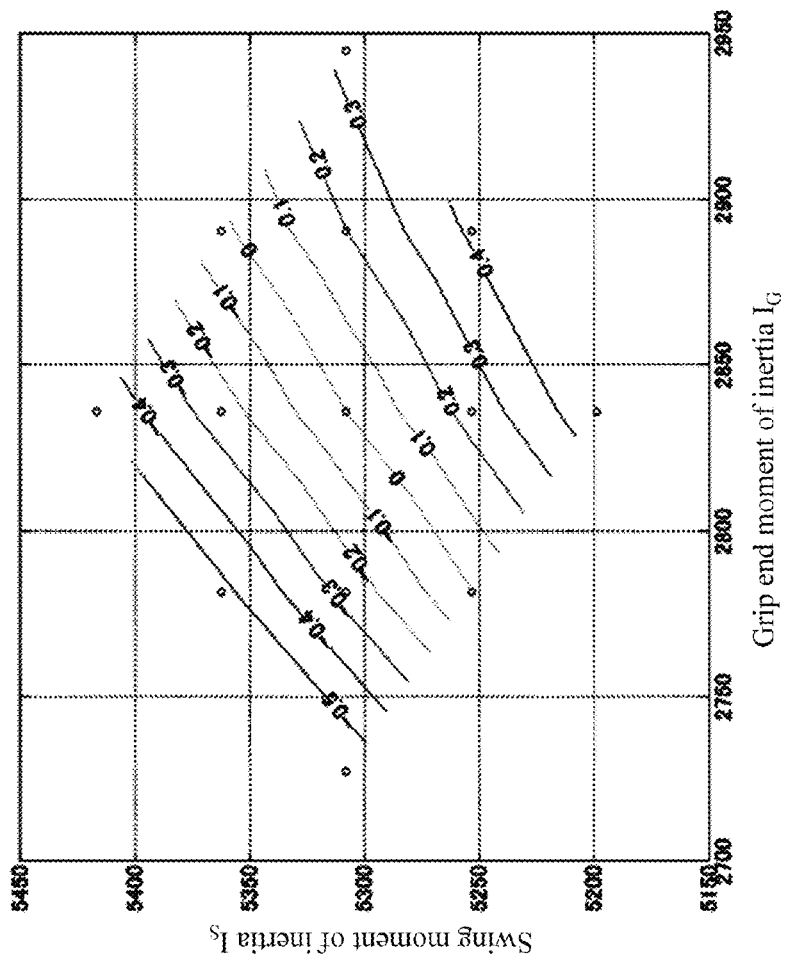
FIG. 30 is a contour diagram of head speed derived through simulation.
Figure 31:
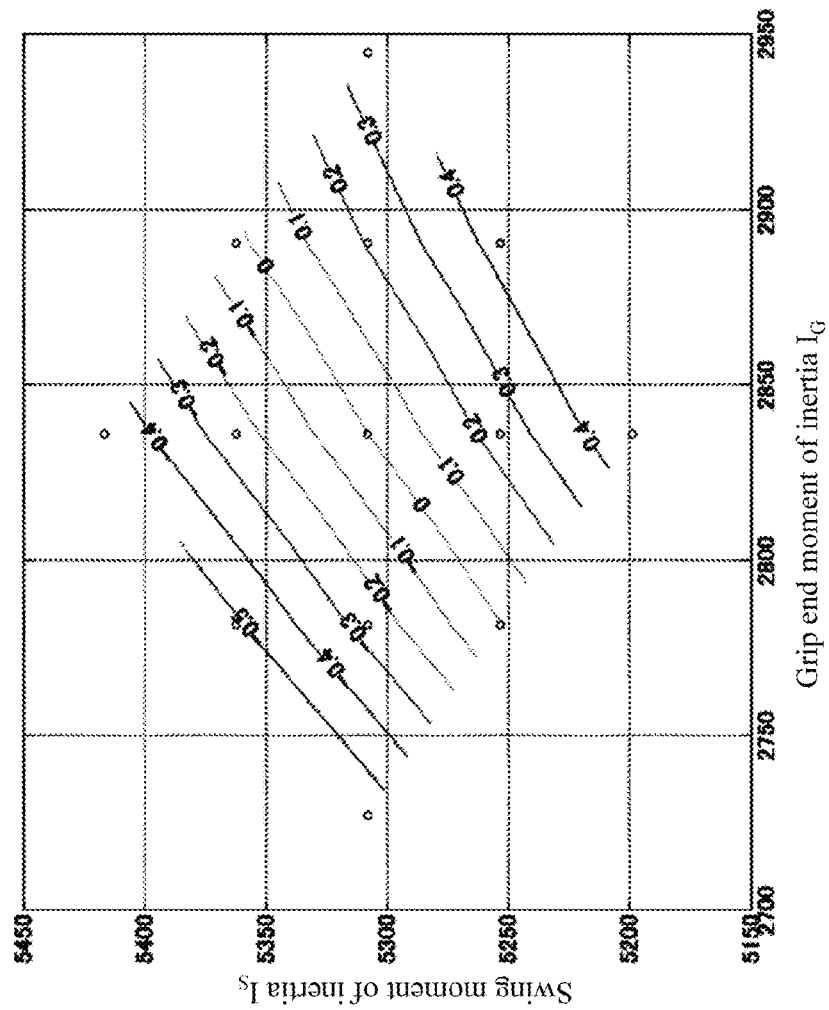
FIG. 31 is a contour diagram of the head speed derived through another simulation.
Figure 32:
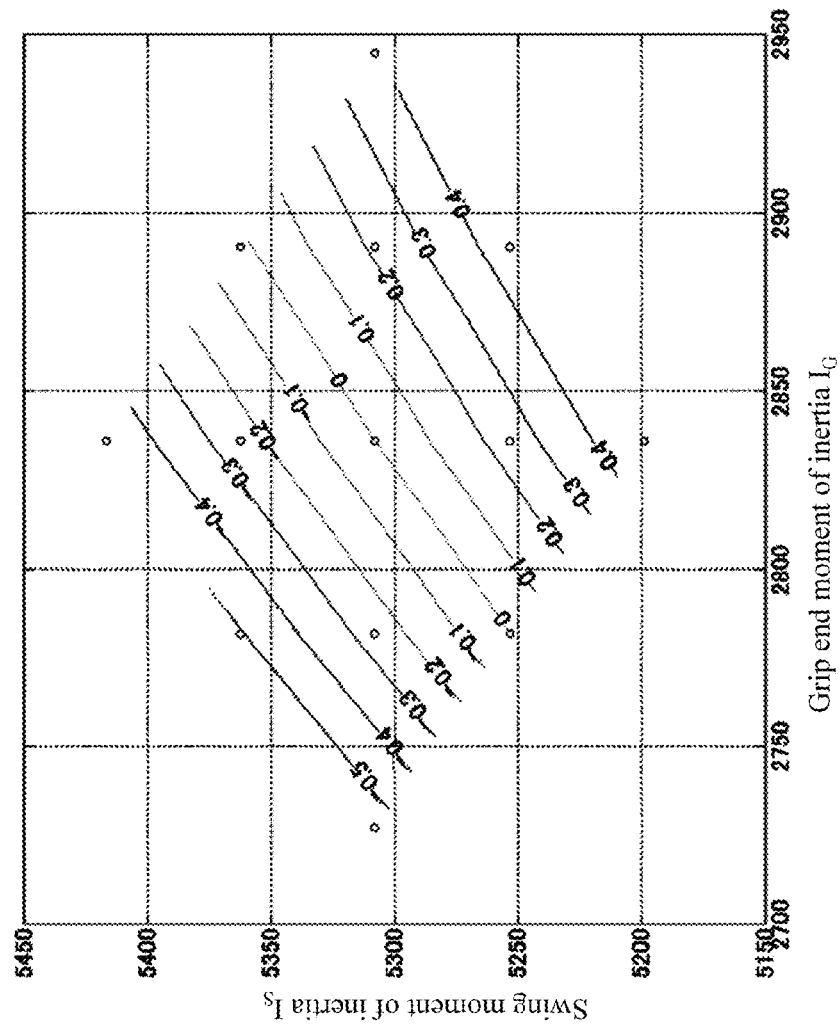
FIG. 32 is a contour diagram of the head speed derived through yet another simulation.

The algorithm of the optimal club specification process described below is based on head speed $V_h$, grip end moment of inertia $I_G$ and swing moment of inertia $I_S$ having a relationship such as shown in FIGS. 30 to 32. FIGS. 30 to 32 show the results of simulations performed by the inventors. The 13 dots (circles) in an $I_G$-$I_S$ plane in FIG. 21 are dots showing ($I_G$, $I_S$) when a subject swings 13 golf clubs having different specifications. Note that this data is not data obtained by getting the subject to actually take practice hits with 13 golf clubs, but data obtained by getting the subject to take practice hits with one golf club (hereinafter, reference club) and performing simulation based on the data measured at this time.

The specifications (golf club weight $m_2$[g], center-of-gravity distance L [mm], moment of inertia $I_2$ [kg·cm²]) of the reference club were (272, 936, 453). Also, a sensor unit 1 such as used in the measurement process was attached to the reference club. The subject was then made to take practice hits with the reference club, inverse kinetic analysis was performed in accordance with a similar algorithm to the abovementioned algorithm, and torque $T_1$ about the shoulder, torque $T_2$ about the grip 42 and arm length R were calculated. Next, forward kinetic analysis was performed using the values of the specifications (golf club weight $m_2$, center-of-gravity distance L, moment of inertia $I_2$, etc.) of the 13 golf clubs, assuming that the parameters $T_1$, $T_2$ and R are constant. Note that, in the simulation of FIG. 30, golf clubs having a golf club weight $m_2$ of 272 g (constant) were used, and the specifications (L, $I_2$) of the 12 remaining golf clubs excluding the reference club, were (941, 192), (941, 138), (938.5, 324), (936, 507), (941, 83), (938.5, 270), (933.5, 633), (931, 809), (936, 399), (933.5, 578), (931, 755) and (931, 700). Head speed $V_h$, grip end moment of inertia $I_G$, and swing moment of inertia $I_S$ of each golf club were calculated using the above forward kinetic analysis. The ten diagonal lines drawn in FIG. 30 are the contour lines of head speed $V_h$ derived based on the values of 13 head speeds $V_h$.

The results of having performed similar simulation on 13 different golf clubs are shown in FIGS. 31 and 32. Specifically, in the simulation of FIG. 31, golf clubs having a center-of-gravity distance L of 936 cm (constant) were used, and the specifications ($m_2$, $I_2$) of the 12 remaining golf clubs excluding the reference club were (284, 349), (284, 294), (278, 400), (272, 507), (284, 240), (278, 346), (266, 560), (260, 666), (272, 399), (266, 506), (260, 612) and (260, 557). Also, in the simulation of FIG. 32, golf clubs having an moment of inertia $I_2$ of 453 kg·cm² (constant) were used, and the specifications (L, $m_2$) of the 12 remaining golf clubs excluding the reference club were (932.6, 293), (930.9, 297), (934.3, 282), (937.8, 267.6), (929.2, 302), (932.5, 287), (933.5, 258), (943.5, 244), (934.2, 276.4), (937.8, 262), (941.5, 248) and (939.7, 252).

The contour diagrams in FIGS. 30 to 32 are drawn at 0.1 m/s intervals. The numerical values attached to these contour lines are the values of relative head speeds $V_h$ when head speed $V_h$ of the reference club is taken as 0.0 m/s. It is evident from these contour diagrams that, in the $I_G$-$I_S$ plane, head speed $V_h$ improves downward to the right and drops upward to the left. In other words, it is evident that head speed $V_h$ improves as the value of swing moment of inertia $I_S$ decreases and the value of grip end moment of inertia $I_G$ increases. This tendency is not dependent on conditions such as the golf club weight $m_2$ being constant, center-of-gravity distance L being constant or moment of inertia $I_2$ being constant.

Incidentally, it is generally thought that when grip end moment of inertia $I_G$ and swing moment of inertia $I_S$ increase, the golf club becomes more difficult to swing since the position of the center of gravity approaches the head, causing a drop in head speed $V_h$. However, the inventors noticed from the simulation results of FIGS. 30 to 32 that, even given an increase in swing moment of inertia $I_G$, for example, head speed $V_h$ can actually be improved if the increase in grip end moment of inertia $I_S$ relative to this increase in swing moment of inertia $I_G$ is at or below a given value. Further investigation by the inventors revealed that this can be described from the results of different simulation shown in FIG. 33.

Figure 33:
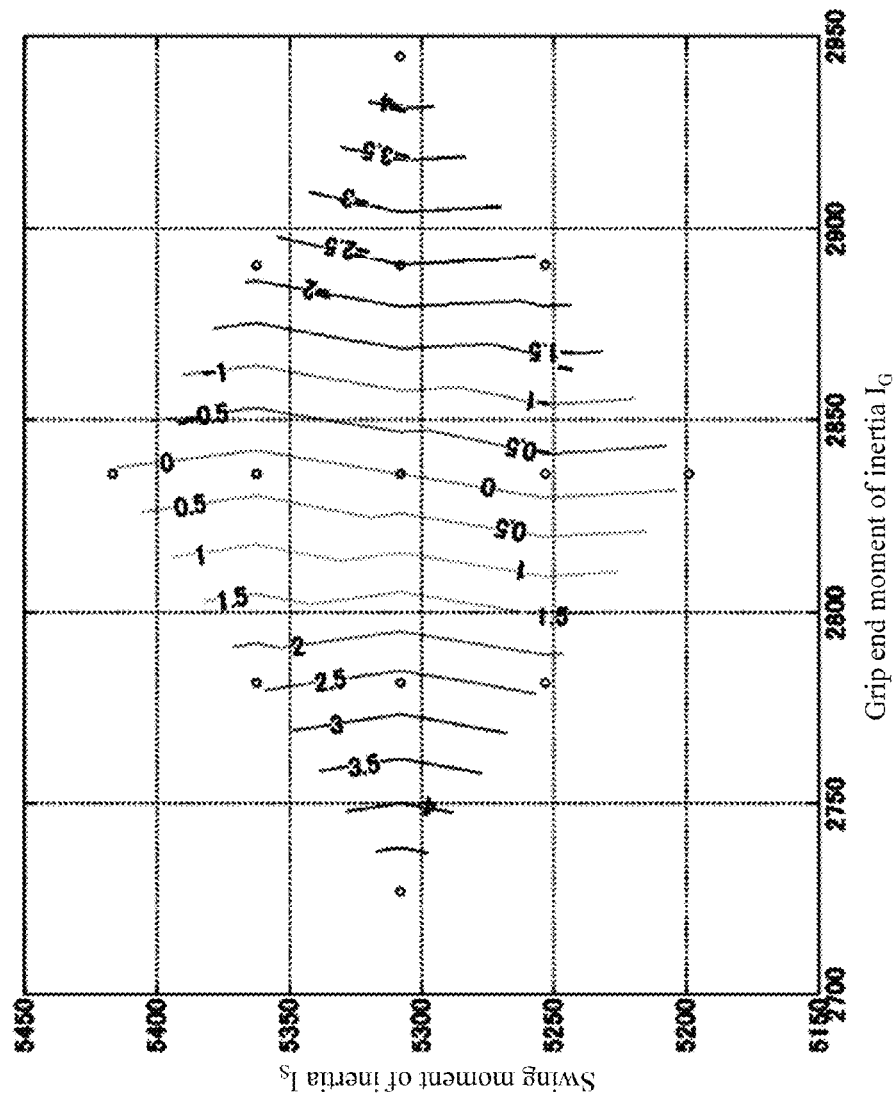
FIG. 33 is a contour diagram of wrist-cock angles derived through simulation.

FIG. 33 is a contour diagram of wrist-cock angles derived based on the values of 13 wrist-cock angles at the time of the subject swinging the 13 golf clubs in the simulation of FIG. 30. Note that a wrist-cock angle as referred to here is the angle formed by the arm and the golf club at wrist-cock release timing $t_r$ (angle shown in FIG. 11 with a dashed-dotted line).

The contour lines in FIG. 33 are drawn at 0.5 degree intervals. The numerical values attached to these contour lines are relative angles when the wrist-cock angle of the reference club is taken as 0.0 degrees. It is evident from these contour diagrams that, in the $I_G$-$I_S$ plane, the wrist-cock angle becomes smaller towards the right and increases towards the left. In other words, it is evident that the wrist-cock angle becomes smaller as grip end moment of inertia $I_G$ increases. In the other hand, given that the contour lines generally extend vertically up and down, the wrist-cock angle is not affected by swing moment of inertia $I_S$. Note that, for ease of description, only the results of the simulation corresponding to FIG. 30 are shown, but a similar tendency regarding the wrist-cock angle was confirmed in the simulations corresponding to FIGS. 31 and 32.

Also, a small wrist-cock angle means that the wrist cock is being held and the golf club passes close to the golfer's body during the swing. Accordingly, in the case where the wrist-cock angle is small, the effectual swing moment of inertia $I_S$ decreases and an increase in head speed $V_h$ can be expected.

It is evident from the above that even when grip end moment of inertia $I_G$ increases, if the increase in swing moment of inertia $I_S$ is at or below a fixed value, the advantage gained from the wrist-cock angle being small outweighs the disadvantage of the golf club becoming more difficult to swing, and head speed $V_h$ improves. That is, head speed $V_h$ can be improved if grip end moment of inertia $I_G$ can be increased and swing moment of inertia $I_S$ can be reduced.

The optimal club specification process is executed based on the above findings. First, the optimal club specification unit 24G narrows down the candidate clubs from among the plurality of target clubs that are targeted for fitting. Specifically in the storage unit 23, information showing the specifications of each target club (hereinafter, specification information) is stored in advance. In the present embodiment, values such as golf club weight $m_2$, moment of inertia $I_2$ about the center of gravity of the golf club 4, and distance (center-of-gravity distance) L from the grip 42 to the center of gravity of the golf club 4 are stored with respect to each target club as specifications as referred to here. Accordingly, the optimal club specification unit 24G specifies all the golf clubs belonging to the optimal weight zone, optical shaft weight zone and optical stiffness range as candidate clubs from among the target clubs, by referring to the specification information in the storage unit 23. Note that in the case where there is only one candidate club, the following processing is omitted and that one candidate club is specified as the optimal club.

On the other hand, if there are a plurality of candidate clubs, the optimal club, being the golf club that can particularly increase head speed, is specified from among these candidate clubs. Specifically, the optimal club specification unit 24G derives grip end moment of inertia $I_G$ and swing moment of inertia $I_S$ that would occur at the time that the golfer 7 who is undergoing fitting swung each of the candidate clubs, in accordance with the abovementioned definitional equation. At this time, forward kinetic analysis is executed using a parameter R that has already been calculated in processes from the measurement process to the index calculation process and the values of specifications (golf club weight $m_2$, center-of-gravity distance L, moment of inertia $I_2$, etc.) of the candidate clubs. In this case, the golfer 7 does not need to swing the candidate clubs again.

Figure 34B:
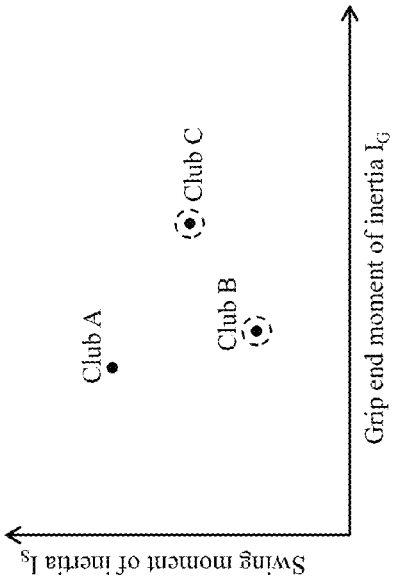
FIGS. 34A to 34C are diagrams illustrating an optimal club specification process.
Figure 34C:
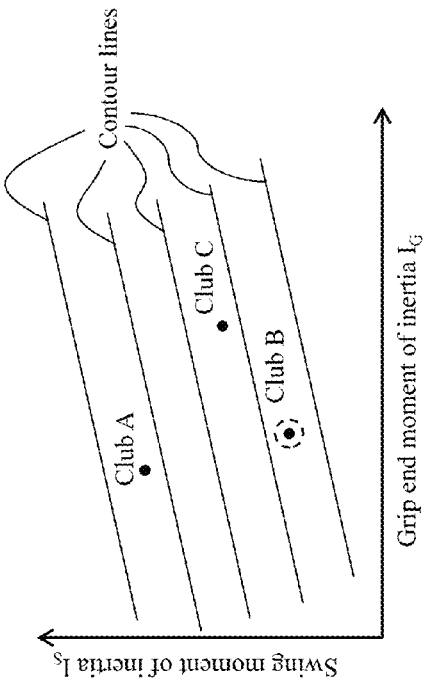
Figure 34A:
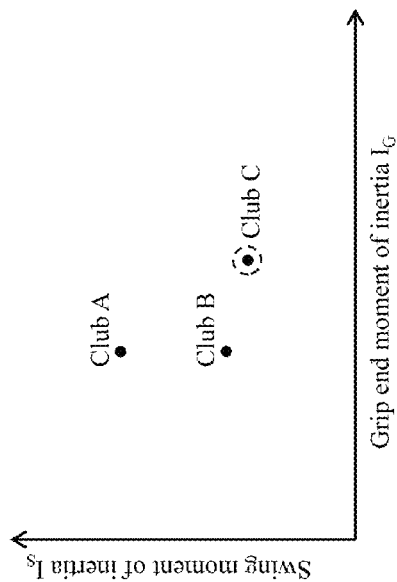

When moments of inertia $I_G$ and $I_S$ corresponding to each candidate club become known, the optimal club specification unit 24G specifies the golf club having both smaller swing moment of inertia $I_S$ and larger grip end moment of inertia $I_G$, from among the plurality of candidate clubs, and takes this golf club as the optimal club. Specifically, the optimal club specification unit 24G plots the points of ($I_G$, $I_S$) corresponding to each candidate club in an $I_G$-$I_S$ plane, and determines that the candidate club corresponding to the most lower right point to be the optimal club. For example, in the case where three candidate clubs A, B and C such as shown in FIG. 34A exist, the candidate club C is determined to be the optimal club. On the other hand, in the case where three candidate clubs A, B and C such as shown in FIG. 34B exist, it cannot be determined which of the candidate clubs B and C is the most lower right. In this case, both B and C are determined as optimal clubs.

Note that the relative merits of the plurality of candidate clubs corresponding to B and C in FIG. 34B can also be judged if contour lines such as shown in FIGS. 30 to 32 can be drawn in the $I_G$-$I_S$ plane. Accordingly, in another embodiment, a configuration may be adopted in which the optimal club specification unit 24G derives the contour line of head speed $V_h$ in the $I_G$-$I_S$ plane through forward kinetics analysis, using parameters $T_1$, $t_2$ and R that have already been calculated, and the values of various predetermined specifications (golf club weight $m_2$, center-of-gravity distance L, moment of inertia $I_2$, etc.) of golf clubs. Note that this contour line is dependent on the golfer 7. the relative levels of head speeds $V_h$ corresponding to a plurality of candidate clubs such as B and C can then be judged (see FIG. 34C) from the slope of this contour line, and the candidate club having the highest head speed $V_h$ can be determined to be the optimal club.

When the above processing has ended, the display control unit 24F displays information specifying the optimal club on the display unit 21. The golfer 7 can thereby comprehend the optimal golf club for himself or herself. The display control unit 24F is also able to combine display of the graphs shown in FIGS. 34A to 34C on the display unit 21, in order to improve the persuasiveness of the output values.

5. Modifications

Although embodiments of the present invention have been described above, the present invention is not limited to the above embodiments, and variations that do not depart from the gist of the invention are possible. For example, the following variations are possible. Also, the substance of the following modifications can be combined as appropriate.

5-1

In the above embodiments, a sensor unit 1 having three sensors, namely, an acceleration sensor, an angular velocity sensor and a geomagnetic sensor, was used as the measurement device that measures the swing action of the golfer 7, but other configurations of the measurement device can also be adopted. For example, the geomagnetic sensor can be omitted. In this case, it is possible to use a statistical technique to change the measurement data from the xyz local coordinate system to the XYZ global coordinate system. Note that since such techniques are well-known technologies (if needed, see JP 2013-56074A), detailed description thereof will be omitted here. Alternatively, a three-dimensional measurement camera can be used as the measurement device. Since techniques for measuring the behavior of golfers, golf clubs and golf balls using a three-dimensional measurement camera are also well-known, detailed description thereof will be omitted here. Note that, in the case where a three-dimensional measurement camera is used, the transformation process from the xyz local coordinate system to the XYZ global coordinate system of measurement data can be omitted, and the behavior of the grip in the XYZ global coordinate system can be directly measured.

5-2

Head speed $V_h$ can also be calculated with another method, than with a statistical technique that is based on the abovementioned multiple regression equation. For example, head speed $V_h$ may be calculated geometrically in accordance with the following equation. Note that $L_{club}$ is the length of the golf club, which is a specification of the golf club.

Position vector ($d_{hX}$, $d_{hY}$) of head at distal end of shaft 40

$$d_{hX}=2X_1+L_{club} \cos \theta_2$$

$$d_{hY}=2Y_1+L_{club} \sin \theta_2$$

Velocity vector ($V_{hX}$, $V_{hY}$) of head at distal end of shaft 40

$$V_{hX}=2V_{X1}-L_{club}\omega_2 \sin \theta_2$$

$$V_{hY}=2V_{Y1}+L_{club}\omega_2 \cos \theta_2$$

$$V_h=\text{sqrt}(V_{hX}^2+V_{hY}^2)$$

5-3

The optimal total weight determination process, the optimal swing MI determination process and the optimal grip end MI determination process can be executed by user himself or herself rather than the fitting apparatus 2, 102, 202 or 302. That is, the calculated swing indices are displayed on the display unit 21 after the end of the index calculation process. The user may then judge the optimal weight zone, the optimal swing MI zone and the optimal grip end MI zone himself or herself, based on the correspondence data 28, 128 or 228 as shown in FIGS. 19, 20, 25 and 28. At this time, user's judgment will be facilitated if the correspondence data 28, 128 or 228 is displayed on the display unit 21 or a paper medium on which the correspondence data 28, 128 or 228 is prepared. Similarly, part or all of the processing of the optimal shaft determination process and/or the optimal club specification process can also be executed by the user himself or herself instead of the fitting apparatus 2, 102, 202 or 302.

5-4

The swing indices shown with the above embodiments are exemplary, and various other indices having a certain relationship (correlation) with an optimal swingability index such as optimal club weight, optimal swing MI and optimal grip end MI can be used. For example, the swing indices are not limited to arm energy $E_{AVE}$ and average shoulder torque $T_{AVE}$, and arm energy $E_1$ and shoulder torque $T_{t1}$ can be used as swing indices. Also, an index representing the energy or torque exerted by the golfer 7 during the swing action on an arbitrary site can be used as a swing index. Also, "during the swing action" as referred to here is not limited to the time period from the top to impact or wrist-cock release timing described in the above embodiment, and can be said to refer to an arbitrary time or time period during the swing action, as long as there is a certain relationship (correlation) between the swing index and the optimal club weight. Also, the following indices that conceivable have a certain relationship (correlation) with the energy or torque that is exerted by the golfer 7 can also be used as swing indices. Note that with the following indices apart from (7) to (9), the optimal swingability index tends to increase as the value of index increases, and that with the indices of (7) to (9), the optimal swingability index tends to increase as the value of the index decreases.

Figure 35:
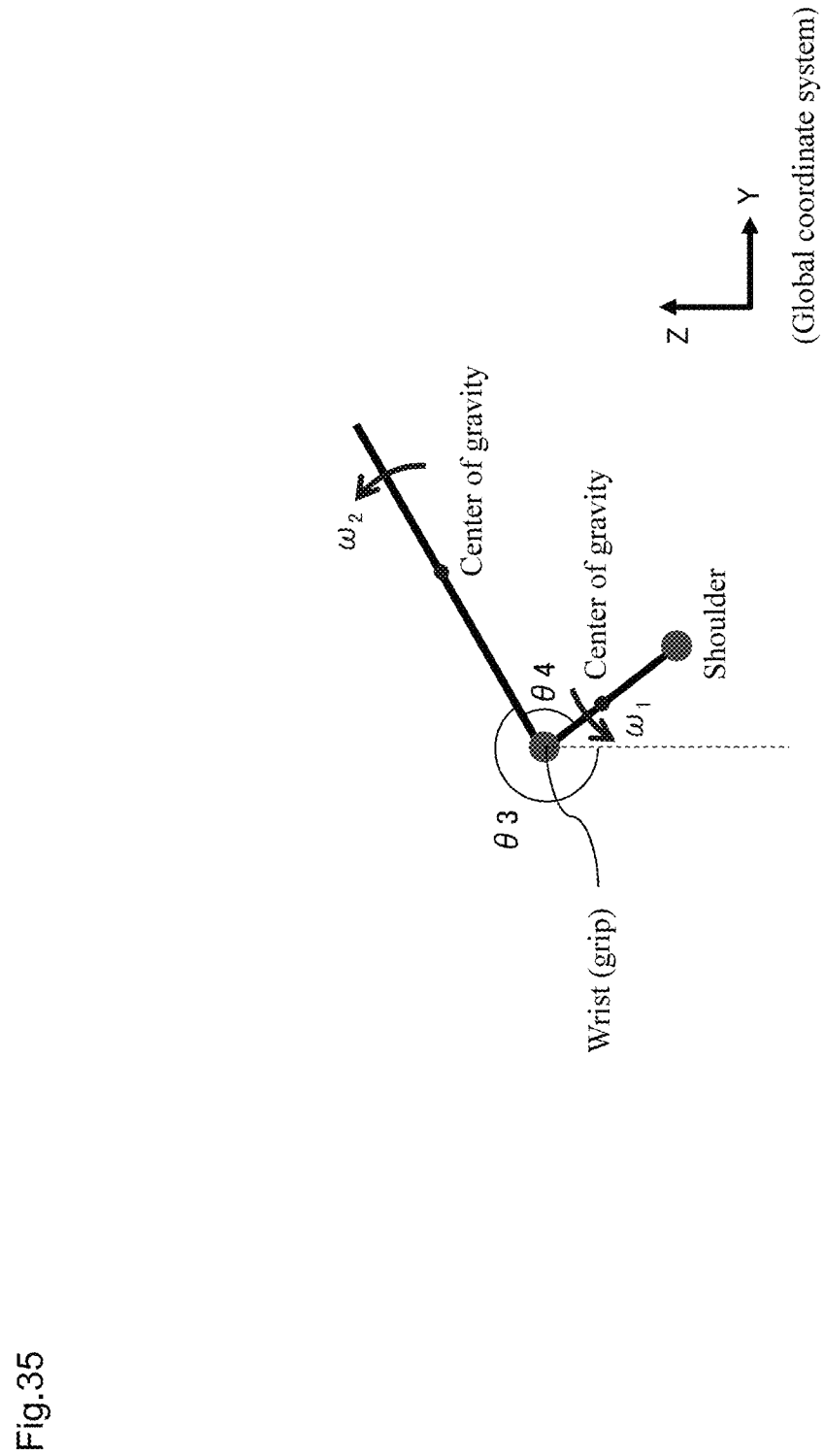
FIG. 35 is a diagram illustrating various types of angles which are swing indices according to a modification.

(1) Angle θ3 formed by the shaft 40 and the Z-axis (below the grip) of the global coordinate system at the top (see FIG. 29)
(2) Average value of angular velocity $\theta_2$ during the swing action
(3) Maximum value of angular velocity $\theta_2$ from top to impact
(4) Average value of grip speed $V_{GE}$ from top to impact
(5) Maximum value of grip speed $V_{GE}$ from top to impact
(6) Movement distance D of the grip 42 from top to impact
(7) Difference between wrist-cock release timing $t_r$ and the time of impact (wrist-cock release timing $t_r$ referred to here can be defined as the timing at which the release speed of the wrist-cock angle θ4 formed by the arm and the shaft 40 quickens, and the energy of the arm starts to change to the energy of the shaft 40.)
(8) Wrist-cock angle θ4 formed by the arm and the shaft 40 at wrist-cock release timing $t_r$ (see FIG. 35)
(9) Downswing time, i.e., time from top to impact
(10) Integral value of torque $T_2$ from the top to when the sign of torque $T_2$ about the grip 42 inverts

5-5

In the above embodiments, an optimal swingability indices such as optimal club weight, optimal swing MI or optimal grip end MI was determined according to the magnitudes of three swing indices (head speed $V_h$, arm energy $E_{AVE}$, and average shoulder torque $T_{AVE}$), but the optimal swingability index may be determined according to the magnitudes of one, two or four or more swing indices. For example, the optimal swingability index can be determined according to the magnitudes of only one or two arbitrary indices selected from the three indices arm energy $E_{AVE}$, average shoulder torque $T_{AVE}$, and head speed $V_h$. Note that it is evident from the results of the testing shown in FIGS. 17, 18 and 23 that arm energy $E_{AVE}$ and average shoulder torque $T_{AVE}$ have a higher correlation with the optimal swingability index than with head speed $V_h$. Accordingly, head speed $V_h$, in the case of being used as a swing index, is preferably used in combination with at least one of arm energy $E_{AVE}$ and average shoulder torque $T_{AVE}$. The optimal swingability index can also be determined according to the magnitudes of an arbitrary numbers of indices selected from the swing indices illustrated in modification 5-4 in addition to $E_{AVE}$, $t_{AVE}$ and $V_h$.

5-6

In the above embodiments, calculating optimal club weight, optimal swing MI, and optimal grip end MI as optimal swingability indices was illustrated. However, the optimal value may be calculated for various other indices representing the swingability of a golf club, and used as the optimal swingability index. For example, moment of inertia $I_2$ about the center of gravity of a golf club is also correlated with swing indices, and the optimal value of moment of inertia $I_2$ about the center of gravity of a golf club may be calculated as the optimal swingability index. Also, in the above embodiment, although optimal club weight, optimal swing MI or optimal grip end MI was calculated as the optimal swingability index, a plurality of optimal swingability indices may be calculated, and fitting may be performed based on all of these optimal swingability indices. For example, optimal club weight, optimal swing MI and optimal grip end MI may all be calculated, and a database may be searched for golf clubs that meet these three conditions.

Working Example

Hereinafter, a working example of the present invention will be described. The present invention is, however, not limited to the following working example.

The results shown in the following tables 3 and 4 were obtained after getting five pro model users to take practice hits with the pro model club and five average model users to take practice hits with the average model club and then calculating average shoulder torque $T_{AVE}$, arm energy $E_{AVE}$ and head speed $V_h$. Note that the values of $T_{AVE}$ and $E_{AVE}$ were calculated in accordance with similar processes as the processing from the measurement process to the index calculation process. Also, the value of $V_h$ was measured with a BCS system. The BCS system used here is a measuring system that is disclosed in JP 2012-170547A and JP 2012-170532A that were filed by the applicants. Also, the optimal weight zone was derived with the method according to the first embodiment, and the optimal club weight at which the carry distance is maximized was derived with a similar method to the testing described in the first embodiment.

TABLE 3

| Pro model user | Head speed [m/s] | Average shoulder torque [N · m] | Arm energy [N · m/s] | Optimal weight zone according to working example [g] | Optimal club weight though testing [g] |
| --- | --- | --- | --- | --- | --- |
| P1 | 44.79 | 92.53 | 350.12 | 320~310 | 316 |
| P2 | 47.81 | 84.56 | 315.02 | 320~310 | 316 |
| P3 | 42.03 | 72.09 | 260.99 | 315~305 | 316 |
| P4 | 43.98 | 67.01 | 230.29 | 310~300 | 308 |
| P5 | 43.62 | 57.55 | 172.5 | 310~300 | 308 |

TABLE 4

| Average model user | Head speed [m/s] | Average shoulder torque [N · m] | Arm energy [N · m] | Optimal weight zone according to working example [g] | Optimal club weight though testing [g] |
| --- | --- | --- | --- | --- | --- |
| A1 | 38.11 | 65.54 | 197.07 | 300~290 | 295 |
| A2 | 40.37 | 56.5 | 163.4 | 300~290 | 295 |
| A3 | 38.01 | 57.76 | 131.45 | 300~290 | 290 |
| A4 | 36.77 | 50.57 | 129.88 | 300~290 | 285 |
| A5 | 35.45 | 43.04 | 90.19 | 290 or less | 285 |

The above result show that the optimal weight zone according to this working example matched with the optimal club weight obtained through testing, except for the one person P3 out of the five persons with regard to the pro model users. Even with regard to the one person for which a match was not obtained, there was not a big discrepancy between both values. Also, with regard to the average model users, the optimal weight zone obtained with the method according to this working example matched with the optimal club weight obtained through testing, except for one person A4 out of the five persons. Also, even with regard to the one person for which a match was not obtained, there was not a big discrepancy between both values. The high accuracy of the fitting method according to the first embodiment was thereby confirmed.

Also, out of the plurality of golf clubs used by the above golfers P1, P2, P4 and P5 and A1, A2 and A5 in testing for deriving of the optimal club weight, the specifications (length of golf club, weight of head, weight of shaft, weight of grip, total weight $m_2$ of golf club) of the golf clubs having the optimal club weight (hereinafter, test clubs) were as shown in table 5 below. Also, swing moment of inertia $I_S$ and grip end moment of inertia $I_G$ at the time that each golfer had used the test club were calculated, in accordance with the above definitional equations. These golfers P1, P2, P4 and P5 and A1, A2 and A5 were made to swing a different golf club (hereinafter, verification club) belonging to the optimal weight zone that had a larger grip end moment of inertia $I_G$ and a smaller swing moment of inertia $I_S$ than the test club. The specifications of the verification clubs were as shown in Table 5. Also, the results of having measured head speed $V_h$ at the time of swinging the verification club using the BCS system, similarly to the above, were as shown in the following table 5. Note that the golfers P3 and A4 were not targeted for verification, since the optimal weight zone obtained with the method according to this working example did not match the optimal club weight obtained through testing. Also, the golfer A3 was not targeted for verification, since a suitable verification club could not be provided.

TABLE 5

| | P1 | | P2 | | P4 | | P5 | |
| --- | --- | --- | --- | --- | --- | --- | --- | --- |
| | Test club | Verification club | Test club | Verification club | Test club | Verification club | Test club | Verification club |
| Golf club length [cm] | 114.3 | 114.3 | 114.3 | 113.665 | 114.3 | 114.3 | 114.3 | 113.7 |
| Head weight [g] | 202 | 202 | 202 | 205 | 197 | 197.5 | 197 | 199 |
| Shaft weight [g] | 61 | 62 | 61 | 59 | 58 | 58 | 58 | 60 |
| Grip weight [g] | 49 | 42 | 49 | 42 | 49 | 40.5 | 49 | 37 |
| Golf club total weight $m_2$ [g] | 316 | 310 | 316 | 310 | 308 | 300 | 308 | 300 |
| Swing moment of inertia $I_S$ [kg · cm2] | 5586 | 5577 | 5586 | 5583 | 5440 | 5432 | 5440 | 5437 |
| Grip end moment of inertia $I_G$ [kg · cm2] | 2921 | 2923 | 2921 | 2924 | 2847 | 2853 | 2847 | 2849 |
| Head speed $V_h$ [m/s] | 44.86 | 44.94 | 47.85 | 47.94 | 44.09 | 44.14 | 43.65 | 43.72 |

| | A1 | | A2 | | A5 | |
| --- | --- | --- | --- | --- | --- | --- |
| | Test club | Verification club | Test club | Verification club | Test club | Verification club |
| Golf club length [cm] | 115.57 | 115.57 | 115.57 | 115.57 | 115.57 | 115.57 |
| Head weight [g] | 195 | 195 | 195 | 195 | 194 | 194 |
| Shaft weight [g] | 50 | 51 | 50 | 51 | 54 | 55 |
| Grip weight [g] | 46 | 40 | 46 | 40 | 33 | 27 |
| Golf club total weight $m_2$ [g] | 295 | 290 | 295 | 290 | 285 | 280 |
| Swing moment of inertia $I_S$ [kg · cm2] | 5407 | 5402 | 5407 | 5402 | 5308 | 5302 |
| Grip end moment of inertia $I_G$ [kg · cm2] | 2861 | 2863 | 2861 | 2863 | 2799 | 2802 |
| Head speed $V_h$ [m/s] | 38.16 | 38.21 | 40.41 | 40.45 | 35.51 | 35.56 |

The above results confirmed that the verification club has a faster head speed $V_h$ than the test club. That is, it was confirmed that the optimal club specification process according to the above embodiments enables golf clubs that can enhance head speed $V_h$ to be narrowed down.

| Reference Signs List | |
| --- | --- |
| 1 | Sensor unit (measuring device) |
| 2, 102, 202 | Fitting apparatus |
| 3, 103, 203 | Fitting program |
| 4 | Golf club |
| 7 | Golfer |
| 24A | Acquisition unit (input unit, receiver) |
| 24B | Grip behavior derivation unit |
| 24C | Shoulder behavior derivation unit |
| 24D | Index calculation unit (calculation unit) |
| 24E, 24E, 224E | Determination unit |
| 41 | Head |
| 42 | Grip |

The invention claimed is:

1. A fitting apparatus configured to determine an optimal swingability index, which is a swingability index of a golf club suited to a golfer, comprising:
an acquisition unit configured to acquire a measurement value obtained by measuring a swing action of a test club by the golfer with a measurement device;
a calculation unit configured to calculate a swing index indicating a feature amount of the swing action, based on the measurement value; and
a determination unit configured to determine the optimal swingability index, according to a magnitude of the swing index,
wherein:
the swing index includes at least one of arm energy of the golfer during the swing action and torque about a shoulder of the golfer during the swing action, and head speed, the arm energy and the torque being exerted by the golfer during the swing action,
the calculation unit is configured to calculate the head speed achieved during the swing action, and
the determination unit is configured to determine the optimal swingability index, according to the magnitude of the head speed, in addition to the magnitude of at least one of the arm energy and the torque about the shoulder.

2. The fitting apparatus according to claim 1,
wherein the calculation unit is configured to calculate a plurality of types of swing indices, and
the determination unit is configured to determine the optimal swingability index, according to the magnitudes of the plurality of types of the swing indices.

3. The fitting apparatus according to claim 1,
wherein the determination unit is configured to determine the optimal swingability index to take a larger value as the swing index increases or decreases.

4. The fitting apparatus according to claim 1, further comprising:
a storage unit which stores correspondence data defining a correspondence between the magnitude of the swing index and the magnitude of the optimal swingability index for each type of the test club,
wherein the determination unit is configured to determine the optimal swingability index according to the type of the test club, by referring to the correspondence data in the storage unit.

5. The fitting apparatus according to claim 1,
wherein the swingability index includes at least one of a moment of inertia of the golf club, and a moment of inertia about a shoulder of the golfer.

6. The fitting apparatus according to claim 1,
wherein the swingability index includes a weight of the golf club.

7. The fitting apparatus according to claim 6, further comprising:
an optimal club specification unit configured to specify a golf club having a small swing moment of inertia and a large grip end moment of inertia from among a plurality of golf clubs that match an optimal club weight, which is a weight of the golf club suited to the golfer.

8. A fitting method for determining an optimal swingability index, which is a swingability index of a golf club suited to a golfer, comprising the steps of:
measuring a swing action of a test club by the golfer with a measurement device,
calculating a swing index indicating a feature amount of the swing action, based on the measurement value measured with the measurement device; and
determining the optimal swingability index, according to a magnitude of the swing index,
wherein:
the swing index includes at least one of arm energy of the golfer during the swing action and torque about a shoulder of the golfer during the swing action, and head speed, the arm energy and the torque being exerted by the golfer during the swing action,
the calculating the swing index includes calculating the head speed achieved during the swing action, and
the determining the optimal swingability index includes determining the optimal swingability index, according to the magnitude of the head speed, in addition to the magnitude of at least one of the arm energy and the torque about the shoulder.

9. The fitting method according to claim 8,
wherein the swingability index includes at least one of a moment of inertia of the golf club, and a moment of inertia about a shoulder of the golfer.

10. The fitting method according to claim 8,
wherein the swingability index includes a weight of the golf club.

11. The fitting method according to claim 10, further comprising the step of:
specifying a golf club having a small swing moment of inertia and a large grip end moment of inertia from among a plurality of golf clubs that match an optimal club weight, which is a weight of the golf club suited to the golfer.

12. A non-transitory computer readable medium storing a fitting program for determining an optimal swingability index, which is a swingability index of a golf club suited to a golfer, the program causing a computer to execute the steps of:
acquiring a measurement value obtained by measuring a swing action of a test club by the golfer with a measurement device;
calculating a swing index indicating a feature amount of the swing action, based on the measurement value measured with the measurement device; and
determining the optimal swingability index, according to a magnitude of the swing index,
wherein:
the swing index includes at least one of arm energy of the golfer during the swing action and torque about a shoulder of the golfer during the swing action, and head speed, the arm energy and the torque being exerted by the golfer during the swing action,
the calculating the swing index includes calculating the head speed achieved during the swing action, and the determining the optimal swingability index includes determining the optimal swingability index, according to the magnitude of the head speed, in addition to the magnitude of at least one of the arm energy and the torque about the shoulder.

13. The non-transitory computer readable medium according to claim 12,
wherein the swingability index includes at least one of a moment of inertia of the golf club, and a moment of inertia about a shoulder of the golfer.

14. The non-transitory computer readable medium according to claim 12,
wherein the swingability index includes a weight of the golf club.

15. The non-transitory computer readable medium according to claim 14, the program causing the computer to further execute the step of:
specifying a golf club having a small swing moment of inertia and a large grip end moment of inertia from among a plurality of golf clubs that match an optimal club weight, which is a weight of the golf club suited to the golfer.

* * * * *